(12) United States Patent
Ahn et al.

(10) Patent No.: US 9,856,206 B2
(45) Date of Patent: *Jan. 2, 2018

(54) OLIGO-BENZAMIDE COMPOUNDS AND THEIR USE

(71) Applicant: The Board of Regents of the University of Texas System, Austin, TX (US)

(72) Inventors: Jung-Mo Ahn, Plano, TX (US); Ganesh Raj, Plano, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/932,480

(22) Filed: Nov. 4, 2015

(65) Prior Publication Data

US 2016/0130217 A1 May 12, 2016

Related U.S. Application Data

(63) Continuation of application No. 13/700,500, filed as application No. PCT/US2011/038395 on May 27, 2011, now abandoned.

(60) Provisional application No. 61/349,555, filed on May 28, 2010.

(51) Int. Cl.
| | |
|---|---|
| *C07C 237/44* | (2006.01) |
| *A61K 31/167* | (2006.01) |
| *C07C 235/56* | (2006.01) |
| *C07C 279/08* | (2006.01) |
| *C07D 493/10* | (2006.01) |
| *C07C 237/06* | (2006.01) |

(52) U.S. Cl.
CPC .......... *C07C 235/56* (2013.01); *A61K 31/167* (2013.01); *C07C 237/06* (2013.01); *C07C 237/44* (2013.01); *C07C 279/08* (2013.01); *C07D 493/10* (2013.01)

(58) Field of Classification Search
None
See application file for complete search history.

(56) References Cited

U.S. PATENT DOCUMENTS

| | | | |
|---|---|---|---|
| 1,903,899 | A | 4/1933 | Laska |
| 3,951,914 | A | 4/1976 | Kwolek |
| 5,212,203 | A | 5/1993 | Shroot et al. |
| 5,929,114 | A | 7/1999 | Domagala et al. |

(Continued)

FOREIGN PATENT DOCUMENTS

| | | |
|---|---|---|
| CN | 1849126 | 10/2006 |
| WO | WO 2005/025579 | 3/2005 |

(Continued)

OTHER PUBLICATIONS

The ACS Style Guide, Second Ed., Janet S. Dodd (Ed.), American Chemical Society (Washington, DC), p. 50 (1997).*

(Continued)

*Primary Examiner* — Theodore R. West
(74) *Attorney, Agent, or Firm* — Paker Highlander PLLC

(57) ABSTRACT

The present invention includes bis- and tris-benzamide compounds that block AR signaling and have anticancer activity. Uses for these compounds, and pharmaceutical compositions containing the same, also are provided.

20 Claims, 37 Drawing Sheets

(56) References Cited

U.S. PATENT DOCUMENTS

| | | | |
|---|---|---|---|
| 7,217,720 B2 | 5/2007 | Meissner et al. | |
| 7,816,324 B2 | 10/2010 | Ahn et al. | |
| 7,906,624 B2 | 3/2011 | Green et al. | |
| 8,236,983 B2 | 8/2012 | Ahn | |
| 8,618,324 B2 | 12/2013 | Ahn | |
| 8,754,124 B2 | 6/2014 | Ahn et al. | |
| 8,835,493 B2 | 9/2014 | Ahn et al. | |
| 9,072,705 B2 | 7/2015 | Ahn et al. | |
| 9,458,095 B2 * | 10/2016 | Ahn | A61K 31/167 |
| 2005/0261346 A1 | 11/2005 | Zhu et al. | |
| 2007/0248535 A1 | 10/2007 | Buttyan et al. | |
| 2009/0012141 A1 | 1/2009 | Ahn | |
| 2009/0275519 A1 | 11/2009 | Nash et al. | |
| 2010/0069333 A1 | 3/2010 | Kahn | |
| 2010/0125055 A1 | 5/2010 | Kufe et al. | |
| 2010/0178324 A1 | 7/2010 | Ahn | |
| 2010/0317570 A1 | 12/2010 | Ahn et al. | |
| 2013/0011465 A1 | 1/2013 | Ahn | |
| 2013/0150442 A1 | 6/2013 | Ahn et al. | |
| 2013/0184345 A1 | 7/2013 | Ahn et al. | |
| 2014/0127285 A1 | 5/2014 | Ahn | |
| 2016/0031803 A1 | 2/2016 | Ahn et al. | |

FOREIGN PATENT DOCUMENTS

| | | |
|---|---|---|
| WO | WO 2008/112938 | 9/2008 |
| WO | WO 2008/112939 | 9/2008 |
| WO | WO 2008/112941 | 9/2008 |
| WO | WO 2009/141238 | 11/2009 |
| WO | WO 2010/088498 | 8/2010 |
| WO | WO 2011/050353 | 4/2011 |
| WO | WO 2011/150360 | 12/2011 |

OTHER PUBLICATIONS

Adams et al., "Life-or-death decisions by the Bcl-2 protein family," *Trends Biochem. Sci*, 26:61-66, 2001.

Ahn et al., "A new approach to search the bioactive conformation of glucagon: positional cyclization scanning," *J. Med. Chem.*, 44:3109-3116, 2001.

Ahn et al., "Development of potent truncated glucagon antagonists," *J. Med. Chem.*, 44:1372-1379, 2001.

Ahn et al., "Facile synthesis of benzamides to mimic an α-helix," *Tetrahedron Letters*, 48:3543-3547, 2007.

Ahn et al., "Peptidomimetics and peptide backbone modifications," *Mini-Reviews in Medicinal Chemistry*, 2:463-473, 2002.

Bulotta et al., "A cultured pancreatic ductal cells undergo cell cycle re-distribution and beta-cell-like differentiation in response to glucagon-like peptide-1," *J. Mol. Endocrinol.*, 29:347-360, 2002.

Burgess et al., "Solid-phase syntheses of β-turn analogues to mimic or disrupt protein-protein interactions," *Acc. Chem. Res.*, 24:826-835, 2001.

Cavaghan et al., "Interactions between insulin resistance and insulin secretion in the development of glucose intolerance," *J. Clin. Invest.*, 106:329-333, 2000.

Chang et al., "Substituted imidazoles as glucagon receptor antagonists," *Bioorg. Med. Chem. Lett.*, 11:2549-2553, 2001.

Chapuis et al., "Shorter puromycin analog synthesis by means of an efficient Staudinger-Vilarrasa coupling," *Tetrahedron*, 62:12108-12115, 2006.

Chen et al., "A nonpeptidic agonist of glucagon-like peptide 1 receptors with efficacy in diabetic db/db mice," *Proc. Natl. Acad. Sci. USA*, 104:943-948, 2007.

Chittenden et al., "A conserved domain in Bak, distinct from BH1 and BH2, mediates cell death and protein binding functions," *EMBO J.*, 14:5589-5596, 1995.

Cochran, "Antagonists of protein-protein interactions," *Chem. Biol.*, 7:R85-R94, 2000.

Database CAPLUS on STN Acc. No. 2007:443215, Document No. 147:72511, Ahn et al., "Facile synthesis of benzamides to mimic an α-helix," *Tetrahedron* Letters, 48(20):3543-3547, 2007 (abstract only).

Database CAPLUS on STN Acc. No. 2008:1127781, Document No. 149:378403, Ahn, "Composition and method for making oligobenzamide compounds," 2008 (abstract only).

Database CAPLUS on STN Acc. No. 2009:1006344, Document No. 151:439821, Plante et al., "Oligobenzamide proteomimetic inhibitors of the p53-hDM2 protein-protein interaction," *Chemical Communications*, 34:5091-5093, 2009 (abstract only).

Database CAPLUS on STN Acc. No. 2010:1318082, Document No. 154:401514, Han et al., "Facile synthesis of glucagon-like peptide-1 (GLP-1) mimetics," *Advances in Experimental Medicine and Biology*, 611:119-120, 2010 (abstract only).

Database CAPLUS on STN Acc. No. 1937:30601, Document No. 31:30601, Izmail'skii et al., "Singular crystallization forms of certain derivatives of 1-amino-2-methyl-4-benzoylamino-5-methoxybenzene," *Zhurnal Obshchei Khimii*, 7:80-83, 1937 (abstract only).

Database CAPLUS on STN, Acc. No. 1998:159344, Document No. 128:265824, Gambacorti-Passerini et al., "Inhibition of the ABL kinase activity blocks the proliferation of BCR/ABL+ leukemic cells and induces apoptosis," *Blood Cells, Molecules & Diseases*, 23(3):380-394, 1997 (abstract only).

Database CAPLUS on STN, Acc. No. 2006:237099, Document No. 144:467879, Lu et al., "Proteomimetic libraries: design, synthesis, and evaluation of p53-MDM2 interaction inhibitors," *Journal of Combinatorial Chemistry*, 8(3):315-325, 2006 (abstract only).

Database CAPLUS on STN, Acc. No. 2007:1424768, Plante et al., *Organic & Biomolecular Chemistry*, 6(1):138-146, 2008. (Abstract).

Defronzo et al., "Effects of exenatide (exendin-4) on glycemic control and weight over 30 weeks in metformin-treated patients with type 2 diabetes," *Diabetes Care*, 28:1092-1100, 2005.

Dehm, et al., "Selective role of an NH2-terminal WxxLF motif for aberrant androgen receptor activation in androgen depletion independent prostate cancer cells," *Cancer Res.*, 67:10067-77, 2007.

Drucker et al., "The incretin system: glucagon-like peptide-1 receptor agonists and dipeptidyl peptidase-4 inhibitors in type 2 diabetes," *Lancet*, 368:1696-1705, 2006.

Druker, "Effects of a selective inhibitor of the Abl tyrosine kinase on the growth of Bcr-Abl positive cells," *Nature Medicine*, 2(5):561-566, 1996.

Edwards et al., "Exendin-4 reduces fasting and postprandial glucose and decreases energy intake in healthy volunteers," *Am. J. Physiol. Endocrinol. Metab.*, 281:E155-E161, 2001.

Egan et al., "GLP-1 receptor antagonists are growth and differentiation factors for pancreatic islet beta cells," *Diabetes/Metab. Res. Rev.*, 19:115-123, 2003.

Elbronds et al., "Pharmacokinetics, pharmacodynamics, safety, and tolerability of a single-dose of NN2211, a long-acting glucagon-like peptide 1 derivative, in healthy male subjects," *Diabetes Care*, 25:1398-1404, 2002.

Ernst et al., "Design and application of an α-helixmimetic scaffold based on an oligoamide-foldamer strategy: antagonism of the Bak BH3/Bcl-xL complex," *Angew. Chem. Int. Ed.*, 42:535-539, 2003.

European Extended Search Report issued in European Application No. 11787517.9, dated Nov. 23, 2015.

Gunther, et al., "Alternative inhibition of androgen receptor signaling: peptidomimetic pyrimidines as direct androgen receptor/coactivator disruptors," *ACS Chem. Biol.*, 4:435-40, 2009.

Hoare et al., "Mechanisms of peptide and nonpepetide ligand binding to class B G-proteincoupled receptors," *Drug Discovery Today*, 10:417-427, 2005.

Hruby et al., "Design in topographical space of peptide and peptidomimetic ligands that affect behavior. A chemist's glimpse at the mind—body problem," *Acc. Chem. Res.*, 34(5):389-397, 2001.

Izmail'skii, "Singular crystallization ofrms of certain derivatives of 1-amino-2-methyl-4-benzoylamino-5-methoxybenzene," *Zhurnal Obshchei Khimii*, 7:80-83, 1937.

Jacoby et al., "Biphenyls as potential mimetics of protein α-helix," *Bioorg. Med. Chem. Lett.*, 12:891-893, 2002.

Knudsen et al., "Glucagon-like peptide-1: the basis of a new class of treatment for type 2 diabetes," *J. Med. Chem.*, 47:4128-4134, 2004.

(56) References Cited

OTHER PUBLICATIONS

Knudsen et al., "Small-molecule agonists for the glucagon-like peptide 1 receptor," *Proc. Natl. Acad. Sci. U.S.A.*, 104:937-942, 2007.
Kolterman et al., "Synehetic exendin-4 (exenatide) significantly reduces postprandial and fasting plasma glucose in subjects with type 2 diabetes," *J. Clin. Endocrinol. Metab.*, 88:3082-3089, 2003.
Konig et al., "Solid-phase synthesis of oligo(p-benzamide) foldamers," *Organic Letters*, 8:1819-1822, 2006.
Konig et al., "Supramolecular PEG-co-Oligo(p-benzamide)s prepared on a peptide synthezier," *J. Am. Chem. Soc.*, 129:704-708, 2007. Published on Web Dec. 23, 2006.
Kulikov et al., "Hydrophobic side-chain interactions in a family of dimeric amide foldamers-potential alpha-helix mimetics," *Tetrahedron Letters*, 52:3705-3709, 2011.
Kussie et al., "Structure of the MDM2 oncoprotein bound to the p53 tumor suppressor transactivation domain," *Science*, 274:948-953, 1996.
Kutzki et al., "Development of a potent Bcl-xL antagonist based on α-helix mimicry," *J. Am. Chem. Soc.*, 124:11838-11839, 2002.
Lee et al., "Solid-phase synthesis of tris-benzamides as α-helix mimetics," *ACS Comb. Sci.*, 13:107-111, 2011.
Ling et al., "Identification of alkylidene hydrazides as glucagon receptor antagonists," *J. Med. Chem.*, 44:3141-3149, 2001.
Madsen et al., "Optimization of alkylidene hydrazide based human glucagon receptor antagonists. Discovery of the highly potent and orally available 3-cyano-4-hydroxybenzoic acid [1-(2,3,5,6-tetramethylbenzyl)-1H-indol-4-ylmethylene]hydrazide," *J. Med. Chem.*, 45:5755-5775, 2002.
Mahato et al., "Emerging trends in oral delivery of peptide and protein drugs," *Critical Reviews in Therapeutic Drug Carrier Systems*, 20:153-214, 2003.
Marshall, et al., "A hierarchical approach to peptidomimetic design," *Tetrahedron*, 49:3547-3558, 1993.
Matias, et al., "Structural evidence for ligand specificity in the binding domain of the human androgen receptor" *J. Bio. Chem.*, 275:26164-71, 2000.
Murphy, "Nonpeptidic glucagon-like peptide 1 receptor agonists: A magic bullet for diabetes," *Proc. Natl. Acad. Sci. U.S.A.*, 104:689-690, 2007.
Neidigh et al., "Exendin-4 and glucagon-likepeptide-1: NMR structural comparisons in the solution and micelle-associated states," *Biochemistry*, 40:13188-13200, 2001.
Office Action issued in Australian Application No. 2011258009, dated Aug. 12, 2014.
Office Action issued in Chinese Application No. 201180032395.8, dated Jan. 13, 2014 and English language translation thereof.
Office Action issued in Colombian Application No. 12-219.956, dated Dec. 4, 2013.
Office Action issued in Colombian Application No. 12-219956, dated Dec. 4, 2013.
Office Action issued in Japanese Application No. 2013-512048, dated Mar. 30, 2015, and English language translation thereof.
Office Action issued in Japanese Application No. 2013-512048, dated Feb. 22, 2016, and English language translation thereof.
Office Action issued in New Zealand Application No. 604038, dated Aug. 8, 2013.
Office Action issued in U.S. Appl. No. 12/048,197, dated Jan. 14, 2013.
Office Action issued in U.S. Appl. No. 12/048,197, dated Jul. 6, 2011.
Office Action issued in U.S. Appl. No. 12/048,197, dated Jul. 12, 2010.
Office Action issued in U.S. Appl. No. 12/048,197, dated Mar. 23, 2012.
Office Action issued in U.S. Appl. No. 12/048,197, dated May 9, 2012.
Office Action issued in U.S. Appl. No. 12/048,197, dated Sep. 22, 2010.
Office Action issued in U.S. Appl. No. 12/353,173, dated Jan. 11, 2012.
Office Action issued in U.S. Appl. No. 12/353,173, dated Jun. 23, 2011.
Office Action issued in U.S. Appl. No. 12/353,173, dated Mar. 24, 2011.
Office Action issued in U.S. Appl. No. 13/559,388, dated May 2, 2013.
Office Action issued in U.S. Appl. No. 13/559,388, dated Nov. 7, 2012.
Office Action issued in U.S. Appl. No. 13/559,388, dated Sep. 9, 2013.
Office Action issued in U.S. Appl. No. 13/683,932, dated Jul. 10, 2013.
Office Action issued in U.S. Appl. No. 13/683,932, dated Oct. 11, 2013.
Office Action issued in U.S. Appl. No. 13/683,979, dated Dec. 9, 2013.
Office Action issued in U.S. Appl. No. 13/683,979, dated Jul. 10, 2013.
Office Action issued in U.S. Appl. No. 13/700,500, dated May 4, 2015.
Office Action issued in U.S. Appl. No. 13/700,500, dated Sep. 30, 2014.
Office Action issued in U.S. Appl. No. 14/064,276, dated Aug. 5, 2014.
Office Action issued in U.S. Appl. No. 14/064,276, dated Aug. 3, 2015.
Office Action issued in U.S. Appl. No. 14/064,276, dated Jan. 23, 2015.
Office Action issued in U.S. Appl. No. 14/259,644, dated Sep. 16, 2014.
Office Action issued in U.S. Appl. No. 14/792,072, dated Jan. 6, 2016.
Oguri et al., "Design and synthesis of a trans-fused polycyclic ether skeleton as an a-helix mimetic scaffold," *Tetrahedron Lett.*, 46:2179-2183, 2005.
Orner et al., "Towards proteomimetics: Terphenyl derivatives as structural and functional mimics of extended regions of a α-helix," *J. Am. Chem. Soc.*, 123:5382-5383, 2001.
PCT International Preliminary Report on Patentability issued in International Application No. PCT/US2011/038395, dated Dec. 13, 2012.
PCT International Search Report and Written Opinion issued in International Application No. PCT/US2008/056918, dated Sep. 10, 2008.
PCT International Search Report and Written Opinion issued in International Application No. PCT/US2008/056920, dated Aug. 1, 2008.
PCT International Search Report and Written Opinion issued in International Application No. PCT/US2010/020898, dated Aug. 20, 2010.
PCT International Search Report and Written Opinion issued in International Application No. PCT/US2011/038395, dated Sep. 13, 2011.
PCT International Search Report and Written Opinion issued in International Application No. PCT/US2012/066228, dated Feb. 8, 2013.
PCT International Search Report and Written Opinion issued in International Application No. PCT/US2012/066212, dated Mar. 1, 2013.
Peczuh et al., "Peptide and protein recognition by designed molecules," *Chem. Rev..*, 100:2479-2494, 2000.
Perry et al., "The glucagon-like peptides: a double-edged therapeutic sword," *Trends Pharmacol. Sci.*, 24:377-383, 2003.
Plante et al., "Synthesis of functionalised aromatic oligamide rods," *Organic & Biomolecular Chemistry*, 6:138-146, 2008.
Plante et al., "Synthesis of functionalized aromatic oligamide rods," *Org. Biomol. Chem.*, 6:138-146, 2008.
Rickard et al., "Intermittend treatment with parathyroid hormone (PTH) as well as a non-petide small molecule agonist of the PTH1 receptor inhibits adipocyte differentiation in human bone marrow stromal cells," *Bone*, 39:1361-1372, 2006.

(56) References Cited

OTHER PUBLICATIONS

Runge et al., Different domains of the glucagon and glucagon-like peptide-1 receptors provide the critical determinants of ligand selectivity, *Br. J. Pharmacol.*, 138:787-794, 2003.

Saraogi et al., "Synthetic α-helix mimetics as agonists and antagonists of islet amyloid polypeptide aggregation," *Angewandte Chemie*, 49:736-739, 2010.

Sattler et al., "Structure of Bcl-xL-Bak peptide complex: Recognition between regulators of apoptosis," *Science*, 275:983-986, 1997.

Shaginian et al., "Design, synthesis, and evaluation of an α-helix mimetic library targeting rotein-protein interactions," *Journal of the American Chemical Society*, 131(15):5564-5572, 2009.

Souers et al., "β-Turn mimetic library synthesis: scaffolds and applications," *Tetrahedron*, 57:7431-7448, 2001.

Stoffers et al., "Insulinotropics glucagon-like peptide 1 agonists stimulate expression of homeodomain protein IDX-1 and increase islet size in mouse pancreas," *Diabetes*, 49:741-749, 2000.

Tanatani et al., "Helical structures of N-alkylated poly(p-benzamide)s," *J. Am. Chem. Soc.*, 127:8553-8561, 2005.

Tibaduiza et al., "A small molecule ligand of the glucagon-like peptide 1 receptor targets its ammo-terminal hormone binding domain," *J. Biol. Chem.*, 276:37787-37793, 2001.

Toft-Nielsen et al., "Determinants of the effectiveness of glucagon-like peptide-1 in type 2 diabetes," *J. Clin. Endocrinol. Metab.*, 86:3853-3860, 2001.

Vilsboll et al., "No reactive hypoglycaemia in type 2 diabetic patients after subcutaneous administration of GLP-1 and intravenous glucose," *Diabetic Med.*, 18:144-149, 2001.

Walensky et al., "Activation of apoptosis in vivo by a hydrocarbon-stapled BH3 helix," *Science*, 305:1466-1470, 2004.

Written Opinion issued in Singapore Application No. 201208723-5, dated Jan. 22, 2014.

Yin et al., "Terephthalamide derivatives as mimetics of helical peptides: Disruption of the Bcl-xL/Bak interaction," *J. Am. Chem. Soc.*, 127:5463-5468, 2005.

Yin et al., "Terphenyl-based Bak BH3 α-helical proteomimetics as low-molecular-weight antagonists of Bcl-xL," *J. Am. Chem. Soc.*, 127:10191-10196, 2005.

Yin et al., "Terphenyl-based helical mimetics that disrupt the p53/HDM2 interaction," *Angew. Chem. Int. Ed.*, 44:2704-2707, 2005.

Zander et al., "Effect of 6-week course of glucagon-like peptide 1 on glycaemic control, insulin sensitivity, and beta-cell function in type 2 diabetes: a parallel-group study," *Lancet*, 359:824-830, 2002.

Zhang et al., "New approaches in the treatment of type 2 diabetes," *Curr. Opin. Chem. Biol.*, 4:461-467, 2000.

\* cited by examiner

FIGS. 2A-E

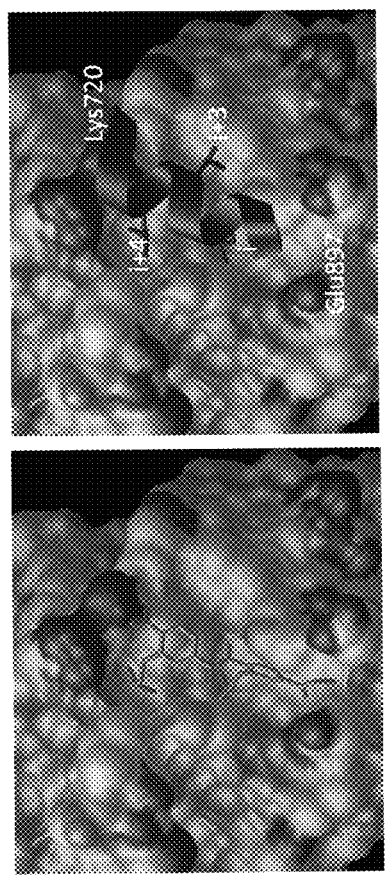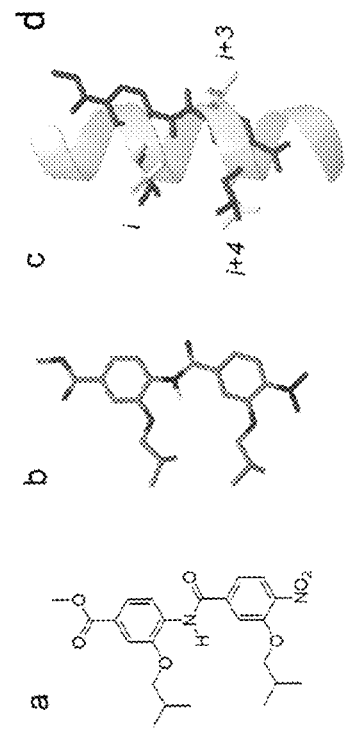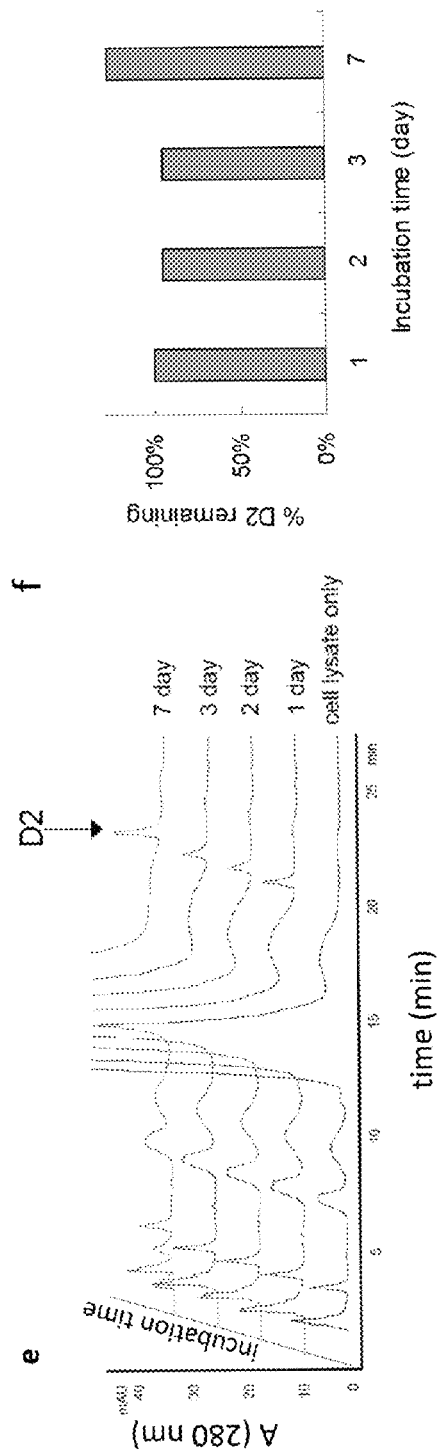
FIGS. 4A-F

OLIGO-BENZAMIDE COMPOUNDS AND THEIR USE

CROSS-REFERENCE TO RELATED APPLICATION

This application is a continuation of U.S. application Ser. No. 13/700,500, filed May 20, 2013, which is a national phase application under 35 U.S.C. §371 of International Application No. PCT/US2011/038395, filed May 27, 2011, which claims benefit of priority to U.S. Provisional Application Ser. No. 61/349,555, filed May 28, 2010. Each of these applications is incorporated herein by reference.

FIELD OF THE INVENTION

The present invention relates in general to the field of peptidomimetics and specifically to compositions of matter, kits, methods of making oligo-benzamide peptidomimetic compounds, and methods of their use in medical indications such as cancer.

BACKGROUND OF THE INVENTION

Androgen receptor (AR) signaling is essential for prostate cancer development, growth, and progression at all stages of disease. AR signaling occurs via both genomic and non-genomic pathways and is mediated by AR interaction with cofactors including a scaffolding protein PELP-1. Recently, the inventors have discovered that PELP-1 interacts with AR and that this interaction is critical for both AR-mediated genomic and non-genomic signaling. Thus, they hypothesize that disruption of the interaction of AR and PELP-1 may influence AR-signaling.

Peptidomimetics (also known as peptide mimetics) are small organic molecules that do not possess the peptide backbone structure, however still retain a capability to interact with the same target protein by arranging essential functional groups (i.e., pharmacophores) in a required three-dimensional pattern complimentary to a binding pocket in the protein. Since peptides and proteins adopt and utilize secondary structures (e.g., α-helix, β-sheet, and reverse turns) to make their global shapes and to recognize their binding partners, rational design of secondary structure mimetics is an important strategy in developing small molecule modulators for protein complex formation, compared to conventional high-throughput screening of a chemical library.

At present, no compounds are known that specifically inhibit the interaction with PELP-1 and AR. The identification of such compounds, and assessment of their use as anti-cancer agents, would therefore be highly desireable.

SUMMARY OF THE INVENTION

The present inventors recognized a need for stable small molecules possessing the capability to modulate AR signaling without the limitations of the peptide structure. The present invention provides a class of small molecules that are stable and capable of interacting with molecules involved in AR signaling but lacking the limitations of the peptide structure. These small molecules include α-helix mimetics that represent helical segments in the target molecules.

The oligo-benzamide peptidomimetic compound includes at least two optionally substituted benzamides, with each of the substituted benzamides having one substituent on a benzene ring. The oligo-benzamide peptidomimetic compound modulates protein-protein, protein-peptide, or protein-drug interaction to exert a variety of physiological consequences.

Another embodiment of the present invention is the addition of a third optionally substituted benzamide connected to one of the at least two optionally substituted benzamides, and the third optionally substituted benzamide may include one substituent on a benzene ring. The present invention also provides an oligo-benzamide peptidomimetic compound that includes at least two optionally substituted benzamides with one substituent on a benzene ring.

The present invention provides, in one aspect, a compound of formulas (A) or (B):

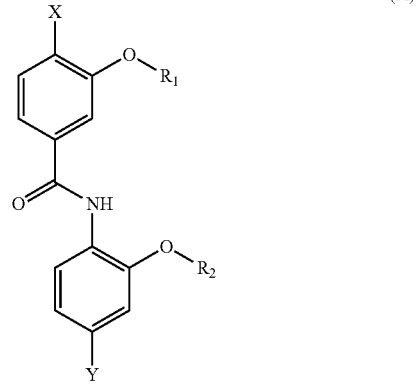

(A)

wherein:
R$_1$ and R$_2$ are each independently C$_1$-C$_{10}$ alkyl, C$_1$-C$_{10}$ alkenyl, C$_1$-C$_{10}$ alkynyl, C$_1$-C$_{15}$ optionally substituted arylalkyl, —(CH$_2$)$_n$—COOR, —(CH$_2$)$_n$—CONRR', —(CH$_2$)$_n$—NRR', —(CH$_2$)$_n$—NH(C=NH)NRR', —(CH$_2$)$_n$—NRCOR', —(CH$_2$)$_n$—NRCOOR', —(CH$_2$)$_n$—OR, —(CH$_2$)$_n$—SR, —(CH$_2$)$_n$—SO$_m$R, —(CH$_2$)$_n$—PO$_m$R, wherein n and m may be any number between 0 and 6 and R and R' may be a H, C$_1$-C$_{10}$ alkyl, C$_1$-C$_{10}$ alkenyl, C$_1$-C$_{10}$ alkynyl, or C$_1$-C$_{15}$ optionally substituted arylalkyl group;

X is —NO$_2$ or —NHC(O)CH$_2$R$_3$, wherein R$_3$ is —NO$_2$, —Z, C$_1$-C$_{10}$ alkyl, C$_1$-C$_{10}$ alkenyl, C$_1$-C$_{10}$ alkynyl, or C$_1$-C$_{15}$ arylalkyl, each of which is optionally substituted with —COOR, —CONRR', —NRR', —NH(C=NH)NRR', —NRCOR', —NRCOOR', —OR, —SR, —SO$_n$R, or —PO$_n$R, wherein n may be any number between 0 and 6 and R and R' may be a H, C$_1$-C$_{10}$ alkyl, C$_1$-C$_{10}$ alkenyl, C$_1$-C$_{10}$ alkynyl, or C$_1$-C$_{15}$ optionally substituted arylalkyl group, and wherein Z is:

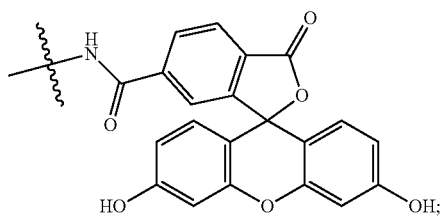

and
Y is —(CH$_2$)$_n$COOR$_4$, —(CH$_2$)$_n$CONR$_4$R$_5$, —(CH$_2$)$_n$NR$_4$R$_5$, —(CH$_2$)$_n$—NR$_4$R$_5$, —(CH$_2$)$_n$—NH(C=NH)NR$_4$R$_5$, —(CH$_2$)$_n$—NR$_4$COR$_5$, —(CH$_2$)$_n$—NR$_4$COOR$_5$, —(CH$_2$)$_n$—OR$_4$, —(CH$_2$)$_n$—SR$_4$, —(CH$_2$)$_n$—SO$_m$R$_4$, —(CH$_2$)$_n$—PO$_m$R$_4$, wherein n and m may be any number between 0 and 6, $R_4$ and $R_5$ are independently selected from —H, $C_1$-$C_{10}$ alkyl, $C_1$-$C_{10}$ alkenyl, $C_1$-$C_{10}$ alkynyl, or $C_1$-$C_{15}$ optionally substituted arylalkyl group; or

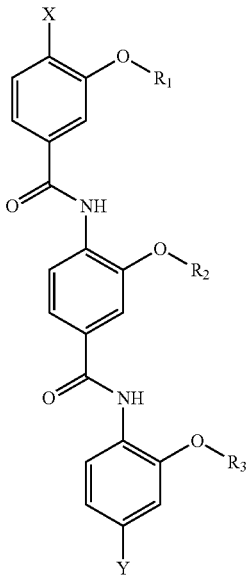

(B)

wherein:

$R_1$, $R_2$ and $R_3$ are each independently $C_1$-$C_{10}$ alkyl, $C_1$-$C_{10}$ alkenyl, $C_1$-$C_{10}$ alkynyl, $C_1$-$C_{15}$ optionally substituted arylalkyl, —(CH$_2$)$_n$—COOR, —(CH$_2$)$_n$—CONRR', —(CH$_2$)$_n$—NRR', —(CH$_2$)$_n$—NH(C=NH)NRR', —(CH$_2$)$_n$—NRCOR', —(CH$_2$)$_n$—NRCOOR', —(CH$_2$)$_n$—OR, —(CH$_2$)$_n$—SR, —(CH$_2$)$_n$—SO$_m$R, —(CH$_2$)$_n$—PO$_m$R, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl group or

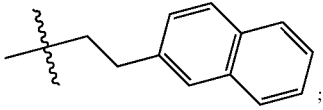;

X' is —NO$_2$ or —NHC(O)CH$_2$R$_3$, wherein R$_3$ is —NO$_2$, —Z', $C_1$-$C_{10}$ alkyl, $C_1$-$C_{10}$ alkenyl, $C_1$-$C_{10}$ alkynyl, or $C_1$-$C_{15}$ arylalkyl, each of which is optionally substituted with —COOR, —CONRR', —NRR', —NH(C=NH)NRR', —NRCOR', —NRCOOR', —OR, —SR, —SO$_n$R, or —PO$_n$R, wherein n may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl group, and wherein Z' is:

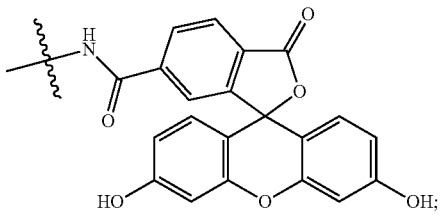

and

Y' is —(CH$_2$)$_n$COOR$_4$, —(CH$_2$)$_n$CONR$_4$R$_5$, —(CH$_2$)$_n$NR$_4$R$_5$, —(CH$_2$)$_n$—NR$_4$R$_5$, —(CH$_2$)$_n$—NH(C=NH)NR$_4$R$_5$, —(CH$_2$)$_n$—NR$_4$COR$_5$, —(CH$_2$)$_n$—NR$_4$COOR$_5$, —(CH$_2$)$_n$—OR$_4$, —(CH$_2$)$_n$—SR$_4$, —(CH$_2$)$_n$—SO$_m$R$_4$, —(CH$_2$)$_n$—PO$_m$R$_4$, wherein n and m may be any number between 0 and 6, $R_4$ and $R_5$ are independently selected from —H, $C_1$-$C_{10}$ alkyl, $C_1$-$C_{10}$ alkenyl, $C_1$-$C_{10}$ alkynyl, or $C_1$-$C_{15}$ optionally substituted arylalkyl group.

In particular, X may be —NO$_2$, and may further be defined as:

$R_1$ and $R_2$ are $C_1$-$C_{10}$ alkyl, $C_1$-$C_{10}$ alkenyl, or $C_1$-$C_{10}$ alkynyl;

$R_1$ and $R_2$ are optionally substituted $C_1$-$C_{15}$ arylalkyl;

$R_1$ and $R_2$ are —(CH$_2$)$_n$—NRR' or —(CH$_2$)$_n$—NH(C=NH)NRR' groups, wherein n may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$ and $R_2$ are —(CH$_2$)$_n$—COOR, —(CH$_2$)$_n$—CONRR', —(CH$_2$)$_n$—NRCOR', —(CH$_2$)$_n$—NRCOOR', —(CH$_2$)$_n$—SO$_m$R, —(CH$_2$)$_n$—PO$_m$R, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$ and $R_2$ are —(CH$_2$)$_n$—OR, —(CH$_2$)$_n$—SR, wherein R may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$ is $C_1$-$C_{15}$ optionally substituted arylalkyl, and $R_2$ is $C_1$-$C_{10}$ alkyl, $C_1$-$C_{10}$ alkenyl, or $C_1$-$C_{10}$ alkynyl;

$R_1$ is $C_1$-$C_{10}$ alkyl, $C_1$-$C_{10}$ alkenyl, or $C_1$-$C_{10}$ alkynyl, and $R_2$ is $C_1$-$C_{15}$ optionally substituted arylalkyl;

$R_1$ is —(CH$_2$)$_n$—NRR' or —(CH$_2$)$_n$—NH(C=NH)NRR', and $R_2$ is —(CH$_2$)$_n$—COOR, —(CH$_2$)$_n$—SO$_m$R, —(CH$_2$)$_n$—PO$_m$R, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl group;

$R_1$ is —(CH$_2$)$_n$—COOR, —(CH$_2$)$_n$—SO$_m$R, —(CH$_2$)$_n$—PO$_m$R, and $R_2$ is —(CH$_2$)$_n$—NRR' or —(CH$_2$)$_n$—NH(C=NH)NRR', wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl group; or $R_1$ or $R_2$ are independently selected from isopropyl, isobutyl, n-butyl, sec-butyl or n-pentyl.

In particular, X' may be —NO$_2$, and may further be defined as:

$R_1$, $R_2$, and $R_3$ are $C_1$-$C_{10}$ alkyl, $C_1$-$C_{10}$ alkenyl, or $C_1$-$C_{10}$ alkynyl;

$R_1$, $R_2$, and $R_3$ are optionally substituted $C_1$-$C_{15}$ arylalkyl;

$R_1$, $R_2$, and $R_3$ are —(CH$_2$)$_n$—NRR' or —(CH$_2$)$_n$—NH(C=NH)NRR' groups, wherein n may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$, $R_2$, and $R_3$ are —(CH$_2$)$_n$—COOR, —(CH$_2$)$_n$—CONRR', —(CH$_2$)$_n$—NRCOR', —(CH$_2$)$_n$—NRCOOR', —(CH$_2$)$_n$—SO$_m$R, —(CH$_2$)$_n$—PO$_m$R, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$, $R_2$, and $R_3$ are —(CH$_2$)$_n$—OR, —(CH$_2$)$_n$—SR, wherein R may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$ is $C_1$-$C_{15}$ optionally substituted arylalkyl, and $R_2$ and $R_3$ are $C_1$-$C_{10}$ alkyl, $C_1$-$C_{10}$ alkenyl, or $C_1$-$C_{10}$ alkynyl;

$R_1$ and $R_2$ are $C_1$-$C_{10}$ alkyl, $C_1$-$C_{10}$ alkenyl, or $C_1$-$C_{10}$ alkynyl, and $R_3$ is $C_1$-$C_{15}$ optionally substituted arylalkyl;

$R_1$ is $C_1$-$C_{10}$ alkyl, $C_1$-$C_{10}$ alkenyl, or $C_1$-$C_{10}$ alkynyl, and $R_2$ and $R_3$ are $C_1$-$C_{15}$ optionally substituted arylalkyl;

$R_1$ and $R_2$ are $C_1$-$C_{15}$ optionally substituted arylalkyl, and $R_3$ is $C_1$-$C_{10}$ alkyl, $C_1$-$C_{10}$ alkenyl, or $C_1$-$C_{10}$ alkynyl;

$R_1$ and $R_3$ are $C_1$-$C_{10}$ alkyl, $C_1$-$C_{10}$ alkenyl, or $C_1$-$C_{10}$ alkynyl, and $R_2$ is $C_1$-$C_{15}$ optionally substituted arylalkyl;

$R_1$ and $R_3$ are $C_1$-$C_{15}$ optionally substituted arylalkyl, and $R_2$ is $C_1$-$C_{10}$ alkyl, $C_1$-$C_{10}$ alkenyl, or $C_1$-$C_{10}$ alkynyl;

$R_1$ and $R_2$ are —$(CH_2)_n$—NRR' or —$(CH_2)_n$—NH(C=NH)NRR', and $R_3$ is $C_1$-$C_{10}$ alkyl, $C_1$-$C_{10}$ alkenyl, or $C_1$-$C_{10}$ alkynyl, wherein n may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$ is $C_1$-$C_{10}$ alkyl, $C_1$-$C_{10}$ alkenyl, or $C_1$-$C_{10}$ alkynyl, and $R_2$ and $R_3$ are —$(CH_2)_n$—NRR' or —$(CH_2)_n$—NH(C=NH)NRR', wherein n may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$ and $R_2$ are —$(CH_2)_n$—NRR' or —$(CH_2)_n$—NH(C=NH)NRR', and $R_3$ is $C_1$-$C_{15}$ optionally substituted arylalkyl, wherein n may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$ is $C_1$-$C_{15}$ optionally substituted arylalkyl, and $R_2$ and $R_3$ are —$(CH_2)_n$—NRR' or —$(CH_2)_n$—NH(C=NH)NRR', wherein n may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$ and $R_2$ are —$(CH_2)_n$—COOR, —$(CH_2)_n$—CONRR', —$(CH_2)_n$—NRCOR', —$(CH_2)_n$—NRCOOR', —$(CH_2)_n$—SO$_m$R, —$(CH_2)_n$—PO$_m$R, and $R_3$ is $C_1$-$C_{10}$ alkyl, $C_1$-$C_{10}$ alkenyl, or $C_1$-$C_{10}$ alkynyl, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$ is $C_1$-$C_{10}$ alkyl, $C_1$-$C_{10}$ alkenyl, or $C_1$-$C_{10}$ alkynyl, and $R_2$ and $R_3$ are —$(CH_2)_n$—COOR, —$(CH_2)_n$—CONRR', —$(CH_2)_n$—NRCOR', —$(CH_2)_n$—NRCOOR', —$(CH_2)_n$—SO$_m$R, —$(CH_2)_n$—PO$_m$R, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$ and $R_2$ are —$(CH_2)_n$—COOR, —$(CH_2)_n$—CONRR', —$(CH_2)_n$—NRCOR', —$(CH_2)_n$—NRCOOR', —$(CH_2)_n$—SO$_m$R, —$(CH_2)_n$—PO$_m$R, and $R_3$ is $C_1$-$C_{15}$ optionally substituted arylalkyl, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$ is $C_1$-$C_{15}$ optionally substituted arylalkyl, and $R_2$ and $R_3$ are —$(CH_2)_n$—COOR, —$(CH_2)_n$—CONRR', —$(CH_2)_n$—NRCOR', —$(CH_2)_n$—NRCOOR', —$(CH_2)_n$—SO$_m$R, —$(CH_2)_n$—PO$_m$R, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$ and $R_3$ are —$(CH_2)_n$—NRR' or —$(CH_2)_n$—NH(C=NH)NRR', and $R_2$ is —$(CH_2)_n$—COOR, —$(CH_2)_n$—CONRR', —$(CH_2)_n$—NRCOR', —$(CH_2)_n$—NRCOOR', —$(CH_2)_n$—SO$_m$R, —$(CH_2)_n$—PO$_m$R, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$ and $R_3$ are —$(CH_2)_n$—COOR, —$(CH_2)_n$—CONRR', —$(CH_2)_n$—NRCOR', —$(CH_2)_n$—NRCOOR', —$(CH_2)_n$—SO$_m$R, —$(CH_2)_n$—PO$_m$R, and $R_2$ is —$(CH_2)_n$—NRR' or —$(CH_2)_n$—NH(C=NH)NRR', wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl;

$R_1$, $R_2$ or $R_3$ are independently selected from isopropyl, isobutyl, n-butyl, sec-butyl or n-pentyl; or $R_1$, $R_2$ or $R_3$ is:

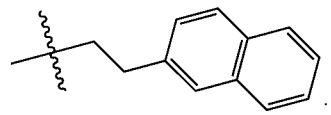

Alternatively, X may be —NHC(O)CH$_2$R$_3$ and R$_3$ may be —NH$_2$ or $C_1$-$C_{10}$ alkyl, optionally substituted with —COOH. Alternatively, X' may be —NHC(O)CH$_2$NH$_2$.

Y or Y' may in particular be —NH$_2$.

Specific compound according to the invention include:

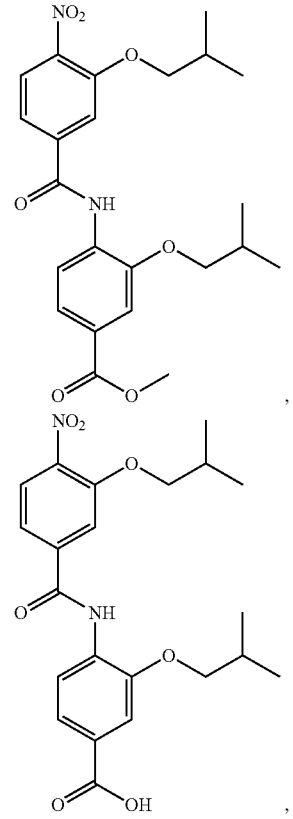

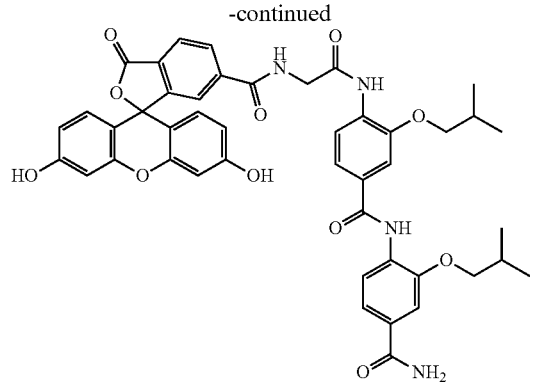
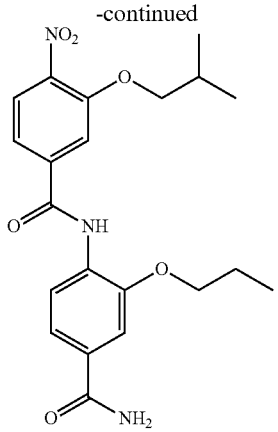
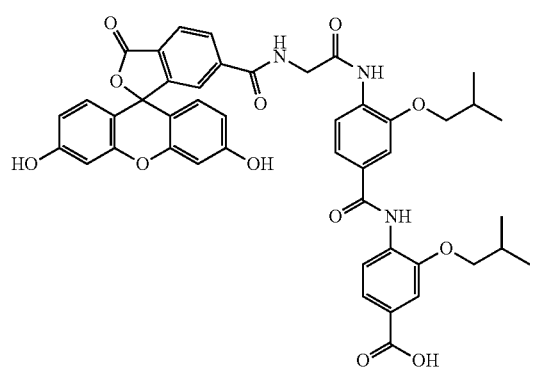
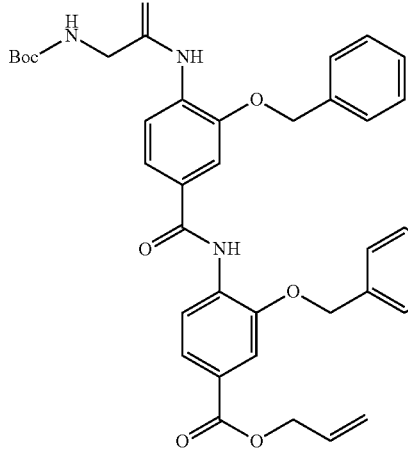
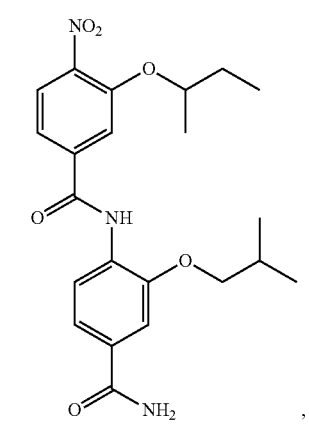
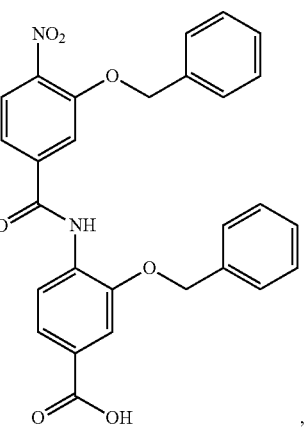
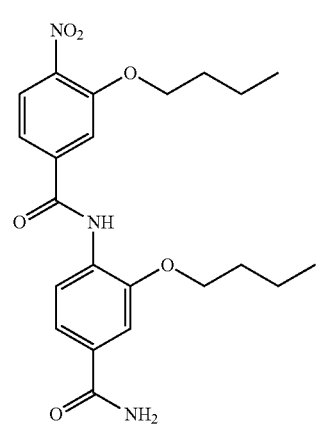
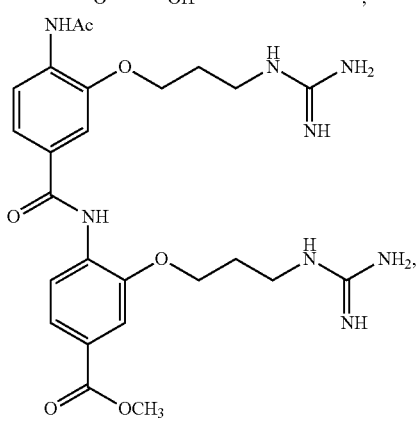

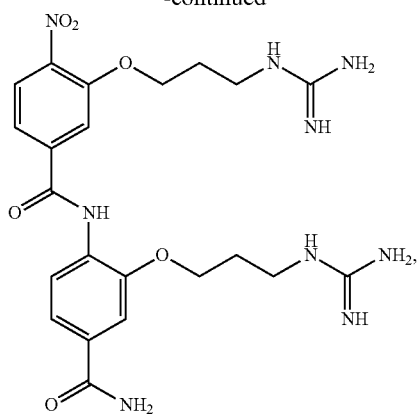
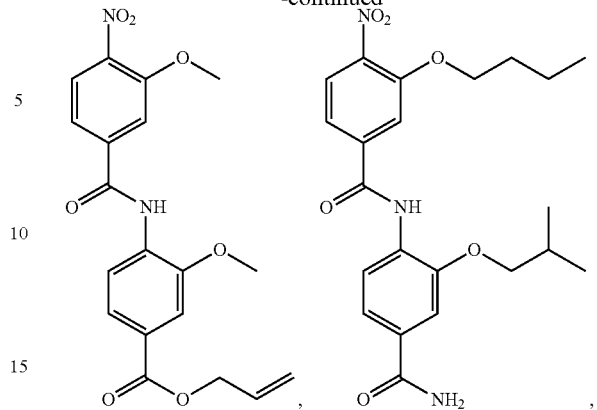
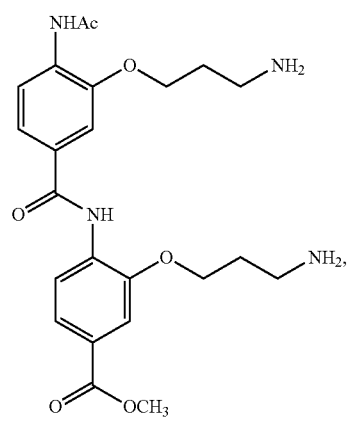
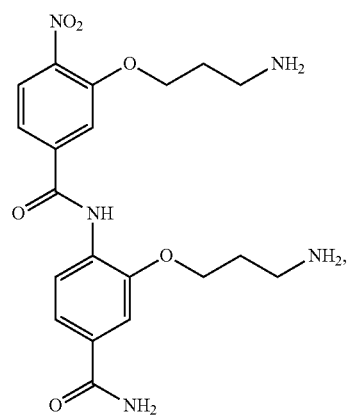
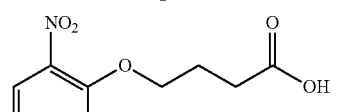
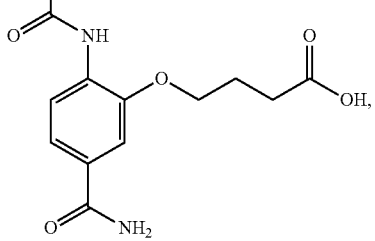
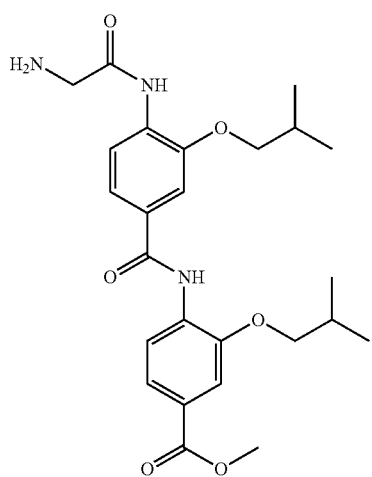

| 11 | 12 |
|---|---|
| -continued | -continued |
| 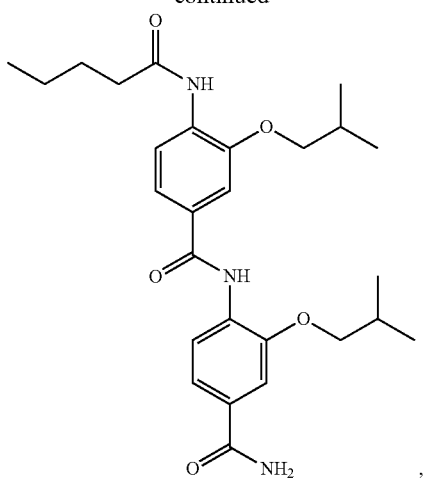 | 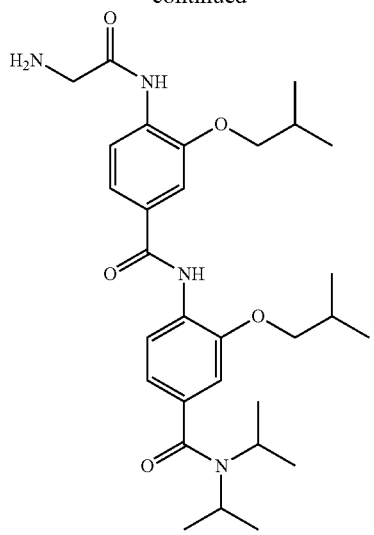 |
| 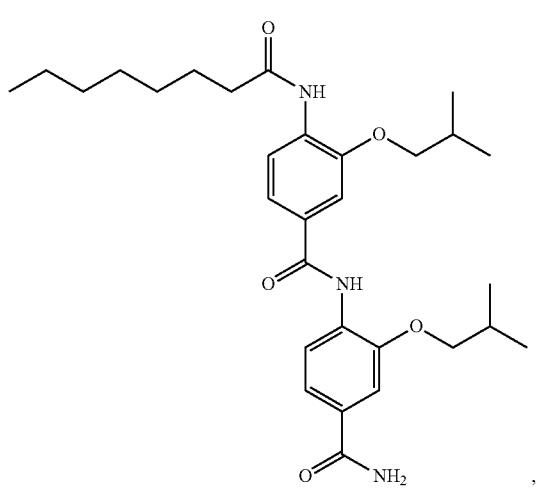 | 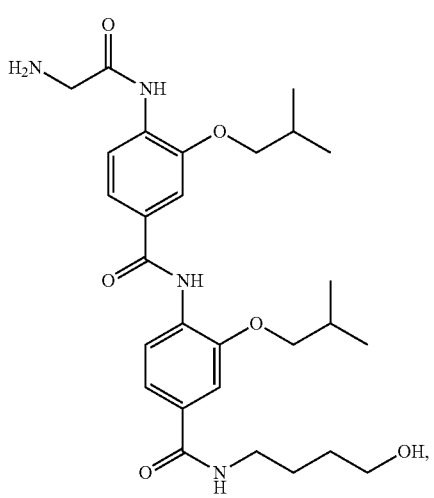 |
| 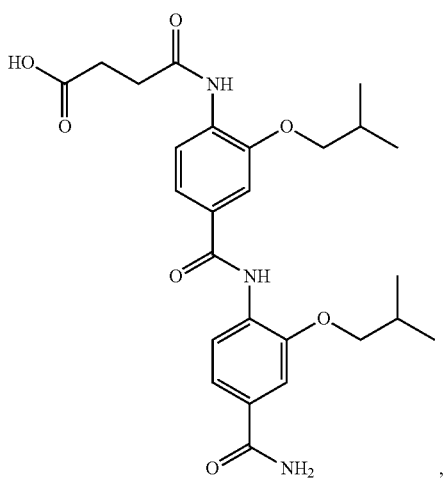 | 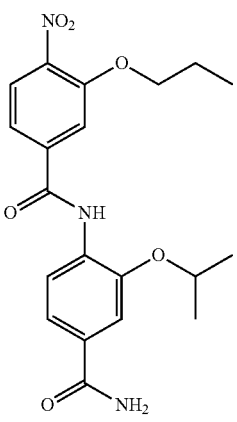 |

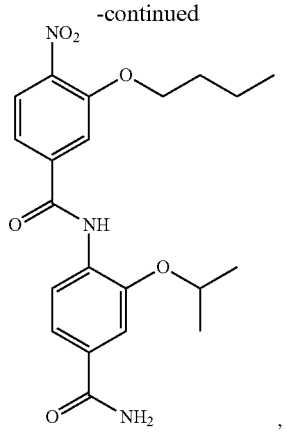
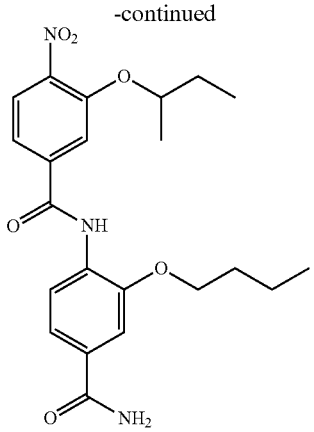
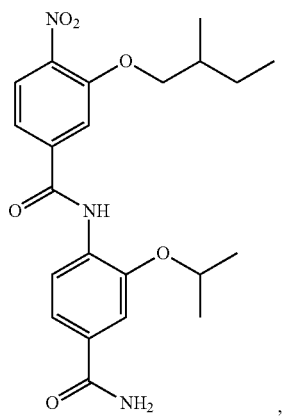
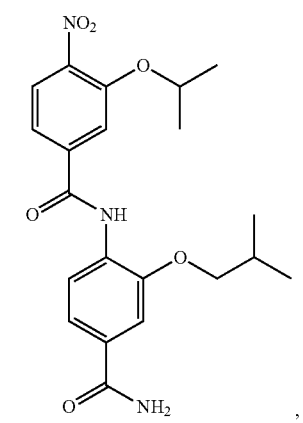
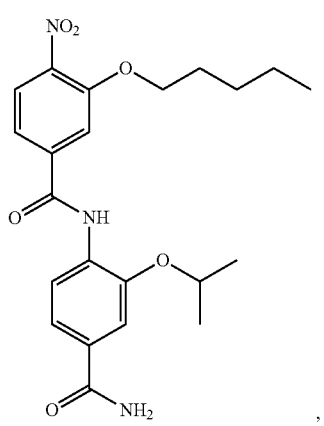
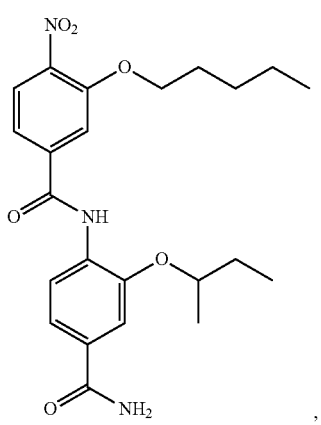
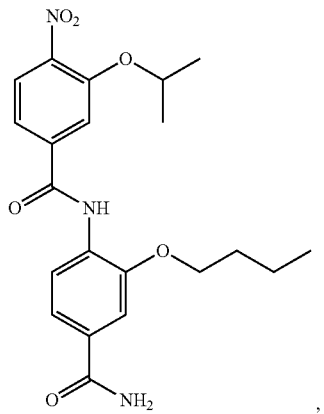
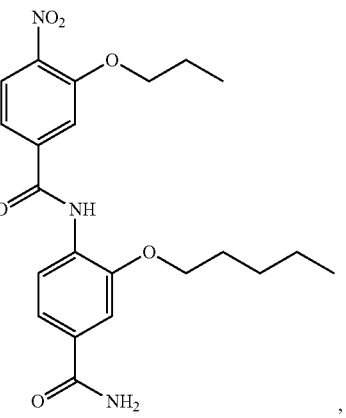

15
-continued
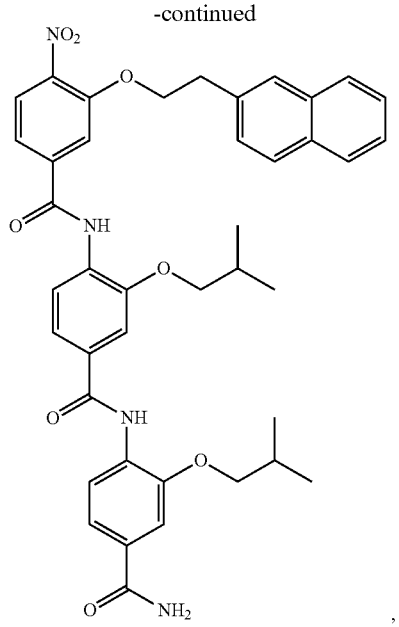
,
16
-continued
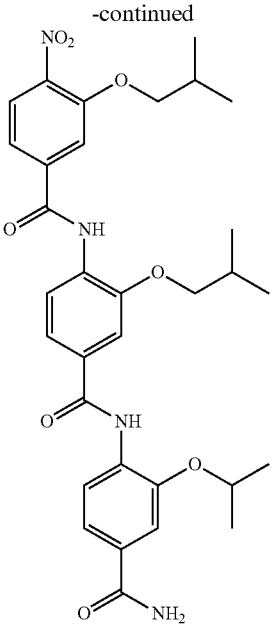
,
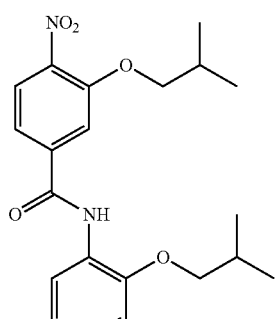
,
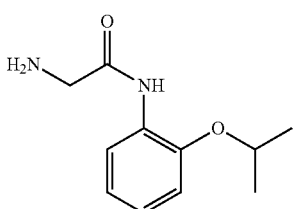
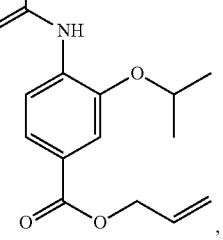
, 17
-continued
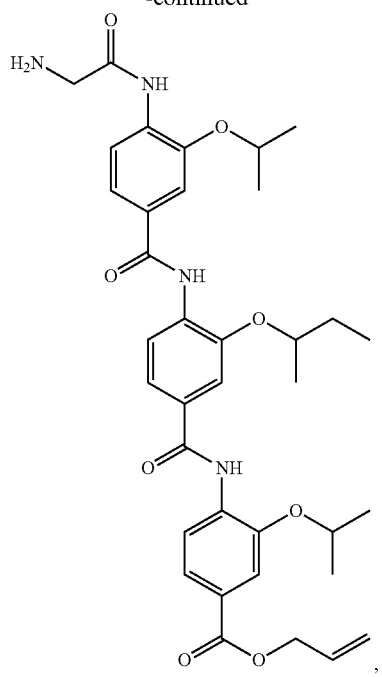
18
-continued
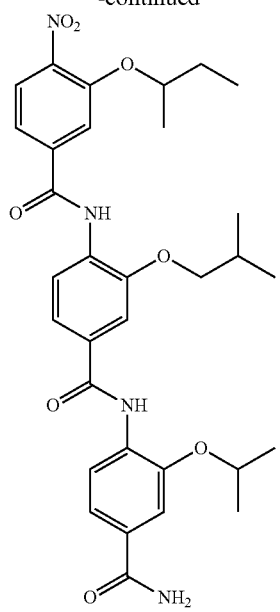
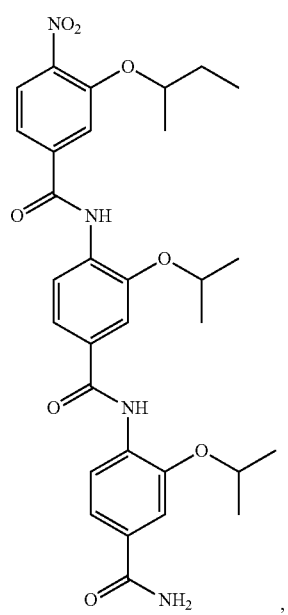
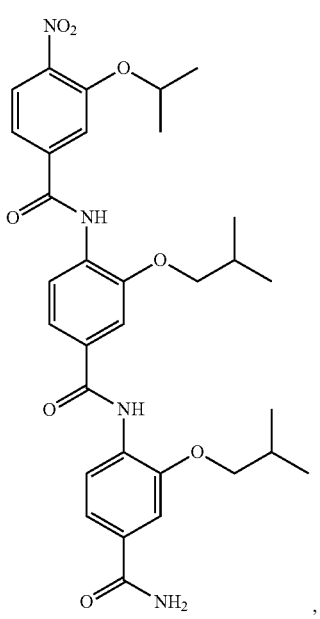

19
-continued
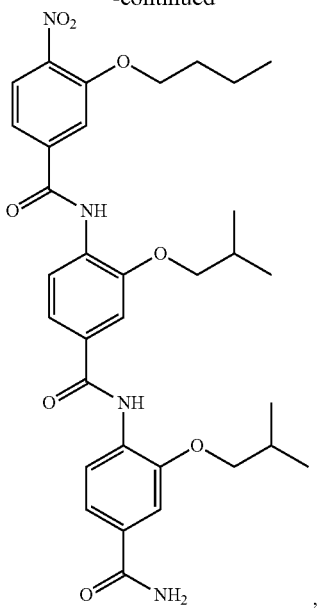
20
-continued
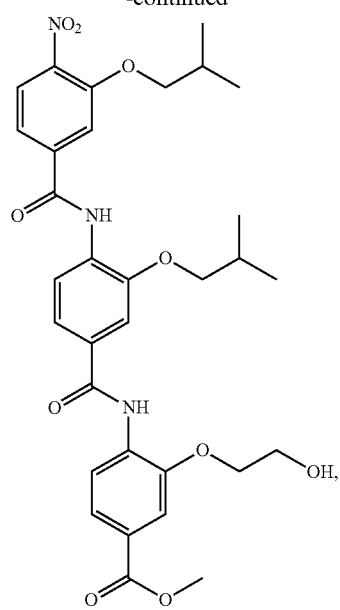
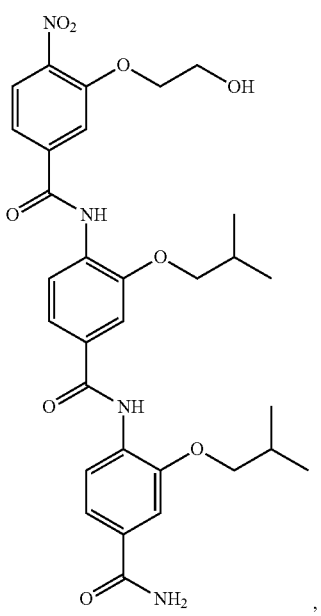
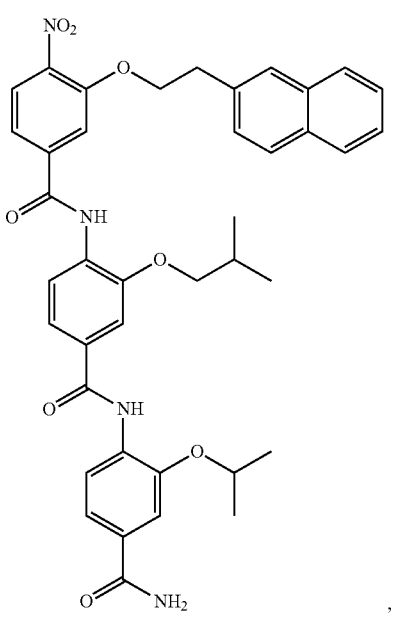

21
-continued
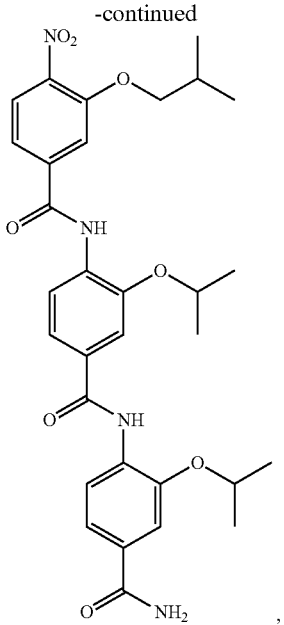
,
22
-continued
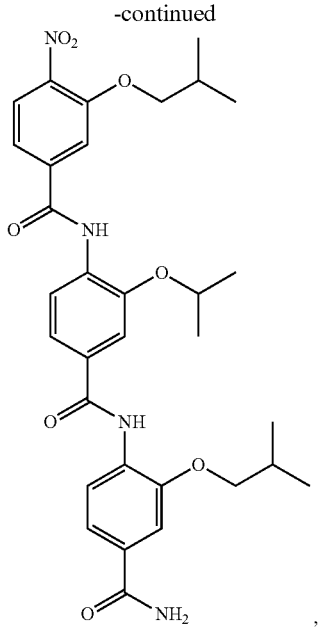
,
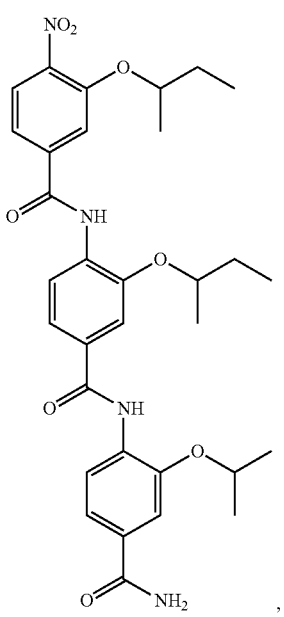
,
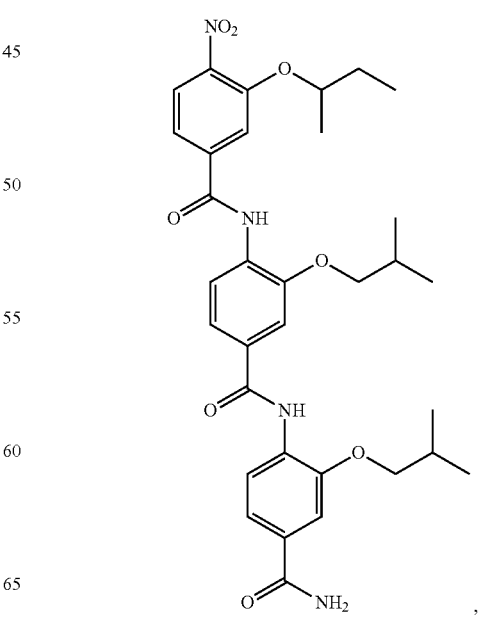
,

23
-continued

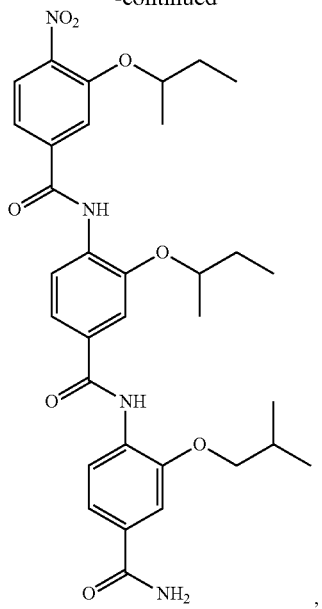

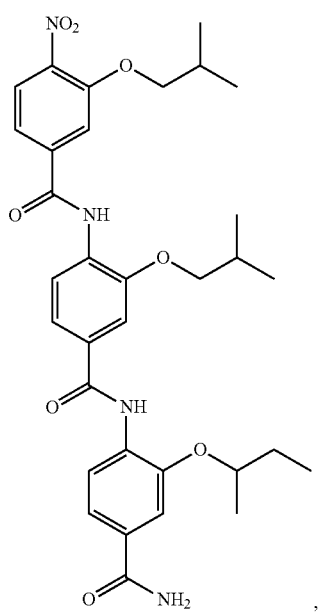

24
-continued

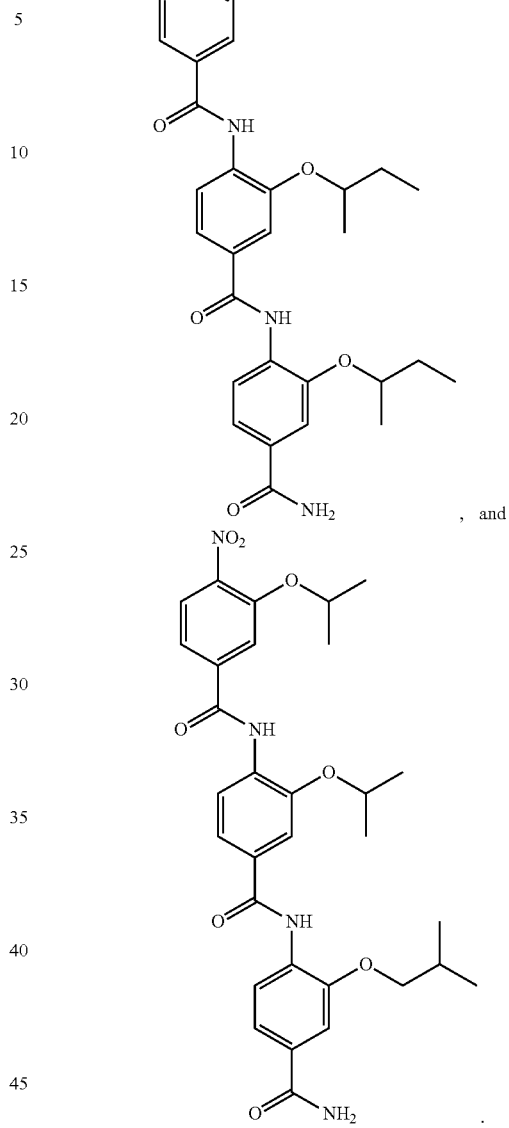

Also provided is a pharmaceutical composition comprising any of the compounds described above, dispersed in a pharmaceutically acceptable carrier, buffer or diluent.

In another embodiment, there is provided a method of inhibiting a androgen receptor (AR)-positive tumor cell in a subject comprising administering to said subject a therapeutically sufficient amount of an oligo-benzamide peptidomimetic compound as described above.

The AR-positive tumor cell may be a carcinoma cell, a leukemia cell or a myeloma cell. The carcinoma cell may be a prostate or breast carcinoma cell. The peptidomimetic may be fused to a cell delivery domain. Administering may comprise intravenous, intra-arterial, intra-tumoral, subcutaneous, topical or intraperitoneal administration, or local, regional, systemic, or continual administration. Inhibiting may comprise inducing growth arrest of said tumor cell, apoptosis of said tumor cell and/or necrosis of a tumor tissue comprising said tumor cell.

Administering may further comprise providing a second anti-cancer therapy, such as surgery, chemotherapy, radiotherapy, hormonal therapy, toxin therapy, immunotherapy, and cryotherapy. The may be provided prior to administration of said compound, after administration of said compound, or at the same time as said compound.

The subject may be a human. The compound may be is administered at about 0.1 to 100 mg/kg or at about 1 to about 50 mg/kg, or at about 10 mg/kg. The compound may be administered daily, for example, for 7 days, 2 weeks, 3 weeks, 4 weeks, one month, 6 weeks, 8 weeks, two months, 12 weeks, or 3 months. The compound may be administered weekly, for example, for 2 weeks, 3 weeks, 4 weeks, 6 weeks, 8 weeks, 10 weeks, or 12 weeks.

The method may further comprise assessing AR-driven gene expression in said tumor cell of said subject prior to administering said compound, or further comprise assessing AR-driven gene expression in said tumor cell of said subject after administering said compound.

The present invention provides a pharmaceutical composition that includes a therapeutically effective amount of an oligo-benzamide compound or a salt, a solvate, or a derivative thereof having an oligo-benzamide compound and one or more pharmaceutically acceptable carriers. The oligo-benzamide compound includes two or three optionally substituted benzamides (e.g., substituted and/or non-substituted benzamides) and one substituent groups attached to each of the substituted benzamides individually by a chemical bond including ether, thioether, amine, amide, carbamate, urea, and carbon-carbon (single, double, and triple) bonds.

The use of the word "a" or "an" when used in conjunction with the term "comprising" in the claims and/or the specification may mean "one," but it is also consistent with the meaning of "one or more," "at least one," and "one or more than one."

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. The skilled artisan will understand that typically there is no limit on the number of items or terms in any combination, unless otherwise apparent from the context.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements. It is contemplated that any method or composition described herein can be implemented with respect to any other method or composition described herein.

BRIEF DESCRIPTION OF THE DRAWINGS

For a more complete understanding of the features and advantages of the present invention, reference is now made to the detailed description of the invention along with the accompanying figures and in which:

FIGS. 2A & 2B show the crystal structures of wild-type AR ligand-binding domain with DHT as a front view (FIG. 2A) and as a ligand view (FIG. 2B). FIG. 2C shows the sequence of the AR domain noting the H3, H4, H5, and H12 regions. Helices 3, 4, and 12 are highlighted which represent the activation function 2 (AF2) region. The interaction is with the "nuclear receptor box" or "LXXLL motif". FIGS. 2D & 2E show the crystal structure of the LXXLL motif-bound AF-2 interface for human AR. The ball and stick model shows the key residues of one of the binding pockets around helices H3, H4, and H12. FIG. 2E shows the space filling model of this binding pocket. The LXXLL peptide has the sequence: SSRGLLWDLLTKDSR with a $K_d$ of 1.8 µM. The flanking residues were highly disordered with 2 residues at N and 1 residue at C visible in the crystal structure. In the crystal structure, Met734 causes displace of Leu (+1) away from H12 towards H3. The Lys720 interacts with the backbone and Glu897 interacts with the backbone through a water molecule. Further information related to these crystal structures can be found in PLoS Biology, 2:e274, 2004.

FIGS. 4A-F. (FIG. 4A) Chemical structure of the bis-benzamide (D2). (FIG. 4B) the lowest-energy conformation of D2. (FIG. 4C) the stereoview of the superimposition of D2 on a helical turn. (FIG. 4D) the stereoview of the superimposition of D2 on PELP1 LXXLL motif and a helical PELP1 LXXLL motif; (FIG. 4E) stability of D2 in culture showing a single peak on the HPLC; (FIG. 4F) stability of D2 over time upon incubation with cell lysates at 37° C. for days as specified.

(FIG. 7A) Model depicts the proposed role for D2 in disrupting the interaction between AR and NR Box proteins such as Hsp27 and PELP1. (FIG. 7B) Effect of increasing concentration of D2 on complex formation between AR and NR Box proteins such as Hsp27 and PELP1, as shown for immunoprecipitation with AR (top panel) and with PELP1 (bottom panel). Input lysates are shown at the bottom. (FIG. 7C) Rescue of D2-induced suppression of AR-PELP1 complex formation: Following transient transfection with increasing concentrations of AR (left panel) or increasing concentration of PELP1 (right panel), LnCAP cells were treated with 10 nM DHT for 24 hours following preincubation with D2 or control D1. Extracts were immunoprecipitated with AR and immunoblotted with PELP1, AR or importin.

DETAILED DESCRIPTION OF THE INVENTION

Figure 1:
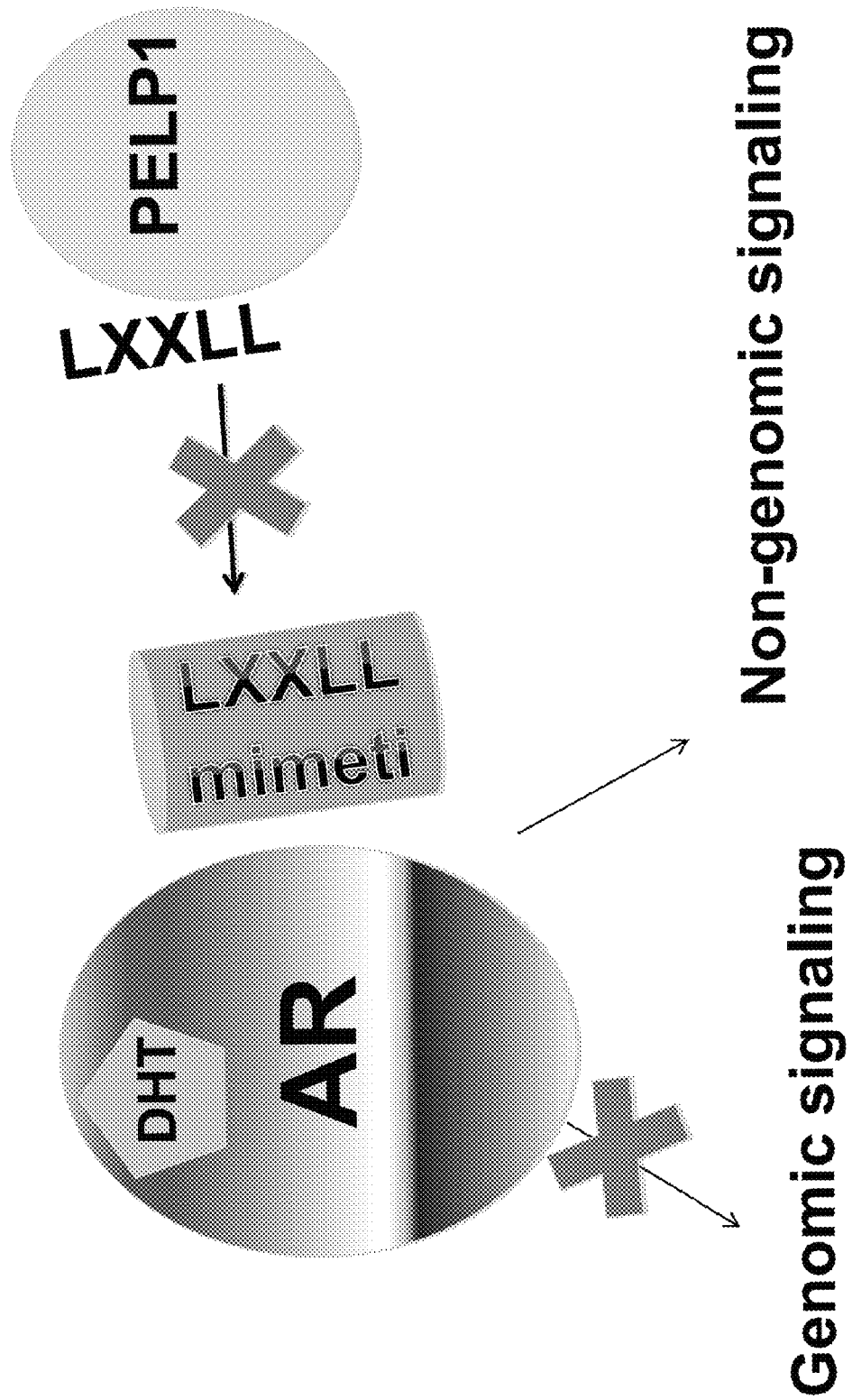
FIG. 1. Blocking AR PELP1 interaction should block AR-mediated genomic signaling and may affect AR-mediated non-genomic signaling.

As discussed above, the interaction between PELP-1 and AR is believed to play a role in carcinogenesis. Since PELP-1 is thought to bind AR via its LXXLL motif, the inventors sought to develop bis-benzamide-based peptidomimetics by a rational design approach in order to competitively disrupt AR and PELP-1 interaction.

The bis-benzamide contains two alkyl groups ($R_1$-2) that correspond to the i and i+4 positions of a helix. The bis-benzamide designated D2 has two isobutyl groups and emulates the side chain groups of two leucines at the i and i+4 positions of the LXXLL motif and presents leucines spaced a helical turn apart. Prior attempts to target the LXXLL motif with peptides and peptidomimetics have not been successful as the spacing between the leucines has not been optimal for functional activity in vivo.

The peptidomimetics of the present invention are non-toxic under in vitro and in vivo conditions. The development of these peptidomimetics represents a quantum leap in the development of a drug to target AR signaling. Interestingly, these synthetic molecules prevent androgen-induced translocation of AR to the nucleus and represents perhaps one of the first instances of peptidomimetic agents that block AR nuclear translocation. In addition to improvements in the helical face and presentation of the leucines, the inventors have proven efficacy of this system against prostate cancer cell proliferation both in vitro and in vivo. Thus, in contrast to existing technology, the inventors have developed and tested an active peptidomimetic against prostate cancer and other androgen receptor involved cancers.

A particular peptidomimetic, D2, is non-toxic to prostate cancer cells, enters the prostate cancer cells and selectively targets androgen receptor signaling via the genomic pathway. They have shown that this synthetic peptidomimetic D2 is capable of blocking AR-PELP-1 interaction, nuclear translocation of AR, AR mediated genomic signaling as well as DHT-mediated proliferation of prostate cancer cells in vitro. The $IC_{50}$ of D2 appears to be around 40 nM. The effect of the D2 peptidomimetic appears to be specific to blocking AR-PELP-1 interaction, as overexpression of AR or PELP-1 may overcome D2-mediated blockade. Finally, the inventors have shown that intratumoral or intraperitoneal administration of D2 can significantly abrogate the growth of prostate cancer cells implanted subcutaneously into nude mice. In comparison, administration of either control peptidomimetics or control soluent has no effect on the growth of prostate cancer cells in vitro or in vivo. In addition, the inventors have generated and tested hundreds of variants of D2 and have identified related peptidomimetics with similar or equivalent potency.

These findings are exciting and represent a potentially viable method to target AR signaling pathways in prostate cancer. These peptidomimetics have advantages of both peptides (e.g., high efficacy and selectivity, low side effects) and small organic molecules (e.g., high enzyme stability, oral bioavailability, effective cell permeability). In addition, the novel platform using the peptidomimetics with a rigid oligo-benzamide backbone allows the presentation of selected amino acid side chains in the proper helical structure that is critical for optimal AR interactions.

I. Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "alkyl" denotes branched or unbranched hydrocarbon chains, having between about 1-20 carbons, with "lower alkyl" denoting branched or unbranched hydrocarbon chains, having between about 1-10 carbons. Non-limiting examples include methyl, ethyl, propyl, n-propyl, isopropyl, butyl, n-butyl, sec-butyl, isobutyl, t-butyl, 1-methylpropyl, pentyl, isopentyl, sec-pentyl, 2-methylpentyl, hexyl, heptyl, octyl, nonyl, decyl, octadecyl and so on. Alkyl includes cycloalkyl, such as cyclopropyl, cyclobutyl, cyclopentyl, and cyclohexyl. If not otherwise specified, these groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino, and the like to form alkyl groups such as trifluoro methyl, 3-hydroxyhexyl, 2-carboxypropyl, 2-fluoroethyl, carboxymethyl, cyanobutyl and the like.

As used herein, the term "aryl" denotes a chain of carbon atoms which form at least one aromatic ring having between about 4-20 carbon atoms, such as phenyl, naphthyl, biphenyl, anthracenyl, pyrenyl, tetrahydronaphthyl, and so on, any of which may be optionally substituted. Aryl also includes arylalkyl groups such as benzyl, phenethyl, and phenylpropyl. Aryl includes a ring system containing an optionally substituted 5 or 6-membered carbocyclic aromatic ring, said system may be bicyclic, polycyclic, bridge, and/or fused. The system may include rings that are aromatic, or partially or completely saturated. Examples of ring systems include phenyl, naphtyl, biphenyl, anthracenyl, pyrenyl, imidazolyl, triazolyl, tetraazolyl, oxazolyl, thiophenyl, pyridyl, pyrrolyl, furanyl, quinolyl, quinolinyl, indenyl, pentalenyl, 1,4-dihydronaphthyl, indanyl, benzimidazolyl, benzothiophenyl, indolyl, benzofuranyl, isoquinolinyl, and so on. If not otherwise specified, the group may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, carboxamidyl, alkoxycarbonyl, carbamyl, alkyl, alkenyl, alkynyl, nitro, amino, alkoxy, amido, imino, imido, guanidino, hydrazido, aminoxy, alkoxyamino and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, aminophenyl, amidophenyl, thiazolylphenyl, oxazolylphenyl, imidazolylphenyl, imidazolylmethylphenyl, and the like.

As used herein, the term "alkenyl" includes optionally substituted straight chain and branched hydrocarbons having between about 1-50 carbons as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbons having a mixture of double bonds and triple bonds, such as 2-penten-4-ynyl, are grouped as alkynyls herein. Alkenyl includes cycloalkenyl. Cis and trans or (E) and (Z) forms are included within the invention. If not otherwise specified, these groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino and the like to form alkyl groups such as trifluoro methyl, 3-hydroxyhexyl, 2-carboxypropyl, 2-fluoroethyl, carboxymethyl, cyanobutyl and the like.

As used herein, the term "alkynyl" includes optionally substituted straight chain and branched hydrocarbons having between about 1-50 carbons as above with at least one carbon-carbon triple bond (sp). Alkynyls include ethynyl, propynyls, butynyls, and pentynyls. Hydrocarbons having a mixture of double bonds and triple bonds, such as 2-penten-4-ynyl, are grouped as alkynyls herein. Alkynyl does not include cycloalkynyl. If not otherwise specified, these groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino and the like to form alkyl groups such as trifluoro methyl, 3-hydroxyhexyl, 2-carboxypropyl, 2-fluoroethyl, carboxymethyl, cyanobutyl and the like.

As used herein, the term "alkoxy" includes an optionally substituted straight chain or branched alkyl group having between about 1-50 carbons with a terminal oxygen linking the alkyl group to the rest of the molecule. Alkoxy includes methoxy, ethoxy, propoxy, isopropoxy, butoxy, t-butoxy, pentoxy and so on. If not otherwise specified, alkyoxy also includes any substituted alkyl group connected by an ether linkage, such as aminobutoxy, carboxyethoxy, hydroxyethoxy and so on. "Aminoalkyl", "thioalkyl", and "sulfonylalkyl" are analogous to alkoxy, replacing the terminal oxygen atom of alkoxy with, respectively, NH (or NR), S, and $SO_2$. Heteroalkyl includes alkoxy, aminoalkyl, thioalkyl, and so on.

For any of the groups above, the modifier Cn—Cn' defines both the minimum and maximum number of carbon atoms for the group. For example, "$C_2$-$C_{10}$ alkyl" designates those alkyl groups having from 2 to 10 carbon atoms (e.g., 2, 3, 4, 5, 6, 7, 8, 9, or 10, or any range derivable therein, e.g., 3 to 10 carbon atoms).

As used herein, the term "pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

As used herein, the term "pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts, which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

II. Oligo-Benzamides and Methods of Synthesis

The present invention provides synthetic molecules which present the essential functionalities of corresponding peptide ligands in the proper three dimensional orientation that enables specific protein interactions, leading to either stimulation or inhibition of protein-mediated functions.

Peptidomimetics (also known as peptide mimetics) are small organic compounds which lack the peptide backbone of native peptides. Despite this modification, they still retain an ability to interact with corresponding receptors or enzymes by presenting essential chemical functionalities (i.e., pharmacophores) in characteristic three-dimensional patterns which are complimentary to the target proteins (Marshall, 1993; Ahn et al., 2002). Thereby, peptidomimetics potentially combine the advantages of peptides (e.g., high efficacy and selectivity, low side effects) and small organic molecules (e.g., high enzymatic stability and oral bioavailability).

To mimic α-helices, the present invention provides an oligo-benzamide scaffold that is rigid in structure and place and orient substituents as an α-helix does. Substitution on the rigid tris-benzamide, for instance, allowed easy placement of three functional groups ($R_{1-3}$) corresponding to the side chains of amino acids found at the i, i+4, and i+7 positions of an ideal α-helix. Furthermore, the present inventors have developed a facile synthetic route to prepare a number of tris-benzamides to represent α-helical segments of target proteins. U.S. Patent Publication 2009/0012141, incorporated herein by reference, discloses a variety of oligo-benzamide compounds and methods of synthesis therefor.

More specifically, the present invention provides an oligo-benzamide peptidomimetic compound as illustrated includes 2 or 3 optionally substituted benzamides—so called "bis" and "tris" benzamides. In addition, linkages between the optionally substituted benzamides may be varied as necessary including ester, thioester, thioamide, trans-ethylene, ethyl, methyloxy, methylamino, hydroxyethyl, carbamate, urea, imide, hydrozido, aminoxy, or other linkages known to the skilled artisan. And, the oligo-benzamide peptidomimetic compound may be attached to amino acids, oligopeptides, optionally substituted alkyl, or other structures known to the skilled artisan.

The substitution on the substituted benzamide is generally on a benzene ring and may be on the 2, 3, 4, 5, or 6 position of each of the benzene rings. The substitutions may be at the same position on each of the benzamide rings but may also be at different positions on each of the benzene rings. For example, the substitution is connected to the benzamide ring by a chemical linkage including ether, thioether, amine, amide, carbamate, urea, and carbon-carbon (single-, double-, and triple-) bonds, and the substitution comprises optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof.

The present invention also provides an oligo-benzamide peptidomimetic compound that includes at least two optionally substituted benzamides, with each of the substituted benzamides having one substitution on a benzene ring. The substitutions are individually attached to the benzene rings of the oligo-benzamide peptidomimetic compound by a chemical linkage including ether, thioether, amine, amide, carbamate, urea, and carbon-carbon (single-, double-, and triple-) bonds. The substitutions generally include optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof.

Figure 2:
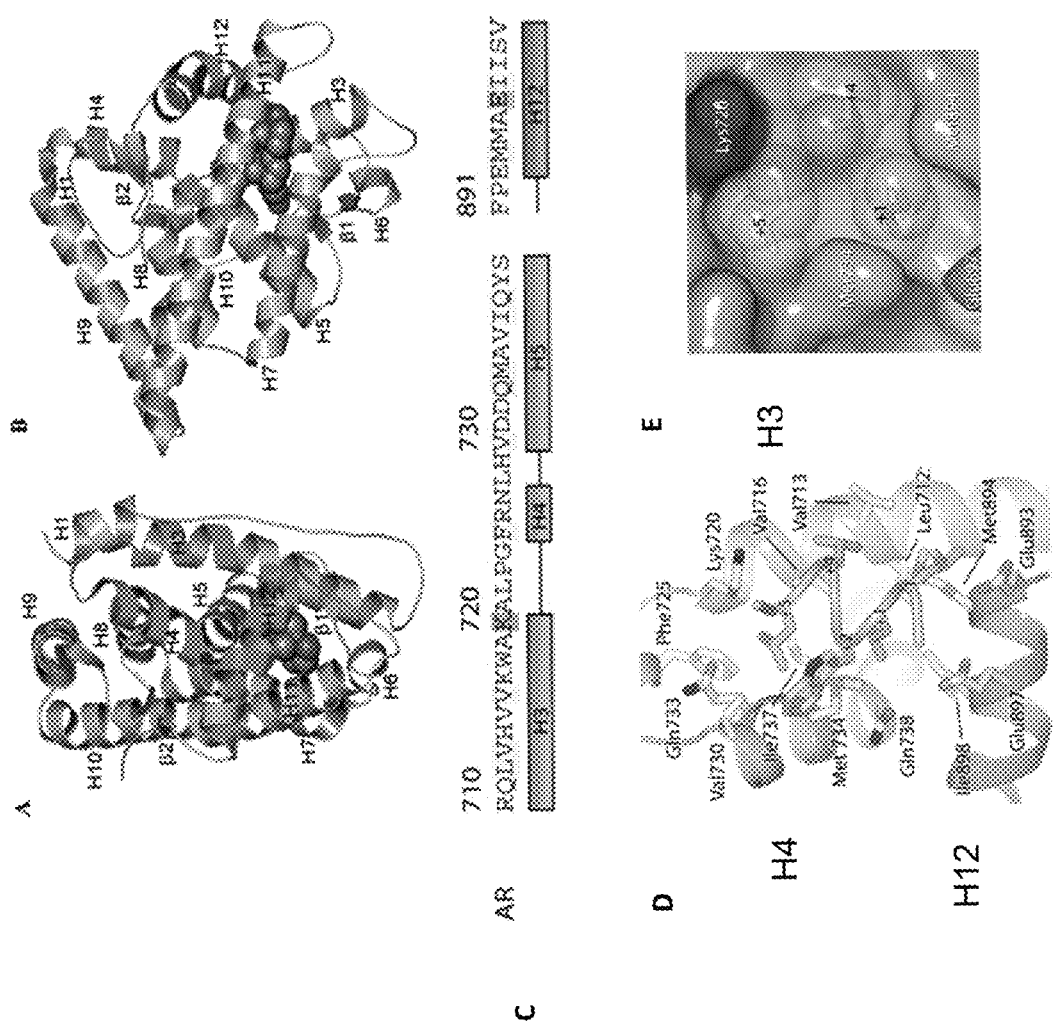
FIGS. 2A-2E. Modeling AR-PELP1 interactions.
Figure 3:
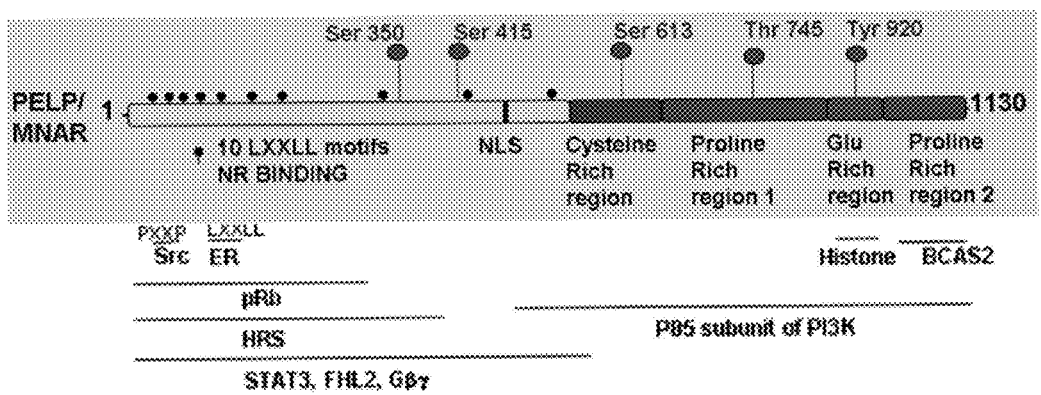
FIG. 3. Structure of PELP1 schematically and at the amino acid sequence.

U.S. Patent Publication 2009/0012141 provides synthesis schemes to prepare a-helix mimetic compounds of the present invention, for example, in FIG. 2 therein. A specific example in that document provides fifteen α-helix mimetic compounds made starting with a 4-amino-3-hydroxybenzoic acid compound 7, which was converted to an N—Ac protected methyl ester compound 8. Various alkyl groups were introduced to the hydroxyl group using a variety of alkyl halides and a base (e.g., NaOH) known to the skilled artisan. After the alkylation reaction, the methyl ester compound 9 was hydrolyzed using a base (like LiOH), and methyl 4-amino-3-hydroxybenzoate compound 10 was coupled to the free benzoic acid using a coupling reagent (like BOP), resulting in a benzamide compound 11 containing one alkyl group corresponding to the i position of a helix. These steps were repeated to synthesize oligo-benzamide compounds. Those of skill in the art would understand the broader applicability of such methods in the synthesis of other compounds such as those disclosed herein.

II. Pharmaceutical Formulations and Methods of Treatment

A. Formulations

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed (e.g., post-operative catheter). For practically any tumor, systemic delivery also is contemplated. This will prove especially important for attacking microscopic or metastatic cancer.

The active compounds may also be administered as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The actual dosage amount of a composition of the present invention administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

The pharmaceutical peptidomimetic composition includes a therapeutically effective amount of an oligo-benzamide peptidomimetic compound or a salt, a solvent, or a derivative thereof based on an oligo-benzamide peptidomimetic compound, and one or more pharmaceutically acceptable carriers. For example, the bis- or tris-benzamide peptidomimetic composition may also include one or more additional active ingredients, diluents, excipients, active agents, lubricants, preservatives, stabilizers, wetting agents, emulsifiers, salts for influencing osmotic pressure, buffers, colorings, flavorings, aromatic substances, penetration enhancers, surfactants, fatty acids, bile salts, chelating agents, colloids and combinations thereof. The pharmaceutical peptidomimetic compound may be adapted for oral, dermatological, transdermal or parenteral administration, in the form of a solution, a emulsions, a liposome-containing formulation, a tablet, a capsule, a gel capsule, a liquid syrup, a soft gel, a suppository, an enema, a patch, an ointment, a lotion, a cream, a gel, a drop, a spray, a liquid or a powder.

B. Prostate Cancer

Prostate cancer is a disease in which cancer develops in the prostate, a gland in the male reproductive system. In 2007, almost 220,000 new cases were reported, and over 27,000 deaths were attributed to this malignancy. It occurs when cells of the prostate mutate and begin to multiply out of control. These cells may spread (metastasize) from the prostate to other parts of the body, especially the bones and lymph nodes. Prostate cancer may cause pain, difficulty in urinating, erectile dysfunction and other symptoms.

Rates of prostate cancer vary widely across the world. Although the rates vary widely between countries, it is least common in South and East Asia, more common in Europe, and most common in the United States. According to the American Cancer Society, prostate cancer is least common among Asian men and most common among black men, with figures for white men in-between. However, these high rates may be affected by increasing rates of detection.

Prostate cancer develops most frequently in men over fifty. This cancer can occur only in men, as the prostate is exclusively of the male reproductive tract. It is the most common type of cancer in men in the United States, where it is responsible for more male deaths than any other cancer, except lung cancer. However, many men who develop prostate cancer never have symptoms, undergo no therapy, and eventually die of other causes. Many factors, including genetics and diet, have been implicated in the development of prostate cancer.

Prostate cancer screening is an attempt to find unsuspected cancers. Screening tests may lead to more specific follow-up tests such as a biopsy, where small pieces of the prostate are removed for closer study. As of 2006 prostate cancer screening options include the digital rectal exam and the prostate specific antigen (PSA) blood test. Screening for prostate cancer is controversial because it is not clear if the benefits of screening outweigh the risks of follow-up diagnostic tests and cancer treatments.

Prostate cancer is a slow-growing cancer, very common among older men. In fact, most prostate cancers never grow to the point where they cause symptoms, and most men with prostate cancer die of other causes before prostate cancer has an impact on their lives. The PSA screening test may detect these small cancers that would never become life threatening. Doing the PSA test in these men may lead to overdiagnosis, including additional testing and treatment. Follow-up tests, such as prostate biopsy, may cause pain, bleeding and infection. Prostate cancer treatments may cause urinary incontinence and erectile dysfunction. Therefore, it is essential that the risks and benefits of diagnostic procedures and treatment be carefully considered before PSA screening.

Prostate cancer screening generally begins after age 50, but this can vary due to ethnic backgrounds. Thus, the American Academy of Family Physicians and American College of Physicians recommend the physician discuss the risks and benefits of screening and decide based on individual patient preference. Although there is no officially recommended cutoff, many health care providers stop monitoring PSA in men who are older than 75 years old because of concern that prostate cancer therapy may do more harm than good as age progresses and life expectancy decreases.

Digital rectal examination (DRE) is a procedure where the examiner inserts a gloved, lubricated finger into the rectum to check the size, shape, and texture of the prostate. Areas which are irregular, hard or lumpy need further evaluation, since they may contain cancer. Although the DRE only evaluates the back of the prostate, 85% of prostate cancers arise in this part of the prostate. Prostate cancer which can be felt on DRE is generally more advanced. The use of DRE has never been shown to prevent prostate cancer deaths when used as the only screening test.

The PSA test measures the blood level of prostate-specific antigen, an enzyme produced by the prostate. Specifically, PSA is a serine protease similar to kallikrein. Its normal function is to liquify gelatinous semen after ejaculation, allowing spermatazoa to more easily navigate through the uterine cervix.

PSA levels under 4 ng/mL (nanograms per milliliter) are generally considered normal, however in individuals below the age of 50 sometimes a cutoff of 2.5 is used for the upper limit of normal, while levels over 4 ng/mL are considered abnormal (although in men over 65 levels up to 6.5 ng/mL may be acceptable, depending upon each laboratory's reference ranges). PSA levels between 4 and 10 ng/mL indicate a risk of prostate cancer higher than normal, but the risk does not seem to rise within this six-point range. When the PSA level is above 10 ng/mL, the association with cancer becomes stronger. However, PSA is not a perfect test. Some men with prostate cancer do not have an elevated PSA, and most men with an elevated PSA do not have prostate cancer.

PSA levels can change for many reasons other than cancer. Two common causes of high PSA levels are enlargement of the prostate (benign prostatic hypertrophy (BPH)) and infection in the prostate (prostatitis). It can also be raised for 24 hours after ejaculation and several days after catheterization. PSA levels are lowered in men who use medications used to treat BPH or baldness. These medications, finasteride (marketed as Proscar or Propecia) and dutasteride (marketed as Avodart), may decrease the PSA levels by 50% or more.

Several other ways of evaluating the PSA have been developed to avoid the shortcomings of simple PSA screening. The use of age-specific reference ranges improves the sensitivity and specificity of the test. The rate of rise of the PSA over time, called the PSA velocity, has been used to evaluate men with PSA levels between 4 and 10 ng/ml, but as of 2006, it has not proven to be an effective screening test. Comparing the PSA level with the size of the prostate, as measured by ultrasound or magnetic resonance imaging, has also been studied. This comparison, called PSA density, is both costly and, as of 2006, has not proven to be an effective screening test. PSA in the blood may either be free or bound to other proteins. Measuring the amount of PSA which is free or bound may provide additional screening information, but as of 2006, questions regarding the usefulness of these measurements limit their widespread use.

When a man has symptoms of prostate cancer, or a screening test indicates an increased risk for cancer, more invasive evaluation is offered. The only test which can fully confirm the diagnosis of prostate cancer is a biopsy, the removal of small pieces of the prostate for microscopic examination. However, prior to a biopsy, several other tools may be used to gather more information about the prostate and the urinary tract. Cystoscopy shows the urinary tract from inside the bladder, using a thin, flexible camera tube inserted down the urethra. Transrectal ultrasonography creates a picture of the prostate using sound waves from a probe in the rectum.

If cancer is suspected, a biopsy is offered. During a biopsy a urologist obtains tissue samples from the prostate via the rectum. A biopsy gun inserts and removes special hollow-core needles (usually three to six on each side of the prostate) in less than a second. Prostate biopsies are routinely done on an outpatient basis and rarely require hospitalization. Fifty-five percent of men report discomfort during prostate biopsy.

The tissue samples are then examined under a microscope to determine whether cancer cells are present, and to evaluate the microscopic features of any cancer found. If cancer is present, the pathologist reports the grade of the tumor. The grade tells how much the tumor tissue differs from normal prostate tissue and suggests how fast the tumor is likely to grow. The Gleason system is used to grade prostate tumors from 2 to 10, where a Gleason score of 10 indicates the most abnormalities. The pathologist assigns a number from 1 to 5 for the most common pattern observed under the microscope, then does the same for the second most common pattern. The sum of these two numbers is the Gleason score. The Whitmore-Jewett stage is another method sometimes used. Proper grading of the tumor is critical, since the grade of the tumor is one of the major factors used to determine the treatment recommendation.

An important part of evaluating prostate cancer is determining the stage, or how far the cancer has spread. Knowing the stage helps define prognosis and is useful when selecting therapies. The most common system is the four-stage TNM system (abbreviated from Tumor/Nodes/Metastases). Its components include the size of the tumor, the number of involved lymph nodes, and the presence of any other metastases.

The most important distinction made by any staging system is whether or not the cancer is still confined to the prostate. In the TNM system, clinical T1 and T2 cancers are found only in the prostate, while T3 and T4 cancers have spread elsewhere. Several tests can be used to look for evidence of spread. These include computed tomography to evaluate spread within the pelvis, bone scans to look for spread to the bones, and endorectal coil magnetic resonance imaging to closely evaluate the prostatic capsule and the seminal vesicles. Bone scans should reveal osteoblastic appearance due to increased bone density in the areas of bone metastisis—opposite to what is found in many other cancers that metastisize.

Prostate cancer can be treated with surgery, radiation therapy, hormonal therapy, occasionally chemotherapy, proton therapy, or some combination of these. The age and underlying health of the man as well as the extent of spread, appearance under the microscope, and response of the cancer to initial treatment are important in determining the outcome of the disease. Since prostate cancer is a disease of older men, many will die of other causes before a slowly advancing prostate cancer can spread or cause symptoms. This makes treatment selection difficult. The decision whether or not to treat localized prostate cancer (a tumor that is contained within the prostate) with curative intent is a patient trade-off between the expected beneficial and harmful effects in terms of patient survival and quality of life.

Watchful waiting, also called "active surveillance," refers to observation and regular monitoring without invasive treatment. Watchful waiting is often used when an early stage, slow-growing prostate cancer is found in an older man. Watchful waiting may also be suggested when the risks of surgery, radiation therapy, or hormonal therapy outweigh the possible benefits. Other treatments can be started if symptoms develop, or if there are signs that the cancer growth is accelerating (e.g., rapidly rising PSA, increase in Gleason score on repeat biopsy, etc.). Most men who choose watchful waiting for early stage tumors eventually have signs of tumor progression, and they may need to begin treatment within three years. Although men who choose watchful waiting avoid the risks of surgery and radiation, the risk of metastasis (spread of the cancer) may be increased. For younger men, a trial of active surveillance may not mean avoiding treatment altogether, but may reasonably allow a delay of a few years or more, during which time the quality of life impact of active treatment can be avoided. Published data to date suggest that carefully selected men will not miss a window for cure with this approach. Additional health problems that develop with advancing age during the observation period can also make it harder to undergo surgery and radiation therapy.

Clinically insignificant prostate tumors are often found by accident when a doctor incorrectly orders a biopsy not following the recommended guidelines (abnormal DRE and elevated PSA). The urologist must check that the PSA is not elevated for other reasons, prostatitis, etc. An annual biopsy is often recommended by a urologist for a patient who has selected watchful waiting when the tumor is clinically insignificant (no abnormal DRE or PSA). The tumors tiny size can be monitored this way and the patient can decide to have surgery only if the tumor enlarges which may take many years or never.

Surgical removal of the prostate, or prostatectomy, is a common treatment either for early stage prostate cancer, or for cancer which has failed to respond to radiation therapy. The most common type is radical retropubic prostatectomy, when the surgeon removes the prostate through an abdominal incision. Another type is radical perineal prostatectomy, when the surgeon removes the prostate through an incision in the perineum, the skin between the scrotum and anus. Radical prostatectomy can also be performed laparoscopically, through a series of small (1 cm) incisions in the abdomen, with or without the assistance of a surgical robot.

Radical prostatectomy is effective for tumors which have not spread beyond the prostate; cure rates depend on risk factors such as PSA level and Gleason grade. However, it may cause nerve damage that significantly alters the quality of life of the prostate cancer survivor. The most common serious complications are loss of urinary control and impotence. Reported rates of both complications vary widely depending on how they are assessed, by whom, and how long after surgery, as well as the setting (e.g., academic series vs. community-based or population-based data). Although penile sensation and the ability to achieve orgasm usually remain intact, erection and ejaculation are often impaired. Medications such as sildenafil (Viagra), tadalafil (Cialis), or vardenafil (Levitra) may restore some degree of potency. For most men with organ-confined disease, a more limited "nerve-sparing" technique may help avoid urinary incontinence and impotence.

Radical prostatectomy has traditionally been used alone when the cancer is small. In the event of positive margins or locally advanced disease found on pathology, adjuvant radiation therapy may offer improved survival. Surgery may also be offered when a cancer is not responding to radiation therapy. However, because radiation therapy causes tissue changes, prostatectomy after radiation has a higher risk of complications.

Transurethral resection of the prostate, commonly called a "TURP," is a surgical procedure performed when the tube from the bladder to the penis (urethra) is blocked by prostate enlargement. TURP is generally for benign disease and is not meant as definitive treatment for prostate cancer. During a TURP, a small tube (cystoscope) is placed into the penis and the blocking prostate is cut away.

In metastatic disease, where cancer has spread beyond the prostate, removal of the testicles (called orchiectomy) may be done to decrease testosterone levels and control cancer growth.

Radiation therapy, also known as radiotherapy, uses ionizing radiation to kill prostate cancer cells. When absorbed in tissue, ionizing radiation such as y and x-rays damage the DNA in cells, which increases the probability of apoptosis. Two different kinds of radiation therapy are used in prostate cancer treatment: external beam radiation therapy and brachytherapy.

External beam radiation therapy uses a linear accelerator to produce high-energy x-rays which are directed in a beam towards the prostate. A technique called Intensity Modulated Radiation Therapy (IMRT) may be used to adjust the radiation beam to conform with the shape of the tumor, allowing higher doses to be given to the prostate and seminal vesicles with less damage to the bladder and rectum. External beam radiation therapy is generally given over several weeks, with daily visits to a radiation therapy center. New types of radiation therapy may have fewer side effects then traditional treatment, one of these is Tomotherapy.

Permanent implant brachytherapy is a popular treatment choice for patients with low to intermediate risk features, can be performed on an outpatient basis, and is associated with good 10-year outcomes with relatively low morbidity. It involves the placement of about 100 small "seeds" containing radioactive material (such as iodine$^{125}$ or palladium$^{103}$) with a needle through the skin of the perineum directly into the tumor while under spinal or general anesthetic. These seeds emit lower-energy X-rays which are only able to travel a short distance. Although the seeds eventually become inert, they remain in the prostate permanently. The risk of exposure to others from men with implanted seeds is generally accepted to be insignificant.

Radiation therapy is commonly used in prostate cancer treatment. It may be used instead of surgery for early cancers, and it may also be used in advanced stages of prostate cancer to treat painful bone metastases. Radiation treatments also can be combined with hormonal therapy for intermediate risk disease, when radiation therapy alone is less likely to cure the cancer. Some radiation oncologists combine external beam radiation and brachytherapy for intermediate to high risk situations. One study found that the combination of six months of androgen suppressive therapy combined with external beam radiation had improved survival compared to radiation alone in patients with localized prostate cancer. Others use a "triple modality" combination of external beam radiation therapy, brachytherapy, and hormonal therapy.

Less common applications for radiotherapy are when cancer is compressing the spinal cord, or sometimes after surgery, such as when cancer is found in the seminal vesicles, in the lymph nodes, outside the prostate capsule, or at the margins of the biopsy.

Radiation therapy is often offered to men whose medical problems make surgery more risky. Radiation therapy appears to cure small tumors that are confined to the prostate just about as well as surgery. However, as of 2006 some issues remain unresolved, such as whether radiation should be given to the rest of the pelvis, how much the absorbed dose should be, and whether hormonal therapy should be given at the same time.

Side effects of radiation therapy might occur after a few weeks into treatment. Both types of radiation therapy may cause diarrhea and rectal bleeding due to radiation proctitis, as well as urinary incontinence and impotence. Symptoms tend to improve over time. Men who have undergone external beam radiation therapy will have a higher risk of later developing colon cancer and bladder cancer.

Cryosurgery is another method of treating prostate cancer. It is less invasive than radical prostatectomy, and general anesthesia is less commonly used. Under ultrasound guidance, metal rods are inserted through the skin of the perineum into the prostate. Highly purified Argon gas is used to cool the rods, freezing the surrounding tissue at −196° C. (−320° F.). As the water within the prostate cells freeze, the cells die. The urethra is protected from freezing by a catheter filled with warm liquid. Cryosurgery generally causes fewer problems with urinary control than other treatments, but impotence occurs up to ninety percent of the time. When used as the initial treatment for prostate cancer and in the hands of an experienced cryosurgeon, cryosurgery has a 10 year biochemical disease free rate superior to all other treatments including radical prostatectomy and any form of radiation Cryosurgery has also been demonstrated to be superior to radical prostatectomy for recurrent cancer following radiation therapy.

Hormonal therapy uses medications or surgery to block prostate cancer cells from getting dihydrotestosterone (DHT), a hormone produced in the prostate and required for the growth and spread of most prostate cancer cells. Blocking DHT often causes prostate cancer to stop growing and even shrink. However, hormonal therapy rarely cures prostate cancer because cancers which initially respond to hormonal therapy typically become resistant after one to two years. Hormonal therapy is therefore usually used when cancer has spread from the prostate. It may also be given to certain men undergoing radiation therapy or surgery to help prevent return of their cancer.

Hormonal therapy for prostate cancer targets the pathways the body uses to produce DHT. A feedback loop involving the testicles, the hypothalamus, and the pituitary, adrenal, and prostate glands controls the blood levels of DHT. First, low blood levels of DHT stimulate the hypothalamus to produce gonadotropin releasing hormone (GnRH). GnRH then stimulates the pituitary gland to produce luteinizing hormone (LH), and LH stimulates the testicles to produce testosterone. Finally, testosterone from the testicles and dehydroepiandrosterone from the adrenal glands stimulate the prostate to produce more DHT. Hormonal therapy can decrease levels of DHT by interrupting this pathway at any point.

There are several forms of hormonal therapy. Orchiectomy is surgery to remove the testicles. Because the testicles make most of the body's testosterone, after orchiectomy testosterone levels drop. Now the prostate not only lacks the testosterone stimulus to produce DHT, but also it does not have enough testosterone to transform into DHT.

Anti-androgens are medications such as flutamide, bicalutamide, nilutamide, and cyproterone acetate which directly block the actions of testosterone and DHT within prostate cancer cells.

Medications which block the production of adrenal androgens such as DHEA include ketoconazole and aminoglutethimide. Because the adrenal glands only make about 5% of the body's androgens, these medications are generally used only in combination with other methods that can block the 95% of androgens made by the testicles. These combined methods are called total androgen blockade (TAB). TAB can also be achieved using antiandrogens.

GnRH action can be interrupted in one of two ways. GnRH antagonists suppress the production of LH directly, while GnRH agonists suppress LH through the process of downregulation after an initial stimulation effect. Abarelix is an example of a GnRH antagonist, while the GnRH agonists include leuprolide, goserelin, triptorelin, and buserelin. Initially, GnRH agonists increase the production of LH. However, because the constant supply of the medication does not match the body's natural production rhythm, production of both LH and GnRH decreases after a few weeks.

As of 2006 the most successful hormonal treatments are orchiectomy and GnRH agonists. Despite their higher cost, GnRH agonists are often chosen over orchiectomy for cosmetic and emotional reasons. Eventually, total androgen blockade may prove to be better than orchiectomy or GnRH agonists used alone.

Each treatment has disadvantages which limit its use in certain circumstances. Although orchiectomy is a low-risk surgery, the psychological impact of removing the testicles can be significant. The loss of testosterone also causes hot flashes, weight gain, loss of libido, enlargement of the breasts (gynecomastia), impotence and osteoporosis. GnRH agonists eventually cause the same side effects as orchiectomy but may cause worse symptoms at the beginning of treatment. When GnRH agonists are first used, testosterone surges can lead to increased bone pain from metastatic cancer, so antiandrogens or abarelix are often added to blunt these side effects. Estrogens are not commonly used because they increase the risk for cardiovascular disease and blood clots. The antiandrogens do not generally cause impotence and usually cause less loss of bone and muscle mass. Ketoconazole can cause liver damage with prolonged use, and aminoglutethimide can cause skin rashes.

Palliative care for advanced stage prostate cancer focuses on extending life and relieving the symptoms of metastatic disease. Chemotherapy may be offered to slow disease progression and postpone symptoms. The most commonly used regimen combines the chemotherapeutic drug docetaxel with a corticosteroid such as prednisone. Bisphosphonates such as zoledronic acid have been shown to delay skeletal complications such as fractures or the need for radiation therapy in patients with hormone-refractory metastatic prostate cancer.

Bone pain due to metastatic disease is treated with opioid pain relievers such as morphine and oxycodone. External beam radiation therapy directed at bone metastases may provide pain relief. Injections of certain radioisotopes, such as strontium$^{89}$, phosphorus$^{32}$, or samarium$^{153}$, also target bone metastases and may help relieve pain.

High Intensity Focused Ultrasound (HIFU) for prostate cancer utilizes ultrasonnic waves to ablate/destroy the tissue of the prostate. During the HIFU procedure, sound waves are used to heat the prostate tissue thus destroying the cancerous cells. Essentially, ultrasonic waves are precisely focused on specific areas of the prostate to eliminate the prostate cancer with minimal risks of effecting other tissue or organs. Temperatures at the focal point of the sound waves can exceed 100° C. The ability to focus the ultrasonic waves leads to a relatively low occurrence of both incontinence and impotence. (0.6% and 0-20%, respectively). According to international studies, when compared to other procedures, HIFU has a high success rate with a reduced risk of side effects. Studies using the Sonablate 500 HIFU machine have shown that 94% of patients with a pretreatment PSA (Prostate Specific Antigen) of less than 10 g/ml were cancer-free after three years. However, many studies of HIFU were performed by manufacturers of HIFU devices, or members of manufacturers' advisory panels.

HIFU was first used in the 1940's and 1950's in efforts to destroy tumors in the central nervous system. Since then, HIFU has been shown to be effective at destroying malignant tissue in the brain, prostate, spleen, liver, kidney, breast, and bone. Today, the HIFU procedure for prostate cancer is performed using a transrectal probe. This procedure has been performed for over ten years and is currently approved for use in Japan, Europe, Canada, and parts of Central and South America.

Although not yet approved for use in the Unites States, many patients have received the HIFU procedure at facilities in Canada, and Central and South America. Currently, therapy is available using the Sonablate 500 or the Ablatherm. The Sonablate 500 is designed by Focus Surgery of Indianapolis, Ind. and is used in international HIFU centers around the world.

Several medications and vitamins may also help prevent prostate cancer. Two dietary supplements, vitamin E and selenium, may help prevent prostate cancer when taken daily. Estrogens from fermented soybeans and other plant sources (called phytoestrogens) may also help prevent prostate cancer. The selective estrogen receptor modulator drug toremifene has shown promise in early trials. Two medications which block the conversion of testosterone to dihydrotestosterone, finasteride and dutasteride, have also shown some promise. As of 2006 the use of these medications for primary prevention is still in the testing phase, and they are not widely used for this purpose. The problem with these medications is that they may preferentially block the development of lower-grade prostate tumors, leading to a relatively greater chance of higher grade cancers, and negating any overall survival improvement. Green tea may be protective (due to its polyphenol content), though the data is mixed. A 2006 study of green tea derivatives demonstrated promising prostate cancer prevention in patients at high risk for the disease. In 2003, an Australian research team led by Graham Giles of The Cancer Council Australia concluded that frequent masturbation by males appears to help prevent the development of prostate cancer. Recent research published in the Journal of the National Cancer Institute suggests that taking multivitamins more than seven times a week can increase the risks of contracting the disease. This research was unable to highlight the exact vitamins responsible for this increase (almost double), although they suggest that vitamin A, vitamin E and beta-carotene may lie at its heart. It is advised that those taking multivitamins never exceed the stated daily dose on the label. Scientists recommend a healthy, well balanced diet rich in fiber, and to reduce intake of meat. A 2007 study published in the Journal of the National Cancer Institute found that men eating cauliflower, broccoli, or one of the other cruciferous vegetables, more than once a week were 40% less likely to develop prostate cancer than men who rarely ate those vegetables. Scientists believe the reason for this phenomenon has to do with a phytochemical called Diindolylmethane in these vegetables that has anti-androgenic and immune modulating properties. This compound is currently under investigation by the National Cancer Institute as a natural therapeutic for prostate cancer.

C. Breast Cancer

Breast cancer refers to cancers originating from breast tissue, most commonly from the inner lining of milk ducts or the lobules that supply the ducts with milk. Cancers originating from ducts are known as ductal carcinomas; those originating from lobules are known as lobular carcinomas. There are many different types of breast cancer, with different stages (spread), aggressiveness, and genetic makeup; survival varies greatly depending on those factors. Computerized models are available to predict survival. With best treatment and dependent on staging, 10-year disease-free survival varies from 98% to 10%. Treatment includes surgery, drugs (hormonal therapy and chemotherapy), and radiation.

Worldwide, breast cancer comprises 10.4% of all cancer incidence among women, making it the second most common type of non-skin cancer (after lung cancer) and the fifth most common cause of cancer death. In 2004, breast cancer caused 519,000 deaths worldwide (7% of cancer deaths; almost 1% of all deaths). Breast cancer is about 100 times more common in women than in men, although males tend to have poorer outcomes due to delays in diagnosis.

Some breast cancers require the hormones estrogen and progesterone to grow, and have receptors for those hormones. After surgery those cancers are treated with drugs that interfere with those hormones, usually tamoxifen, and with drugs that shut off the production of estrogen in the ovaries or elsewhere; this may damage the ovaries and end fertility. After surgery, low-risk, hormone-sensitive breast cancers may be treated with hormone therapy and radiation alone. Breast cancers without hormone receptors, or which have spread to the lymph nodes in the armpits, or which express certain genetic characteristics, are higher-risk, and are treated more aggressively. One standard regimen, popular in the U.S., is cyclophosphamide plus doxorubicin (Adriamycin), known as CA; these drugs damage DNA in the cancer, but also in fast-growing normal cells where they cause serious side effects. Sometimes a taxane drug, such as docetaxel, is added, and the regime is then known as CAT; taxane attacks the microtubules in cancer cells. An equivalent treatment, popular in Europe, is cyclophosphamide, methotrexate, and fluorouracil (CMF). Monoclonal antibodies, such as trastuzumab (Herceptin), are used for cancer cells that have the HER2 mutation. Radiation is usually added to the surgical bed to control cancer cells that were missed by the surgery, which usually extends survival, although radiation exposure to the heart may cause damage and heart failure in the following years.

While screening techniques (which are further discussed below) are useful in determining the possibility of cancer, a further testing is necessary to confirm whether a lump detected on screening is cancer, as opposed to a benign alternative such as a simple cyst.

In a clinical setting, breast cancer is commonly diagnosed using a "triple test" of clinical breast examination (breast examination by a trained medical practitioner), mammography, and fine needle aspiration cytology. Both mammography and clinical breast exam, also used for screening, can indicate an approximate likelihood that a lump is cancer, and may also identify any other lesions. Fine Needle Aspiration and Cytology (FNAC), which may be done in a doctor's office using local anaesthetic if required, involves attempting to extract a small portion of fluid from the lump. Clear fluid makes the lump highly unlikely to be cancerous, but bloody fluid may be sent off for inspection under a microscope for cancerous cells. Together, these three tools can be used to diagnose breast cancer with a good degree of accuracy.

Other options for biopsy include core biopsy, where a section of the breast lump is removed, and an excisional biopsy, where the entire lump is removed.

In addition vacuum-assisted breast biopsy (VAB) may help diagnose breast cancer among patients with a mammographically detected breast in women according to a systematic review. In this study, summary estimates for vacuum assisted breast biopsy in diagnosis of breast cancer were as follows sensitivity was 98.1% with 95% CI=0.972-0.987 and specificity was 100% with 95% CI=0.997-0.999. However underestimate rates of atypical ductal hyperplasia (ADH) and ductal carcinoma in situ (DCIS) were 20.9% with 95% CI=0.177-0.245 and 11.2% with 95% CI=0.098-0.128 respectively.

Breast cancer screening refers to testing otherwise-healthy women for breast cancer in an attempt to achieve an earlier diagnosis. The assumption is that early detection will improve outcomes. A number of screening test have been employed including: clinical and self breast exams, mammography, genetic screening, ultrasound, and magnetic resonance imaging.

A clinical or self breast exam involves feeling the breast for lumps or other abnormalities. Research evidence does not support the effectiveness of either type of breast exam, because by the time a lump is large enough to be found it is likely to have been growing for several years and will soon be large enough to be found without an exam. Mammographic screening for breast cancer uses x-rays to examine the breast for any uncharacteristic masses or lumps. In women at high risk, such as those with a strong family history of cancer, mammography screening is recommended at an earlier age and additional testing may include genetic screening that tests for the BRCA genes and/or magnetic resonance imaging.

Breast cancer is sometimes treated first with surgery, and then with chemotherapy, radiation, or both. Treatments are given with increasing aggressiveness according to the prognosis and risk of recurrence. Stage 1 cancers (and DCIS) have an excellent prognosis and are generally treated with lumpectomy with or without chemotherapy or radiation. Although the aggressive HER2+ cancers should also be treated with the trastuzumab (Herceptin) regime. Stage 2 and 3 cancers with a progressively poorer prognosis and greater risk of recurrence are generally treated with surgery (lumpectomy or mastectomy with or without lymph node removal), radiation (sometimes) and chemotherapy (plus trastuzumab for HER2+ cancers). Stage 4, metastatic cancer, (i.e., spread to distant sites) is not curable and is managed by various combinations of all treatments from surgery, radiation, chemotherapy and targeted therapies. These treatments increase the median survival time of stage 4 breast cancer by about 6 months.

D. Ovarian Cancer

Ovarian cancer is a cancerous growth arising from different parts of the ovary. Most (>90%) ovarian cancers are classified as "epithelial" and were believed to arise from the surface (epithelium) of the ovary. However, recent evidence suggests that the Fallopian tube could also be the source of some ovarian cancers. Since the ovaries and tubes are closely related to each other, it is hypothesized that these cells can mimic ovarian cancer. Other types arise from the egg cells (germ cell tumor) or supporting cells (sex cord/stromal).

In 2004, in the United States, 25,580 new cases were diagnosed and 16,090 women died of ovarian cancer. The risk increases with age and decreases with pregnancy. Lifetime risk is about 1.6%, but women with affected first-degree relatives have a 5% risk. Women with a mutated BRCA1 or BRCA2 gene carry a risk between 25% and 60% depending on the specific mutation. Ovarian cancer is the fifth leading cause of death from cancer in women and the leading cause of death from gynecological cancer.

Ovarian cancer causes non-specific symptoms. Early diagnosis would result in better survival, on the assumption that stage I and II cancers progress to stage III and IV cancers (but this has not been proven). Most women with ovarian cancer report one or more symptoms such as abdominal pain or discomfort, an abdominal mass, bloating, back pain, urinary urgency, constipation, tiredness and a range of other non-specific symptoms, as well as more specific symptoms such as pelvic pain, abnormal vaginal bleeding or involuntary weight loss. There can be a build-up of fluid (ascites) in the abdominal cavity.

Diagnosis of ovarian cancer starts with a physical examination (including a pelvic examination), a blood test (for CA-125 and sometimes other markers), and transvaginal ultrasound. The diagnosis must be confirmed with surgery to inspect the abdominal cavity, take biopsies (tissue samples for microscopic analysis) and look for cancer cells in the abdominal fluid. Treatment usually involves chemotherapy and surgery, and sometimes radiotherapy.

In most cases, the cause of ovarian cancer remains unknown. Older women, and in those who have a first or second degree relative with the disease, have an increased risk. Hereditary forms of ovarian cancer can be caused by mutations in specific genes (most notably BRCA1 and BRCA2, but also in genes for hereditary nonpolyposis colorectal cancer). Infertile women and those with a condition called endometriosis, those who have never been pregnant and those who use postmenopausal estrogen replacement therapy are at increased risk. Use of combined oral contraceptive pills is a protective factor. The risk is also lower in women who have had their uterine tubes blocked surgically (tubal ligation).

Ovarian cancer is classified according to the histology of the tumor, obtained in a pathology report. Histology dictates many aspects of clinical treatment, management, and prognosis. Surface epithelial-stromal tumour, also known as ovarian epithelial carcinoma, is the most common type of ovarian cancer. It includes serous tumour, endometrioid tumor and mucinous cystadenocarcinoma. Sex cord-stromal tumor, including estrogen-producing granulosa cell tumor and virilizing Sertoli-Leydig cell tumor or arrhenoblastoma, accounts for 8% of ovarian cancers. Germ cell tumor accounts for approximately 30% of ovarian tumors but only 5% of ovarian cancers, because most germ cell tumors are teratomas and most teratomas are benign (see Teratoma). Germ cell tumor tends to occur in young women and girls. The prognosis depends on the specific histology of germ cell tumor, but overall is favorable. Mixed tumors, containing elements of more than one of the above classes of tumor histology.

Ovarian cancer can also be a secondary cancer, the result of metastasis from a primary cancer elsewhere in the body. Seven percent of ovarian cancers are due to metastases while the rest are primary cancers. Common primary cancers are breast cancer and gastrointestinal cancer (a common mistake is to name all peritoneal metastases from any gastrointestinal cancer as Krukenberg cancer, but this is only the case if it originates from primary gastric cancer). Surface epithelial-stromal tumor can originate in the peritoneum (the lining of the abdominal cavity), in which case the ovarian cancer is secondary to primary peritoneal cancer, but treatment is basically the same as for primary surface epithelial-stromal tumor involving the peritoneum.

Ovarian cancer staging is by the FIGO staging system and uses information obtained after surgery, which can include a total abdominal hysterectomy, removal of (usually) both ovaries and fallopian tubes, (usually) the omentum, and pelvic (peritoneal) washings for cytopathology. The AJCC stage is the same as the FIGO stage. The AJCC staging system describes the extent of the primary Tumor (T), the absence or presence of metastasis to nearby lymph Nodes (N), and the absence or presence of distant Metastasis (M).

The AJCC/TNM staging system includes three categories for ovarian cancer, T, N and M. The T category contains three other subcategories, T1, T2 and T3, each of them being classified according to the place where the tumor has developed (in one or both ovaries, inside or outside the ovary). The T1 category of ovarian cancer describes ovarian tumors that are confined to the ovaries, and which may affect one or both of them. The sub-subcategory T1a is used to stage cancer that is found in only one ovary, which has left the capsule intact and which cannot be found in the fluid taken from the pelvis. Cancer that has not affected the capsule, is confined to the inside of the ovaries and cannot be found in the fluid taken from the pelvis but has affected both ovaries is staged as T1b. T1c category describes a type of tumor that can affect one or both ovaries, and which has grown through the capsule of an ovary or it is present in the fluid taken from the pelvis. T2 is a more advanced stage of cancer. In this case, the tumor has grown in one or both ovaries and is spread to the uterus, fallopian tubes or other pelvic tissues. Stage T2a is used to describe a cancerous tumor that has spread to the uterus or the fallopian tubes (or both) but which is not present in the fluid taken from the pelvis. Stages T2b and T2c indicate cancer that metastasized to other pelvic tissues than the uterus and fallopian tubes and which cannot be seen in the fluid taken from the pelvis, respectively tumors that spread to any of the pelvic tissues (including uterus and fallopian tubes) but which can also be found in the fluid taken from the pelvis. T3 is the stage used to describe cancer that has spread to the peritoneum. This stage provides information on the size of the metastatic tumors (tumors that are located in other areas of the body, but are caused by ovarian cancer). These tumors can be very small, visible only under the microscope (T3a), visible but not larger than 2 centimeters (T3b) and bigger than 2 centimeters (T3c).

This staging system also uses N categories to describe cancers that have or not spread to nearby lymph nodes. There are only two N categories, N0 which indicates that the cancerous tumors have not affected the lymph nodes, and N1 which indicates the involvement of lymph nodes close to the tumor. The M categories in the AJCC/TNM staging system provide information on whether the ovarian cancer has metastasized to distant organs such as liver or lungs. M0 indicates that the cancer did not spread to distant organs and M1 category is used for cancer that has spread to other organs of the body. The AJCC/TNM staging system also contains a Tx and a Nx sub-category which indicates that the extent of the tumor cannot be described because of insufficient data, respectively the involvement of the lymph nodes cannot be described because of the same reason.

Ovarian cancer, as well as any other type of cancer, is also graded, apart from staged. The histologic grade of a tumor measures how abnormal or malignant its cells look under the microscope. There are four grades indicating the likelihood of the cancer to spread and the higher the grade, the more likely for this to occur. Grade 0 is used to describe non-invasive tumors. Grade 0 cancers are also referred to as borderline tumors. Grade 1 tumors have cells that are well differentiated (look very similar to the normal tissue) and are the ones with the best prognosis. Grade 2 tumors are also called moderately well differentiated and they are made up by cells that resemble the normal tissue. Grade 3 tumors have the worst prognosis and their cells are abnormal, referred to as poorly differentiated.

The signs and symptoms of ovarian cancer are most of the times absent, but when they exist they are nonspecific. In most cases, the symptoms persist for several months until the patient is diagnosed.

A prospective case-control study of 1,709 women visiting primary care clinics found that the combination of bloating, increased abdominal size, and urinary symptoms was found in 43% of those with ovarian cancer but in only 8% of those presenting to primary care clinics.

The exact cause is usually unknown. The risk of developing ovarian cancer appears to be affected by several factors. The more children a woman has, the lower her risk of ovarian cancer. Early age at first pregnancy, older age of final pregnancy and the use of low dose hormonal contraception have also been shown to have a protective effect. Ovarian cancer is reduced in women after tubal ligation.

The relationship between use of oral contraceptives and ovarian cancer was shown in a summary of results of 45 case-control and prospective studies. Cumulatively these studies show a protective effect for ovarian cancers. Women who used oral contraceptives for 10 years had about a 60% reduction in risk of ovarian cancer. (risk ratio 0.42 with statistical significant confidence intervals given the large study size, not unexpected). This means that if 250 women took oral contraceptives for 10 years, 1 ovarian cancer would be prevented. This is by far the largest epidemiological study to date on this subject (45 studies, over 20,000 women with ovarian cancer and about 80,000 controls).

The link to the use of fertility medication, such as Clomiphene citrate, has been controversial. An analysis in 1991 raised the possibility that use of drugs may increase the risk of ovarian cancer. Several cohort studies and case-control studies have been conducted since then without demonstrating conclusive evidence for such a link. It will remain a complex topic to study as the infertile population differs in parity from the "normal" population.

There is good evidence that in some women genetic factors are important. Carriers of certain mutations of the BRCA1 or the BRCA2 gene are notably at risk. The BRCA1 and BRCA2 genes account for 5%-13% of ovarian cancers and certain populations (e.g. Ashkenazi Jewish women) are at a higher risk of both breast cancer and ovarian cancer, often at an earlier age than the general population. Patients with a personal history of breast cancer or a family history of breast and/or ovarian cancer, especially if diagnosed at a young age, may have an elevated risk.

A strong family history of uterine cancer, colon cancer, or other gastrointestinal cancers may indicate the presence of a syndrome known as hereditary nonpolyposis colorectal cancer (HNPCC, also known as Lynch syndrome), which confers a higher risk for developing ovarian cancer. Patients with strong genetic risk for ovarian cancer may consider the use of prophylactic, i.e. preventative, oophorectomy after completion of childbearing.[citation needed] Australia being member of International Cancer Genome Consortium is leading efforts to map ovarian cancer's complete genome.

Ovarian cancer at its early stages (I/II) is difficult to diagnose until it spreads and advances to later stages (III/IV). This is because most symptoms are non-specific and thus of little use in diagnosis.

When an ovarian malignancy is included in the list of diagnostic possibilities, a limited number of laboratory tests are indicated. A complete blood count (CBC) and serum electrolyte test should be obtained in all patients.

The serum BHCG level should be measured in any female in whom pregnancy is a possibility. In addition, serum alpha-fetoprotein (AFP) and lactate dehydrogenase (LDH) should be measured in young girls and adolescents with suspected ovarian tumors because the younger the patient, the greater the likelihood of a malignant germ cell tumor.

A blood test called CA-125 is useful in differential diagnosis and in follow up of the disease, but it by itself has not been shown to be an effective method to screen for early-stage ovarian cancer due to its unacceptable low sensitivity and specificity. However, this is the only widely-used marker currently available.

Current research is looking at ways to combine tumor markers proteomics along with other indicators of disease (i.e., radiology and/or symptoms) to improve accuracy. The challenge in such an approach is that the very low population prevalence of ovarian cancer means that even testing with very high sensitivity and specificity will still lead to a number of false positive results (i.e., performing surgical procedures in which cancer is not found intra-operatively). However, the contributions of proteomics are still in the early stages and require further refining. Current studies on proteomics mark the beginning of a paradigm shift towards individually tailored therapy.

A pelvic examination and imaging including CT scan and trans-vaginal ultrasound are essential. Physical examination may reveal increased abdominal girth and/or ascites (fluid within the abdominal cavity). Pelvic examination may reveal an ovarian or abdominal mass. The pelvic examination can include a rectovaginal component for better palpation of the ovaries. For very young patients, magnetic resonance imaging may be preferred to rectal and vaginal examination.

To definitively diagnose ovarian cancer, a surgical procedure to take a look into the abdomen is required. This can be an open procedure (laparotomy, incision through the abdominal wall) or keyhole surgery (laparoscopy). During this procedure, suspicious areas will be removed and sent for microscopic analysis. Fluid from the abdominal cavity can also be analysed for cancerous cells. If there is cancer, this procedure can also determine its spread (which is a form of tumor staging).

Women who have had children are less likely to develop ovarian cancer than women who have not, and breastfeeding may also reduce the risk of certain types of ovarian cancer. Tubal ligation and hysterectomy reduce the risk and removal of both tubes and ovaries (bilateral salpingo-oophorectomy) dramatically reduces the risk of not only ovarian cancer but breast cancer also. The use of oral contraceptives (birth control pills) for five years or more decreases the risk of ovarian cancer in later life by 50%.

Tubal ligation is believed to decrease the chance of developing ovarian cancer by up to 67% while a hysterectomy may reduce the risk of getting ovarian cancer by about one-third. Moreover, according to some studies, analgesics such as acetaminophen and aspirin seem to reduce one's risks of developing ovarian cancer. Yet, the information is not consistent and more research needs to be carried on this matter.

Routine screening of women for ovarian cancer is not recommended by any professional society—this includes the U.S. Preventive Services Task Force, the American Cancer Society, the American College of Obstetricians and Gynecologists, and the National Comprehensive Cancer Network. This is because no trial has shown improved survival for women undergoing screening. Screening for any type of cancer must be accurate and reliable—it needs to accurately detect the disease and it must not give false positive results in people who do not have cancer. As yet there is no technique for ovarian screening that has been shown to fulfil these criteria. However in some countries such as the UK, women who are likely to have an increased risk of ovarian cancer (for example if they have a family history of the disease) can be offered individual screening through their doctors, although this will not necessarily detect the disease at an early stage.

Researchers are assessing different ways to screen for ovarian cancer. Screening tests that could potentially be used alone or in combination for routine screening include the CA-125 marker and transvaginal ultrasound. Doctors can measure the levels of the CA-125 protein in a woman's blood—high levels could be a sign of ovarian cancer, but this is not always the case. And not all women with ovarian cancer have high CA-125 levels. Transvaginal ultrasound involves using an ultrasound probe to scan the ovaries from inside the vagina, giving a clearer image than scanning the abdomen. The UK Collaborative Trial of Ovarian Cancer Screening is testing a screening technique that combines CA-125 blood tests with transvaginal ultrasound.

The purpose of screening is to diagnose ovarian cancer at an early stage, when it is more likely to be treated successfully. However the development of the disease is not fully understood, and it has been argued that early-stage cancers may not always develop into late-stage disease. With any screening technique there are risks and benefits that need to be carefully considered, and health authorities need to assess these before introducing any ovarian cancer screening programs.

The goal of ovarian cancer screening is to detect the disease at stage I. Several large studies are ongoing, but none have identified an effective technique. In 2009, however, early results from the UK Collaborative Trial of Ovarian Cancer Screening (UKCTOCS) showed that a technique combining annual CA-125 tests with ultrasound imaging did help to detect the disease at an early stage. However, it is not yet clear if this approach could actually help to save lives— the full results of the trial will be published in 2015.

Surgical treatment may be sufficient for malignant tumors that are well-differentiated and confined to the ovary. Addition of chemotherapy may be required for more aggressive tumors that are confined to the ovary. For patients with advanced disease a combination of surgical reduction with a combination chemotherapy regimen is standard. Borderline tumors, even following spread outside of the ovary, are managed well with surgery, and chemotherapy is not seen as useful.

Surgery is the preferred treatment and is frequently necessary to obtain a tissue specimen for differential diagnosis via its histology. Surgery performed by a specialist in gynecologic oncology usually results in an improved result. Improved survival is attributed to more accurate staging of the disease and a higher rate of aggressive surgical excision of tumor in the abdomen by gynecologic oncologists as opposed to general gynecologists and general surgeons.

The type of surgery depends upon how widespread the cancer is when diagnosed (the cancer stage), as well as the presumed type and grade of cancer. The surgeon may remove one (unilateral oophorectomy) or both ovaries (bilateral oophorectomy), the fallopian tubes (salpingectomy), and the uterus (hysterectomy). For some very early tumors (stage 1, low grade or low-risk disease), only the involved ovary and fallopian tube will be removed (called a "unilateral salpingo-oophorectomy," USO), especially in young females who wish to preserve their fertility.

In advanced malignancy, where complete resection is not feasible, as much tumor as possible is removed (debulking surgery). In cases where this type of surgery is successful (i.e., <1 cm in diameter of tumor is left behind ["optimal debulking"]), the prognosis is improved compared to patients where large tumor masses (>1 cm in diameter) are left behind. Minimally invasive surgical techniques may facilitate the safe removal of very large (greater than 10 cm) tumors with fewer complications of surgery.

Chemotherapy has been a general standard of care for ovarian cancer for decades, although with highly variable protocols. Chemotherapy is used after surgery to treat any residual disease, if appropriate. This depends on the histology of the tumor; some kinds of tumor (particularly teratoma) are not sensitive to chemotherapy. In some cases, there may be reason to perform chemotherapy first, followed by surgery.

For patients with stage IIIC epithelial ovarian adenocarcinomas who have undergone successful optimal debulking, a recent clinical trial demonstrated that median survival time is significantly longer for patient receiving intraperitoneal (IP) chemotherapy. Patients in this clinical trial reported less compliance with IP chemotherapy and fewer than half of the patients received all six cycles of IP chemotherapy. Despite this high "drop-out" rate, the group as a whole (including the patients that didn't complete IP chemotherapy treatment) survived longer on average than patients who received intravenous chemotherapy alone.

Some specialists believe the toxicities and other complications of IP chemotherapy will be unnecessary with improved IV chemotherapy drugs currently being developed.

Although IP chemotherapy has been recommended as a standard of care for the first-line treatment of ovarian cancer, the basis for this recommendation has been challenged.

Radiation therapy is not effective for advanced stages because when vital organs are in the radiation field, a high dose cannot be safely delivered. Radiation therapy is then commonly avoided in such stages as the vital organs may not be able to withstand the problems associated with these ovarian cancer treatments.

Ovarian cancer usually has a poor prognosis. It is disproportionately deadly because it lacks any clear early detection or screening test, meaning that most cases are not diagnosed until they have reached advanced stages. More than 60% of women presenting with this cancer already have stage III or stage IV cancer, when it has already spread beyond the ovaries. Ovarian cancers shed cells into the naturally occurring fluid within the abdominal cavity. These cells can then implant on other abdominal (peritoneal) structures, included the uterus, urinary bladder, bowel and the lining of the bowel wall omentum forming new tumor growths before cancer is even suspected.

The five-year survival rate for all stages of ovarian cancer is 45.5%. For cases where a diagnosis is made early in the disease, when the cancer is still confined to the primary site, the five-year survival rate is 92.7%.

E. Brain Cancer

A brain tumor is an intracranial solid neoplasm, a tumor (defined as an abnormal growth of cells) within the brain or the central spinal canal. Brain tumors include all tumors inside the cranium or in the central spinal canal. They are created by an abnormal and uncontrolled cell division, normally either in the brain itself (neurons, glial cells (astrocytes, oligodendrocytes, ependymal cells, myelin-producing Schwann cells), lymphatic tissue, blood vessels), in the cranial nerves, in the brain envelopes (meninges), skull, pituitary and pineal gland, or spread from cancers primarily located in other organs (metastatic tumors).

Any brain tumor is inherently serious and life-threatening because of its invasive and infiltrative character in the limited space of the intracranial cavity. However, brain tumors (even malignant ones) are not invariably fatal. Brain tumors or intracranial neoplasms can be cancerous (malignant) or non-cancerous (benign); however, the definitions of malignant or benign neoplasms differs from those commonly used in other types of cancerous or non-cancerous neoplasms in the body. Its threat level depends on the combination of factors like the type of tumor, its location, its size and its state of development. Because the brain is well protected by the skull, the early detection of a brain tumor only occurs when diagnostic tools are directed at the intracranial cavity. Usually detection occurs in advanced stages when the presence of the tumor has caused unexplained symptoms.

Primary (true) brain tumors are commonly located in the posterior cranial fossa in children and in the anterior two-thirds of the cerebral hemispheres in adults, although they can affect any part of the brain.

The prognosis of brain cancer varies based on the type of cancer. Medulloblastoma has a good prognosis with chemotherapy, radiotherapy, and surgical resection while glioblastoma multiforme has a median survival of only 12 months even with aggressive chemoradiotherapy and surgery. Brainstem gliomas have the poorest prognosis of any form of brain cancer, with most patients dying within one year, even with therapy that typically consists of radiation to the tumor along with corticosteroids. However, one type of brainstem glioma, a focal[5] seems open to exceptional prognosis and long-term survival has frequently been reported.

Glioblastoma multiforme is the deadliest and most common form of malignant brain tumor. Even when aggressive multimodality therapy consisting of radiotherapy, chemotherapy, and surgical excision is used, median survival is only 12-17 months. Standard therapy for glioblastoma multiforme consists of maximal surgical resection of the tumor, followed by radiotherapy between two and four weeks after the surgical procedure to remove the cancer. This is followed by chemotherapy. Most patients with glioblastoma take a corticosteroid, typically dexamethasone, during their illness to palliate symptoms. Experimental treatments include gamma-knife radiosurgery, boron neutron capture therapy and gene transfer.

Oligodendroglioma is an incurable but slowly progressive malignant brain tumor. They can be treated with surgical resection, chemotherapy, and/or radiotherapy. For suspected low-grade oligodendrogliomas in select patients, some neuro-oncologists opt for a course of watchful waiting, with only symptomatic therapy. Tumors with the 1p/19q co-deletion have been found to be especially chemosensitive, and one source reports oligodendrogliomas to be among the most chemosensitive of human solid malignancies. A median survival of up to 16.7 years has been reported for low grade oligodendrogliomas.

Although there is no specific or singular clinical symptom or sign for any brain tumors, the presence of a combination of symptoms and the lack of corresponding clinical indications of infections or other causes can be an indicator to redirect diagnostic investigation towards the possibility of an intracranial neoplasm.

The diagnosis will often start with an interrogation of the patient to get a clear view of his medical antecedents, and his current symptoms. Clinical and laboratory investigations will serve to exclude infections as the cause of the symptoms. Examinations in this stage may include ophtamological, otolaryngological (or ENT) and/or electrophysiological exams. The use of electroencephalography (EEG) often plays a role in the diagnosis of brain tumors.

Swelling, or obstruction of the passage of cerebrospinal fluid (CSF) from the brain may cause (early) signs of increased intracranial pressure which translates clinically into headaches, vomiting, or an altered state of consciousness, and in children changes to the diameter of the skull and bulging of the fontanelles. More complex symptoms such as endocrine dysfunctions should alarm doctors not to exclude brain tumors.

A bilateral temporal visual field defect (due to compression of the optic chiasm) or dilatation of the pupil, and the occurrence of either slowly evolving or the sudden onset of focal neurologic symptoms, such as cognitive and behavioral impairment (including impaired judgment, memory loss, lack of recognition, spatial orientation disorders), personality or emotional changes, hemiparesis, hypoesthesia, aphasia, ataxia, visual field impairment, impaired sense of smell, impaired hearing, facial paralysis, double vision, or more severe symptoms such as tremors, paralysis on one side of the body hemiplegia, or (epileptic) seizures in a patient with a negative history for epilepsy, should raise the possibility of a brain tumor.

Imaging plays a central role in the diagnosis of brain tumors. Early imaging methods—invasive and sometimes dangerous—such as pneumoencephalography and cerebral angiography, have been abandoned in recent times in favor of non-invasive, high-resolution techniques, such as computed tomography (CT)-scans and especially magnetic resonance imaging (MRI). Neoplasms will often show as differently colored masses (also referred to as processes) in CT or MRI results.

Benign brain tumors often show up as hypodense (darker than brain tissue) mass lesions on cranial CT-scans. On MRI, they appear either hypo- (darker than brain tissue) or isointense (same intensity as brain tissue) on T1-weighted scans, or hyperintense (brighter than brain tissue) on T2-weighted MRI, although the appearance is variable.

Contrast agent uptake, sometimes in characteristic patterns, can be demonstrated on either CT or MRI-scans in most malignant primary and metastatic brain tumors. Perifocal edema, or pressure-areas, or where the brain tissue has been compressed by an invasive process also appears hyperintense on T2-weighted MRI might indicate the presence a diffuse neoplasm (unclear outline). This is because these tumors disrupt the normal functioning of the blood-brain barrier and lead to an increase in its permeability. However it is not possible to diagnose high versus low grade gliomas based on enhancement pattern alone.

Glioblastoma multiforme and anaplastic astrocytoma have been associated with the genetic acute hepatic porphyrias (PCT, AIP, HCP and VP), including positive testing associated with drug refractory seizures. Unexplained complications associated with drug treatments with these tumors should alert physicians to an undiagnosed neurological porphyria.

The definitive diagnosis of brain tumor can only be confirmed by histological examination of tumor tissue samples obtained either by means of brain biopsy or open surgery. The histological examination is essential for determining the appropriate treatment and the correct prognosis. This examination, performed by a pathologist, typically has three stages: interoperative examination of fresh tissue, preliminary microscopic examination of prepared tissues, and followup examination of prepared tissues after immunohistochemical staining or genetic analysis.

When a brain tumor is diagnosed, a medical team will be formed to assess the treatment options presented by the leading surgeon to the patient and his/her family. Given the location of primary solid neoplasms of the brain in most cases a "do-nothing" option is usually not presented. Neurosurgeons take the time to observe the evolution of the neoplasm before proposing a management plan to the patient and his/her relatives. These various types of treatment are available depending on neoplasm type and location and may be combined to give the best chances of survival: surgery: complete or partial ressection of the tumor with the objective of removing as many tumor cells as possible; radiotherapy; and chemotherapy, with the aim of killing as many as possible of cancerous cells left behind after surgery and of putting remaining tumor cells into a nondividing, sleeping state for as long as possible.

Survival rates in primary brain tumors depend on the type of tumor, age, functional status of the patient, the extent of surgical tumor removal and other factors specific to each case.

The primary and most desired course of action described in medical literature is surgical removal (resection) via craniotomy. Minimally invasive techniques are being studied but are far from being common practice. The prime remediating objective of surgery is to remove as many tumor cells as possible, with complete removal being the best outcome and cytoreduction ("debulking") of the tumor otherwise. In some cases access to the tumor is impossible and impedes or prohibits surgery.

Many meningiomas, with the exception of some tumors located at the skull base, can be successfully removed surgically. Most pituitary adenomas can be removed surgically, often using a minimally invasive approach through the nasal cavity and skull base (trans-nasal, trans-sphenoidal approach). Large pituitary adenomas require a craniotomy (opening of the skull) for their removal. Radiotherapy, including stereotactic approaches, is reserved for inoperable cases.

Several current research studies aim to improve the surgical removal of brain tumors by labeling tumor cells with a chemical (5-aminolevulinic acid) that causes them to fluoresce. Post-operative radiotherapy and chemotherapy are integral parts of the therapeutic standard for malignant tumors. Radiotherapy may also be administered in cases of "low-grade" gliomas, when a significant tumor burden reduction could not be achieved surgically.

Any person undergoing brain surgery may suffer from epileptic seizures. Seizures can vary from absences to severe tonic-clonic attacks. Medication is prescribed and administered to minimize or eliminate the occurrence of seizures.

Multiple metastatic tumors are generally treated with radiotherapy and chemotherapy rather than surgery. the prognosis in such cases is determined by the primary tumor, but is generally poor.

The goal of radiation therapy is to selectively kill tumor cells while leaving normal brain tissue unharmed. In standard external beam radiation therapy, multiple treatments of standard-dose "fractions" of radiation are applied to the brain. This process is repeated for a total of 10 to 30 treatments, depending on the type of tumor. This additional treatment provides some patients with improved outcomes and longer survival rates.

Radiosurgery is a treatment method that uses computerized calculations to focus radiation at the site of the tumor while minimizing the radiation dose to the surrounding brain. Radiosurgery may be an adjunct to other treatments, or it may represent the primary treatment technique for some tumors.

Radiotherapy may be used following, or in some cases in place of, resection of the tumor. Forms of radiotherapy used for brain cancer include external beam radiation therapy, brachytherapy, and in more difficult cases, stereotactic radiosurgery, such as Gamma knife, Cyberknife or Novalis Tx radiosurgery.

Radiotherapy is the most common treatment for secondary brain tumors. The amount of radiotherapy depends on the size of the area of the brain affected by cancer. Conventional external beam 'whole brain radiotherapy treatment' (WBRT) or 'whole brain irradiation' may be suggested if there is a risk that other secondary tumors will develop in the future. Stereotactic radiotherapy is usually recommended in cases involving fewer than three small secondary brain tumors.

Patients undergoing chemotherapy are administered drugs designed to kill tumor cells. Although chemotherapy may improve overall survival in patients with the most malignant primary brain tumors, it does so in only about 20 percent of patients. Chemotherapy is often used in young children instead of radiation, as radiation may have negative effects on the developing brain. The decision to prescribe this treatment is based on a patient's overall health, type of tumor, and extent of the cancer. The toxicity and many side effects of the drugs, and the uncertain outcome of chemotherapy in brain tumors puts this treatment further down the line of treatment options with surgery and radiation therapy preferred.

A shunt is used not as a cure but to relieve symptoms by reducing hydrocephalus caused by blockage of cerebrospinal fluid.

Researchers are presently investigating a number of promising new treatments including gene therapy, highly focused radiation therapy, immunotherapy and novel chemotherapies. A variety of new treatments are being made available on an investigational basis at centers specializing in brain tumor therapies.

F. Colorectal Cancer

Colorectal cancer, less formally known as bowel cancer, is a cancer characterized by neoplasia in the colon, rectum, or vermiform appendix. Colorectal cancer is clinically distinct from anal cancer, which affects the anus.

Colorectal cancers start in the lining of the bowel. If left untreated, it can grow into the muscle layers underneath, and then through the bowel wall. Most begin as a small growth on the bowel wall: a colorectal polyp or adenoma. These mushroom-shaped growths are usually benign, but some develop into cancer over time. Localized bowel cancer is usually diagnosed through colonoscopy.

Invasive cancers that are confined within the wall of the colon (TNM stages I and II) are often curable with surgery, For example, in England and Wales over 90% of patients diagnosed at this stage will survive the disease beyond 5 years. If left untreated, they spread to regional lymph nodes (stage III). In England and Wales, around 48% of patients diagnosed at this stage survive the disease beyond five years. Cancer that metastasizes to distant sites (stage IV) is usually not curable; approximately 7% of patients in England and Wales diagnosed at this stage survive beyond five years.

Colorectal cancer is the third most commonly diagnosed cancer in the world, but it is more common in developed countries. More than half of the people who die of colorectal cancer live in a developed region of the world. GLOBOCAN estimated that, in 2008, 1.23 million new cases of colorectal cancer were clinically diagnosed, and that this type of cancer killed more than 600,000 people.

The symptoms of colorectal cancer depend on the location of tumor in the bowel, and whether it has spread elsewhere in the body (metastasis). Most of the symptoms may occur in other diseases as well, and hence none of the symptoms mentioned here is diagnostic of colorectal cancer. Symptoms and signs are divided into local, constitutional (affecting the whole body) and metastatic (caused by spread to other organs).

Colorectal cancer is a disease originating from the epithelial cells lining the colon or rectum of the gastrointestinal tract, most frequently as a result of mutations in the Wnt signaling pathway that artificially increase signaling activity. The mutations can be inherited or are acquired, and must probably occur in the intestinal crypt stem cell. The most commonly mutated gene in all colorectal cancer is the APC gene, which produces the APC protein. The APC protein is a "brake" on the accumulation of β-catenin protein; without APC, β-catenin accumulates to high levels and translocates (moves) into the nucleus, binds to DNA, and activates the transcription of genes that are normally important for stem cell renewal and differentiation but when inappropriately expressed at high levels can cause cancer. While APC is mutated in most colon cancers, some cancers have increased β-catenin because of mutations in β-catenin (CTNNB1) that block its degradation, or they have mutation(s) or other genes with function analogous to APC such as AXIN1, AXIN2, TCF7L2, or the Naked cuticle (Nkd) gene NKD1.

Beyond the defects in the Wnt-APC-beta-catenin signaling pathway, other mutations must occur for the cell to become cancerous. The p53 protein, produced by the TP53 gene, normally monitors cell division and kills cells if they have Wnt pathway defects. Eventually, a cell line acquires a mutation in the TP53 gene and transforms the tissue from an adenoma into an invasive carcinoma.

Other apoptotic proteins commonly deactivated in colorectal cancers are TGF-β and DCC (Deleted in Colorectal Cancer). TGF-β has a deactivating mutation in at least half of colorectal cancers. Sometimes TGF-β is not deactivated, but a downstream protein named SMAD is. DCC commonly has deletion of its chromosome segment in colorectal cancer.

Some genes are oncogenes—they are overexpressed in colorectal cancer. For example, genes encoding the proteins KRAS, RAF, and PI3K, which normally stimulate the cell to divide in response to growth factors, can acquire mutations that result in over-activation of cell proliferation. PTEN, a tumor suppressor, normally inhibits PI3K, but can sometimes become mutated and deactivated.

Colorectal cancer can take many years to develop and early detection of colorectal cancer greatly improves the chances of a cure. The National Cancer Policy Board of the Institute of Medicine estimated in 2003 that even modest efforts to implement colorectal cancer screening methods would result in a 29 percent drop in cancer deaths in 20 years. Despite this, colorectal cancer screening rates remain low. Therefore, screening for the disease is recommended in individuals who are at increased risk. There are several different tests available for this purpose.

Digital rectal exam (DRE): The doctor inserts a lubricated, gloved finger into the rectum to feel for abnormal areas. It only detects tumors large enough to be felt in the distal part of the rectum but is useful as an initial screening test.

Fecal occult blood test (FOBT): a test for blood in the stool. Two types of tests can be used for detecting occult blood in stools, i.e., guaiac based (chemical test) and immunochemical. The sensitivity of immunochemical testing is superior to that of chemical testing without an unacceptable reduction in specifity.

Encoscopic diagnosis involves sigmoidoscopy, or use of a lighted probe (sigmoidoscope) is inserted into the rectum and lower colon to check for polyps and other abnormalities, or colonoscopy, which is use of a lighted probe called a colonoscope is inserted into the rectum and the entire colon to look for polyps and other abnormalities that may be caused by cancer. A colonoscopy has the advantage that if polyps are found during the procedure they can be removed immediately. Tissue can also be taken for biopsy. In the United States, colonoscopy or FOBT plus sigmoidoscopy are the preferred screening options.

Colon cancer staging is an estimate of the amount of penetration of a particular cancer. It is performed for diagnostic and research purposes, and to determine the best method of treatment. The systems for staging colorectal cancers depend on the extent of local invasion, the degree of lymph node involvement and whether there is distant metastasis.

Definitive staging can only be done after surgery has been performed and pathology reports reviewed. An exception to this principle would be after a colonoscopic polypectomy of a malignant pedunculated polyp with minimal invasion. Preoperative staging of rectal cancers may be done with endoscopic ultrasound. Adjunct staging of metastasis include Abdominal Ultrasound, CT, PET Scanning, and other imaging studies.

The most common staging system is the TNM (for tumors/nodes/metastases) system, from the American Joint Committee on Cancer (AJCC). The TNM system assigns a number based on three categories. "T" denotes the degree of invasion of the intestinal wall, "N" the degree of lymphatic node involvement, and "M" the degree of metastasis. The broader stage of a cancer is usually quoted as a number I, II, III, IV derived from the TNM value grouped by prognosis; a higher number indicates a more advanced cancer and likely a worse outcome.

The treatment depends on the stage of the cancer. When colorectal cancer is caught at early stages (with little spread), it can be curable. However, when it is detected at later stages (when distant metastases are present), it is less likely to be curable.

Surgery remains the primary treatment, while chemotherapy and/or radiotherapy may be recommended depending on the individual patient's staging and other medical factors.

Because colon cancer primarily affects the elderly, it can be a challenge to determine how aggressively to treat a particular patient, especially after surgery. Clinical trials suggest "otherwise fit" elderly patients fare well if they have adjuvant chemotherapy after surgery, so chronological age alone should not be a contraindication to aggressive management.

Surgeries can be categorised into curative, palliative, bypass, fecal diversion, or open-and-close. Curative surgical treatment can be offered if the tumor is localized. Very early cancer that develops within a polyp can often be cured by removing the polyp (i.e., polypectomy) at the time of colonoscopy.

In colon cancer, a more advanced tumor typically requires surgical removal of the section of colon containing the tumor with sufficient margins, and radical en-bloc resection of mesentery and lymph nodes to reduce local recurrence (i.e., colectomy). If possible, the remaining parts of colon are anastomosed to create a functioning colon. In cases when anastomosis is not possible, a stoma (artificial orifice) is created. Curative surgery on rectal cancer includes total mesorectal excision (lower anterior resection) or abdominoperineal excision.

In case of multiple metastases, palliative (noncurative) resection of the primary tumor is still offered to reduce further morbidity caused by tumor bleeding, invasion, and its catabolic effect. Surgical removal of isolated liver metastases is, however, common and may be curative in selected patients; improved chemotherapy has increased the number of patients who are offered surgical removal of isolated liver metastases.

If the tumor invaded into adjacent vital structures, which makes excision technically difficult, the surgeons may prefer to bypass the tumor (ileotransverse bypass) or to do a proximal fecal diversion through a stoma.

The worst case would be an "open-and-close" surgery, when surgeons find the tumor unresectable and the small bowel involved; any more procedures are thought by some to do more harm than good to the patient. This is uncommon with the advent of laparoscopy and better radiological imaging. Most of these cases formerly subjected to "open and close" procedures are now diagnosed in advance and surgery avoided.

Laparoscopic-assisted colectomy is a minimally invasive technique that can reduce the size of the incision and may reduce postoperative pain.

As with any surgical procedure, colorectal surgery may result in complications, including wound infection, dehiscence (bursting of wound) or hernia, anastomosis breakdown, leading to abscess or fistula formation, and/or peritonitis, bleeding with or without hematoma formation, adhesions resulting in bowel obstruction. A 5-year study of patients who had surgery in 1997 found the risk of hospital readmission to be 15% after panproctocolectomy, 9% after total colectomy, and 11% after ileostomy, adjacent organ injury; most commonly to the small intestine, ureters, spleen, or bladder, and cardiorespiratory complications, such as myocardial infarction, pneumonia, arrythmia, and pulmonary embolism.

Chemotherapy is used to reduce the likelihood of metastasis developing, shrink tumor size, or slow tumor growth. Chemotherapy is often applied after surgery (adjuvant), before surgery (neoadjuvant), or as the primary therapy (palliative). The treatments listed here have been shown in clinical trials to improve survival and/or reduce mortality rate, and have been approved for use by the US Food and Drug Administration. In colon cancer, chemotherapy after surgery is usually only given if the cancer has spread to the lymph nodes (Stage III).

Chemotherapy for metastatic disease. Commonly used first line chemotherapy regimens involve the combination of infusional 5-fluorouracil, leucovorin, and oxaliplatin (FOL-FOX) with bevacizumab or infusional 5-fluorouracil, leucovorin, and irinotecan (FOLFIRI) with bevacizumab or the same chemotherapy drug combinations with cetuximab in KRAS wild-type tumors.

At the 2008 annual meeting of the American Society of Clinical Oncology, researchers announced that colorectal cancer patients that have a mutation in the KRAS gene do not respond to certain therapies, those that inhibit the epidermal growth factor receptor (EGFR)—namely Erbitux (cetuximab) and Vectibix (panitumumab). Following recommendations by ASCO, patients should now be tested for the KRAS gene mutation before being offered these EGFR-inhibiting drugs. In July 2009, the US Food and Drug Administration (FDA) updated the labels of two anti-EGFR monoclonal antibody drugs (panitumumab (Vectibix) and cetuximab (Erbitux)) indicated for treatment of metastatic colorectal cancer to include information about KRAS mutations. However, having the normal KRAS version does not guarantee these drugs will benefit the patient.

Radiotherapy is not used routinely in colon cancer, as it could lead to radiation enteritis, and it is difficult to target specific portions of the colon. It is more common for radiation to be used in rectal cancer, since the rectum does not move as much as the colon and is thus easier to target.

According to the American Cancer Society statistics in 2006, over 20% of patients present with metastatic (stage IV) colorectal cancer at the time of diagnosis, and up to 25% of this group will have isolated liver metastasis that is potentially resectable. Lesions which undergo curative resection have demonstrated 5-year survival outcomes now exceeding 50%.

Resectability of a liver metastasis is determined using preoperative imaging studies (CT or MRI), intraoperative ultrasound, and by direct palpation and visualization during resection. Lesions confined to the right lobe are amenable to en bloc removal with a right hepatectomy (liver resection) surgery. Smaller lesions of the central or left liver lobe may sometimes be resected in anatomic "segments", while large lesions of left hepatic lobe are resected by a procedure called hepatic trisegmentectomy. Treatment of lesions by smaller, nonanatomic "wedge" resections is associated with higher recurrence rates. Some lesions which are not initially amenable to surgical resection may become candidates if they have significant responses to preoperative chemotherapy or immunotherapy regimens. Lesions which are not amenable to surgical resection for cure can be treated with modalities including radio-frequency ablation (RFA), cryoablation, and chemoembolization.

Patients with colon cancer and metastatic disease to the liver may be treated in either a single surgery or in staged surgeries (with the colon tumor traditionally removed first) depending upon the fitness of the patient for prolonged surgery, the difficulty expected with the procedure with either the colon or liver resection, and the comfort of the surgery performing potentially complex hepatic surgery.

A study published in 2009 found that aspirin reduces risk of colorectal neoplasia in randomized trials, and inhibits tumor growth and metastases in animal models. The influence of aspirin on survival after diagnosis of colorectal cancer is unknown. Several reports, including a prospective cohort of 1,279 people diagnosed with stages I-III (non-metastatic) colorectal cancer, have suggested a significant improvement in cancer-specific survival in a subset of patients using aspirin.

Cimetidine is being investigated in Japan as an adjuvant for adenocarcinomas, including for stage III and stage IV colorectal cancers biomarked with overexpressed sialyl Lewis X and A epitopes. Multiple small trials suggest a significant survival improvement in the subset of patients with the sLeX and sLeA biomarkers that take cimetidine treatment perioperatively, through several mechanisms.

Cancer diagnosis very often results in an enormous change in the patient's psychological wellbeing. Various support resources are available from hospitals and other agencies, which provide counseling, social service support, cancer support groups, and other services. These services help to mitigate some of the difficulties of integrating patients' medical complications into other parts of their lives.

G. Benign Prostatic Hyperplasia

Benign prostatic hyperplasia (BPH) also known as benign prostatic hypertrophy (technically a misnomer), benign enlargement of the prostate (BEP), and adenofibromyomatous hyperplasia, refers to the increase in size of the prostate.

To be accurate, the process is one of hyperplasia rather than hypertrophy, but the nomenclature is often interchangeable, even amongst urologists. It is characterized by hyperplasia of prostatic stromal and epithelial cells, resulting in the formation of large, fairly discrete nodules in the periurethral region of the prostate. When sufficiently large, the nodules compress the urethral canal to cause partial, or sometimes virtually complete, obstruction of the urethra, which interferes the normal flow of urine. It leads to symptoms of urinary hesitancy, frequent urination, dysuria (painful urination), increased risk of urinary tract infections, and urinary retention. Although prostate specific antigen levels may be elevated in these patients because of increased organ volume and inflammation due to urinary tract infections, BPH is not considered to be a premalignant lesion.

Adenomatous prostatic growth is believed to begin at approximately age 30 years. An estimated 50% of men have histologic evidence of BPH by age 50 years and 75% by age 80 years. In 40-50% of these patients, BPH becomes clinically significant.

Benign prostatic hyperplasia symptoms are classified as storage or voiding. Storage symptoms include urinary frequency, urgency (compelling need to void that cannot be deferred), urgency incontinence, and voiding at night (nocturia). Voiding symptoms include urinary stream, hesitancy (needing to wait for the stream to begin), intermittency (when the stream starts and stops intermittently), straining to void, and dribbling. Pain and dysuria are usually not present. These storage and voiding symptoms are evaluated using the International Prostate Symptom Score (IPSS) questionnaire, designed to assess the severity of BPH.

BPH can be a progressive disease, especially if left untreated. Incomplete voiding results in stasis of bacteria in the bladder residue and an increased risk of urinary tract infection. Urinary bladder stones are formed from the crystallization of salts in the residual urine. Urinary retention, termed acute or chronic, is another form of progression. Acute urinary retention is the inability to void, while in chronic urinary retention the residual urinary volume gradually increases, and the bladder distends. Some patients that suffer from chronic urinary retention may eventually progress to renal failure, a condition termed obstructive uropathy.

Androgens (testosterone and related hormones) are considered to play a permissive role in BPH by most experts. This means that androgens have to be present for BPH to occur, but do not necessarily directly cause the condition. This is supported by the fact that castrated boys do not develop BPH when they age. On the other hand, administering exogenous testosterone is not associated with a significant increase in the risk of BPH symptoms. Dihydrotestosterone (DHT), a metabolite of testosterone, is a critical mediator of prostatic growth. DHT is synthesized in the prostate from circulating testosterone by the action of the enzyme 5α-reductase, type 2. This enzyme is localized principally in the stromal cells; hence, those cells are the main site for the synthesis of DHT.

DHT can act in an autocrine fashion on the stromal cells or in paracrine fashion by diffusing into nearby epithelial cells. In both of these cell types, DHT binds to nuclear androgen receptors and signals the transcription of growth factors that are mitogenic to the epithelial and stromal cells. DHT is 10 times more potent than testosterone because it dissociates from the androgen receptor more slowly. The importance of DHT in causing nodular hyperplasia is supported by clinical observations in which an inhibitor of 5α-reductase is given to men with this condition. Therapy with 5α-reductase inhibitor markedly reduces the DHT content of the prostate and, in turn, reduces prostate volume and, in many cases, BPH symptoms.

Testosterone promotes prostate cell proliferation, but relatively low levels of serum testosterone are found in patients with BPH. One small study has shown that medical castration lowers the serum and prostate hormone levels unevenly, having less effect on testosterone and dihydrotestosterone levels in the prostate.

While there is some evidence that estrogen may play a role in the etiology of BPH, this effect appears to be mediated mainly through local conversion of estrogen to androgens in the prostate tissue rather than a direct effect of estrogen itself. In canine in vivo studies castration, which significantly reduced androgen levels but left estrogen levels unchanged, caused significant atrophy of the prostate. Studies looking for a correlation between prostatic hyperplasia and serum estrogen levels in humans have generally shown none.

On a microscopic level, BPH can be seen in the vast majority of men as they age, in particular over the age of 70 years, around the world. However, rates of clinically significant, symptomatic BPH vary dramatically depending on lifestyle. Men that lead a western lifestyle have a much higher incidence of symptomatic BPH than men that lead a traditional or rural lifestyle. This is confirmed by research in China showing that men in rural areas have very low rates of clinical BPH, while men living in cities adopting a western lifestyle have a skyrocketing incidence of this condition, though it is still below rates seen in the West.

Rectal examination (palpation of the prostate through the rectum) may reveal a markedly enlarged prostate, usually affecting the middle lobe. Often, blood tests are performed to rule out prostatic malignancy: Elevated prostate specific antigen (PSA) levels needs further investigations such as reinterpretation of PSA results, in terms of PSA density and PSA free percentage, rectal examination and transrectal ultrasonography. These combined measures can provide early detection. Ultrasound examination of the testicles, prostate, and kidneys is often performed, again to rule out malignancy and hydronephrosis. Screening and diagnostic procedures for BPH are similar to those used for prostate cancer Medication is often prescribed as the first treatment option, there are many patients who do not achieve success with this line of treatment. Those patients may not achieve sustained improvement in symptoms or they may stop taking the medication because of side-effects. There are options for treatment in a urologist's office before proceeding to surgery. The two most common types of office-based therapies are transurethral microwave thermotherapy (TUMT) and transurethral needle ablation (TUNA). Both of these procedures rely on delivering enough energy to create sufficient heat to cause cell death (necrosis) in the prostate. The goal of the therapies is to cause enough necrosis so that, when the dead tissue is reabsorbed by the body, the prostate shrinks, relieving the obstruction of the urethra. These procedures are typically performed with local anesthesia, and the patient returns home the same day. Some urologists have studied and published long-term data on the outcomes of these procedures, with data out to five years. The most recent American Urological Association (AUA) Guidelines for the Treatment of BPH in 2003 lists minimally invasive therapies including TUMT and TUNA as acceptable alternatives for certain patients with BPH.

Transurethral microwave therapy (TUMT) was originally approved by the FDA in 1996, with the first generation system by EDAP Technomed. Since 1996, other companies have received FDA approval for TUMT devices, including Urologix, Dornier, Thermatrix, Celsion, and Prostalund. Multiple clinical studies have been published on TUMT. The general principle underlying all the devices is that a microwave antenna that resides in a urethral catheter is placed in the intraprostatic area of the urethra. The catheter is connected to a control box outside of the patient's body and is energized to emit microwave radiation into the prostate to heat the tissue and cause necrosis. It is a one-time treatment that takes approximately 30 minutes to 1 hour, depending on the system used. It takes approximately 4 to 6 weeks for the damaged tissue to be reabsorbed into the patient's body. Some of the devices incorporate circulating coolant through the treatment area with the intent of preserving the urethra while the microwave energy heats the prostatic tissue surrounding the urethra.

Transurethral needle ablation (TUNA) operates with a different type of energy, radio frequency (RF) energy, but is designed along the same premise as TUMT devices, that the heat the device generates will cause necrosis of the prostatic tissue and shrink the prostate. The TUNA device is inserted into the urethra using a rigid scope much like a cystoscope. The energy is delivered into the prostate using two needles that emerge from the sides of the device, through the urethral wall and into the prostate. The needle-based ablation devices are very effective at heating a localized area to a high enough temperature to cause necrosis. The treatment is typically performed in one session, but may require multiple sticks of the needles depending on the size of the prostate.

If medical treatment fails, and the patient elects not to try office-based therapies or the physician determines the patient is a better candidate for transurethral resection of prostate (TURP), surgery may need to be performed. In general, TURP is still considered the gold standard of prostate interventions for patients that require a procedure. This involves removing (part of) the prostate through the urethra. There are also a number of new methods for reducing the size of an enlarged prostate, some of which have not been around long enough to fully establish their safety or side-effects. These include various methods to destroy or remove part of the excess tissue while trying to avoid damaging what remains. Transurethral electrovaporization of the prostate (TVP), laser TURP, visual laser ablation (VLAP), ethanol injection, and others are studied as alternatives.

Newer techniques involving lasers in urology have emerged in the last 5-10 years, starting with the VLAP technique involving the Nd:YAG laser with contact on the prostatic tissue. A similar technology called Photoselective Vaporization of the Prostate (PVP) with the GreenLight (KTP) laser have emerged very recently. This procedure involves a high-power 80-watt KTP laser with a 550-micrometre laser fiber inserted into the prostate. This fiber has an internal reflection with a 70-degree deflecting angle. It is used to vaporize the tissue to the prostatic capsule. KTP lasers target haemoglobin as the chromophore and typically have a penetration depth of 2.0 mm (four times deeper than holmium).

Another procedure termed Holmium Laser Ablation of the Prostate (HoLAP) has also been gaining acceptance around the world. Like KTP, the delivery device for HoLAP procedures is a 550 um disposable side-firing fiber that directs the beam from a high-power 100-watt laser at a 70-degree angle from the fiber axis. The holmium wavelength is 2,140 nm, which falls within the infrared portion of the spectrum and is invisible to the naked eye. Whereas KTP relies on haemoglobin as a chromophore, water within the target tissue is the chromophore for Holmium lasers. The penetration depth of Holmium lasers is <0.5 mm, avoiding complications associated with tissue necrosis often found with the deeper penetration and lower peak powers of KTP.

HoLEP, Holmium Laser Enucleation of the Prostate, is another Holmium laser procedure reported to carry fewer risks compared with either TURP or open prostatectomy. HoLEP is largely similar to the HoLAP procedure; the main difference is that this procedure is typically performed on larger prostates. Instead of ablating the tissue, the laser cuts a portion of the prostate, which is then cut into smaller pieces and flushed with irrigation fluid. As with the HoLAP procedure, there is little bleeding during or after the procedure.

Both wavelengths, KTP and Holmium, ablate approximately one to two grams of tissue per minute.

III. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

RESULTS

Since AR signaling may require LXXLL structural motifs, the inventors initially evaluated LXXLL structural motifs on PELP1 as potential targets. PELP1 contains 10 such LXXLL motifs that adopt a helical structure when it is bound to nuclear receptors. The rigid and pre-organized structure of a tris-benzamide facilitates the placement of 3 functional groups corresponding to the amino acids found at the i, i+4, and i+7 positions in an α-helix. Conversely, a bis-benzamide scaffold can present 2 side chains of the amino acids found at the i and i+4 positions by using its 2 substituents ($R_{1-2}$). The inventors decided to design their initial peptidomimetic as a generic LXXXL peptidomimetic to potentially target all 10 PELP1 LXXLL motifs. The design of the initial peptidomimetic utilized a Monte Carlo conformational search (5,000 steps) using a MM3 force field implemented into the software, and showed that 2 functional groups ($R_{1-2}$) in the lowest-energy conformation are well overlaid on the corresponding side chains of a helix. The functional organization and presentation of these leucines on one side of a helix was confirmed by molecular modeling using MacroModel (version 9, Schrödinger, New York, N.Y.).

X-ray crystal structure of a short peptide derived from an LXXLL sequence bound to AR showed that the LXXLL motif adopts an α-helical structure and the side chains of the three leucines at the i, i+3, and i+4 positions interact with the hydrophobic pocket in the AF2 domain of AR (FIG. 4A). Since the rigid and pre-organized structure of a bis-benzamide scaffold can place two substituents as the side chains of the amino acid residues at the i and i+4 positions of a helix appear, the inventors designed bis-benzamide-based peptidomimetics to potentially target all ten LXXLL motifs in PELP1. The design of the LXXLL peptidomimetics also allows the blockade of interaction between AR and other cofactor proteins that interact with AR through this nuclear receptor box.

Figure 5:
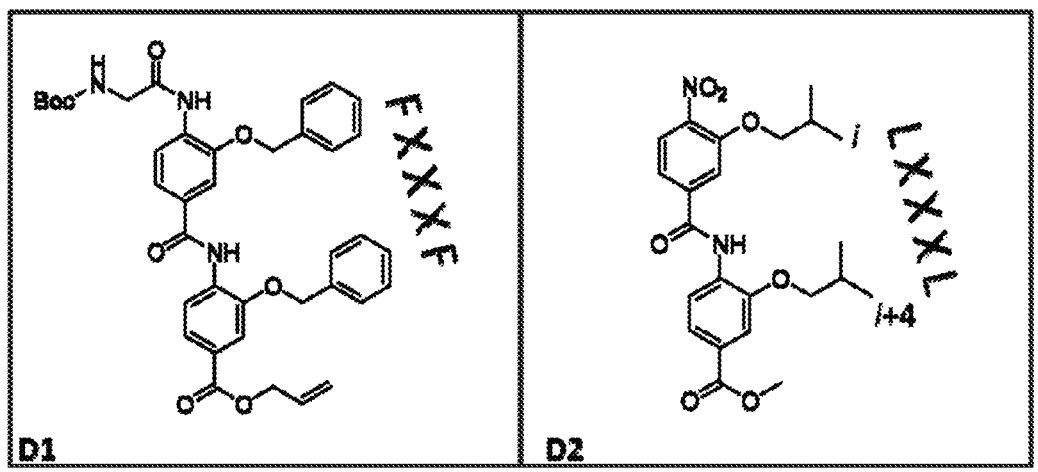
FIG. 5. Two isobutyl groups of the bis-benzamide D2 was designed to mimic the side chains of the two leucines at the i and i+4 positions of the LXXLL motif, organizing hydrophobic surface for AR interaction. On the other hand, a bis-benzamide containing two benzyl groups (D1) was synthesized as a control FIG. 6. Effect of D1 and D2 on DHT induced AR-PELP1 co-immunoprecipitation in LNCaP cells.

Two isobutyl groups of the bis-benzamide D2 was designed to mimic the side chains of the two leucines at the i and i+4 positions of the LXXLL motif, organizing hydrophobic surface for AR interaction. As shown in FIG. 4D, the lowest energy conformation demonstrated that the two isobutyl groups in D2 were well overlaid over the side chains of two leucines. The initial compound was the bis-benzamide D2, which has two 2 isobutyl groups to emulate the side chain groups of 2 Leu at the i and i+4 position of the LXXLL motif, whereas a control D1 contains 2 benzyl groups (FIG. 5). On the other hand, a bis-benzamide containing two benzyl groups (D1) was synthesized as a control (FIG. 5). Two isobutyl groups of the bis-benzamide D2 was designed to mimic the side chains of the two leucines at the i and i+4 positions of the LXXLL motif, organizing hydrophobic surface for AR interaction. On the other hand, a bis-benzamide containing two benzyl groups (D1) was synthesized as a control (FIG. 5).

The LXXLL peptidomimetic D2 was stable in DMSO at room temperature and −70° C. over a long period of storage (60 days). Besides the long shelf life, D2 was remarkably found to be stable in cell lysate of LNCaP over 7 days (FIGS. 4E-F).

Figure 6:
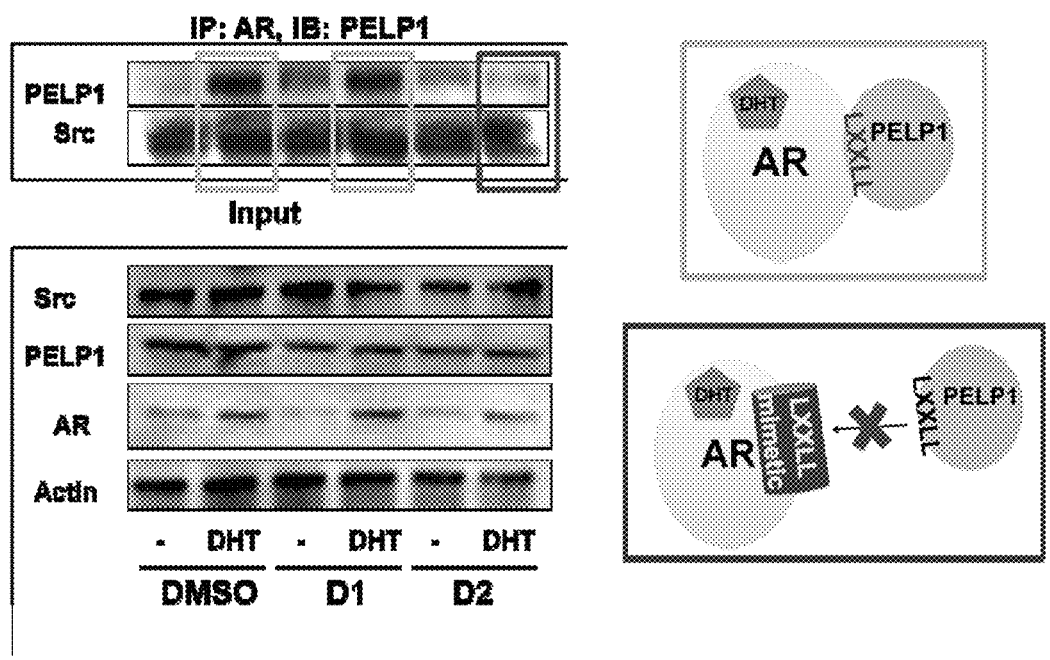

FIG. 6 provides confirmation that D2 was directed against the LXXLL motif and was capable of blocking AR and PELP1 interaction in vivo was obtained from coimmunoprecipitation experiments in LnCaP PCa cells. Preincubation of PCa cells with 100 nM D2, but not D1, blocked the ability of DHT-induced AR and PELP1 to physically interact with each other.

Figure 7:
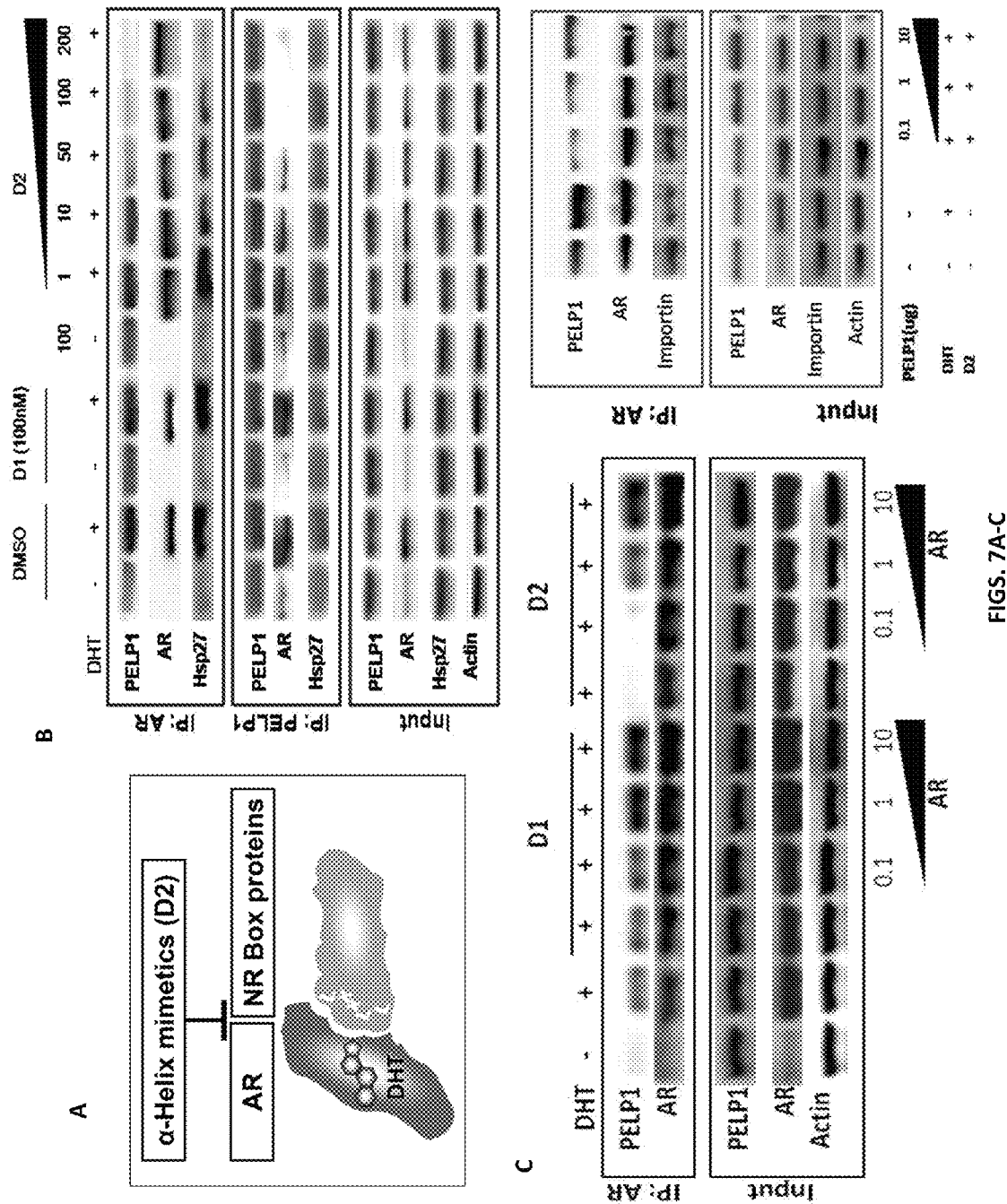
FIGS. 7A-C. Effect of D1 and D2 on DHT induced AR-PELP1 co-immunoprecipitation in LNCaP cells.

FIG. 7 shows that D2 blocked AR-PELP1 interaction in a dose-dependent manner. D2 was also able to block the DHT- and E2-induced interaction of AR with PELP1 in LAPC4, C4-2, VCAP and CWR22v1 cells. D2 did not adversely affect the stability of either AR or PELP1. D2 was not able to affect the interaction between AR and hsp90, a protein that lacks a LXXLL motif on its primary structure. The ability of D2 to block AR-PELP1 interaction could be overcome by transient over-expression of PELP1 in a dose-dependent manner.

Figure 8:
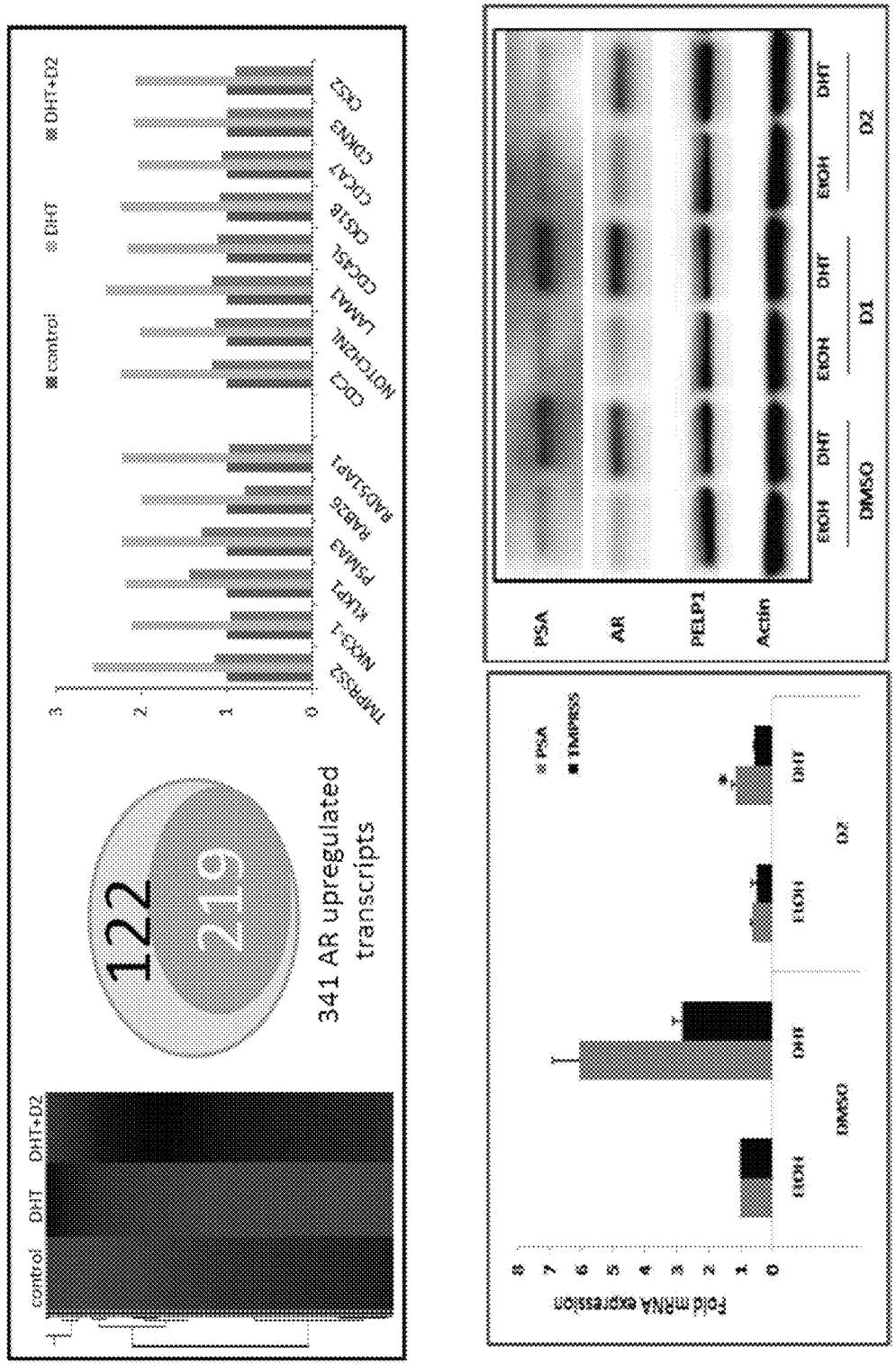
FIG. 8. Effect of D2 on DHT-induced transcription: RNA from LNCaP cells untreated or treated with DHT in the absence and presence of D2 were evaluated by the Illumina platform for DHT-regulated transcripts. The heat map shows the basal level of expression in (light grey) and upregulated genes by DHT (dark grey). Expression levels of selected genes are shown in the right panel, including AR-regulated genes and those involved in cell proliferation.

FIG. 8 confirms these findings by QPCR experiment evaluating the effect of D1 and D2 on DHT-induced TMPRSS and PSA gene expression at the RNA level in LNCaP cells (bottom left panel) and by western blot analyses as evaluated by the effect of D1 and D2 on the expression of PSA, androgen receptor and actin in LAPC4 cells at the protein level. Of the 341 transcripts significantly upregulated by DHT, pretreatment with D2 reduced the expression level of 219 genes back to baseline. Confirmation of these findings were obtained by QPCR and western blot analyses.

Figure 9:
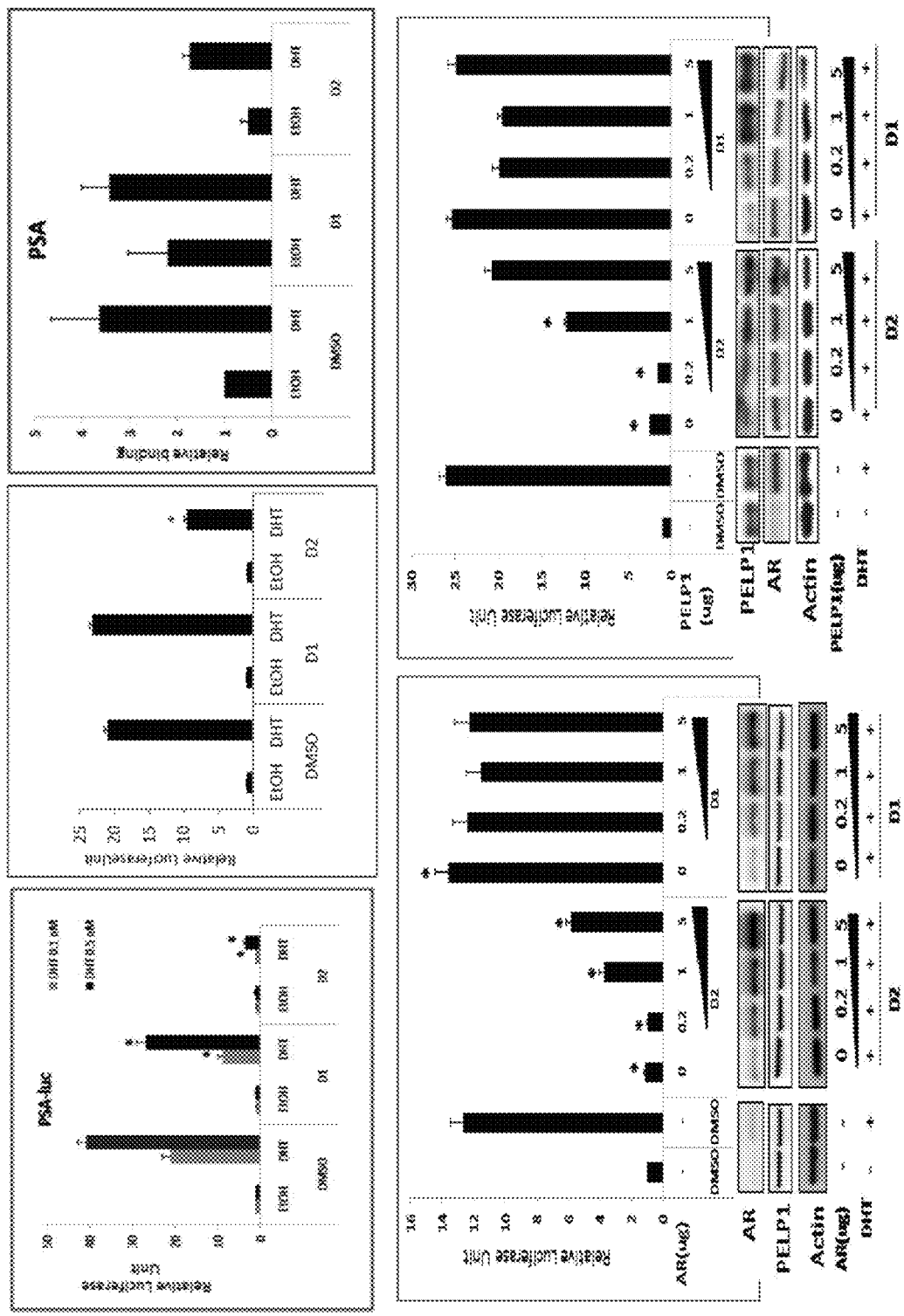
FIG. 9. D2 can block DHT-induced gene expression. The ability of D2 but not D1 to block DHT-Induced gene expression was noted by transcription from a PSA-luciferase promoter (top left panel), from an ARE-luciferase reporter (top middle panel). D2 blocked AR binding to its cognate DNA sequence on the PSA promoter on CHIP assays (top right panel). This effect of D2 could be rescued by overexpression of AR (bottom left panel) or PELP1 (bottom right panel).

FIG. 9 demonstrates that D2 was able to block DHT-induced transcription from an PSA-luciferase promoter in LAPC4 cells or from a minimal ARE-luciferasereporter in LNCaP, CWR22v1 and LAPC4 cell lines. The ability of D2 to block DHT-induced transcription from ARE-driven promoters was confirmed at the RNA level using QPCR evaluation of both the PSA and TMPRSS promoter. Further, D2 blocked DHT-induced AR binding on PSA promoter at evidenced by CHiP assays. At the protein level, D2, but not D1, was able to block DHT-induced expression of PSA protein. Again, the suppresion of DHT-induced transcription from an ARE could be overcome by overexpression of either AR or PELP1 (FIG. 4). Overexpression of PELP1 was able to rescue the D2-mediated suppression of DHT-induced transcription nearly back to baseline. These data indicated that D2 can block AR genomic signaling, at least in part by blocking AR-PELP1 interaction.

Figure 10:
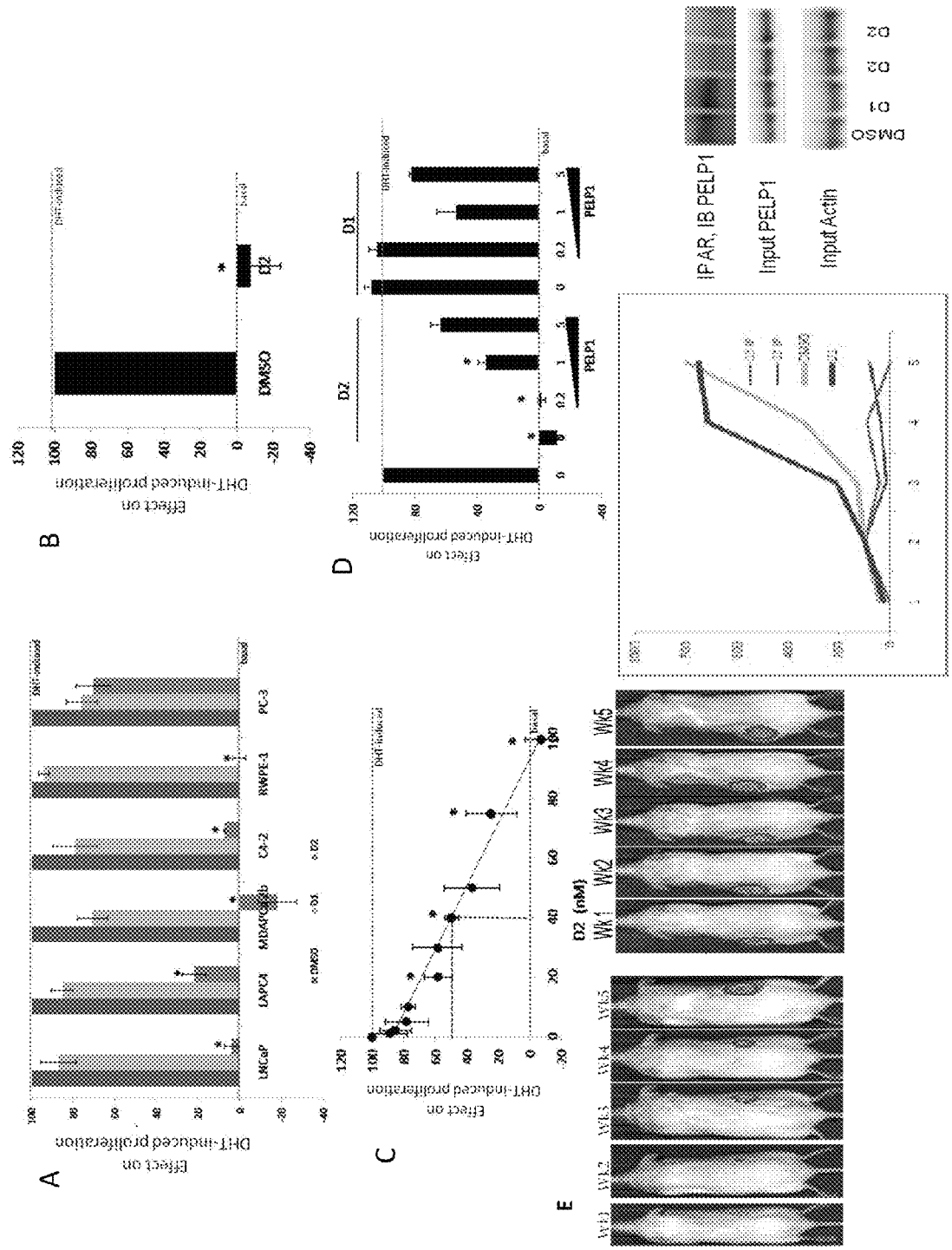
FIGS. 10A-E. D2 blocks proliferation of prostate cancer cells in vitro and in vivo (a) Effect of pretreatment with 100 nM of D1 and D2 on DHT-induced proliferation in multiple prostate cancer cell lines in MTT assay. Numbers are normalized to a baseline of 100, which represents the untreated rate of proliferation. (b) Effect of pretreatment with 100 nM of D1 and D2 on DHT-induced proliferation in LNCaPcells on a Cyquant assay. (c) Dose dependent curve of D2 on proliferation of LAPC4 cells. (d) Rescue of DHT induced proliferation by overexpression of PELP1 following suppression of DHT induced proliferation with 100 nM of D2. (e). Effect of direct intratumoral injections of D1 and D2 on the proliferation of prostate cancer xenografts in animal models: Following establishment of subcutaneous xenografts in animal models, daily direct intratumoral injections of D1 and D2 were performed. Bioluminesence imaging was used to track the growth of the tumors and the effect of D1 and D2 quantitated as shown in the graph. Evaluation of the protein extracts from these tumors revealed that D2 was able to block AR-PELP1 complex formation in the xenograft tumors.

Pretreatment with D2 prevented the DHT-induced proliferation of a variety of PCa cell lines that contain AR, such as LNCaP, LAPC4, C4-2, RWPE-1, CWR22v1, VCaP, MDAPCa 2b but not AR-negative PCa cell lines such as DU145 or PC3 whereas the control D1 did not show any activity (FIG. 10). These data were confirmed using BrdU assays (CyQuant). D2 was able to significantly reduce DHT-mediated proliferation of PCa cells in vitro in dose-dependent manner ($IC_{50}$ ~40 nM) in MTT assays. The importance of PELP1 and AR interaction on DHT-mediated proliferation of prostate cancer cells were confirmed using rescue experiments, where D2 suppression of DHT-mediated proliferation was overcome by overexpression of PELP1 in LNCaP PCa cells. Finally, the effect in xenografts showed that D2 was biologically active in blocking AR-PELP1 interaction even in vivo models.

Figure 11:
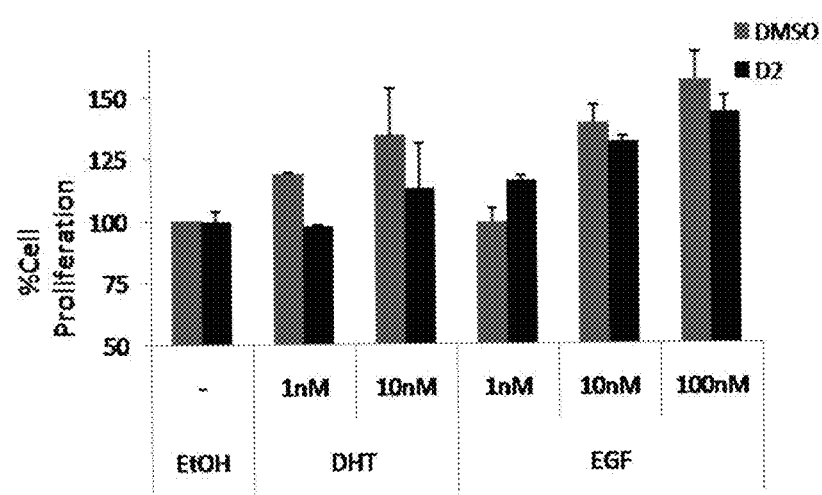
FIG. 11. Specificity of D2 effect on proliferation: D2 does not affect EGF or LPA mediated proliferation of prostate cancer cells. D2 does block DHT-induced proliferation of prostate cancer cells.

As shown in FIG. 11, the effect of D2 on steroid-induced proliferation pathways appears to be specific, as D2 had no effect on EGF or LPA-induced proliferation of PCa cells. In this experiment, cells were plated (2-10×103/well) in 96 well plates and subjected to androgen deprivation for 48 hours with phenol-red free RPMI and 1% charcoal stripped fetal bovine serum (CSF). Cells were then treated with either ethanol, EGF or DHT as a positive control for 48 hours. Peptidomimetics were added 2 hours prior to treatment. Cell proliferation was measured using the MTT colorimetric assay. All experiments were performed in triplicate and the average of experiments displayed.

Figure 12:
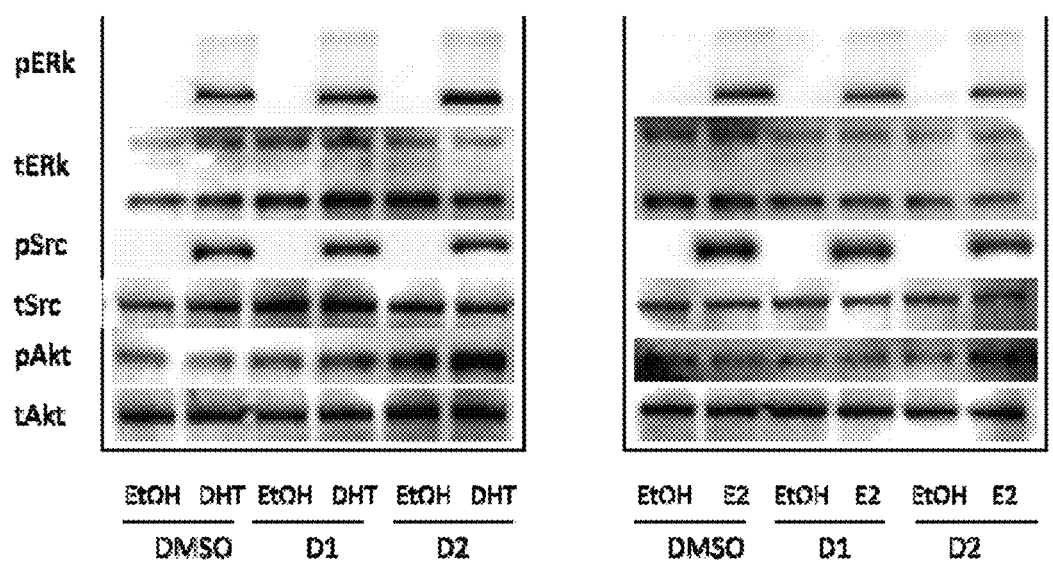
FIG. 12. D2 does not block the non-genomic activation of erk by DHT.
Figure 13:
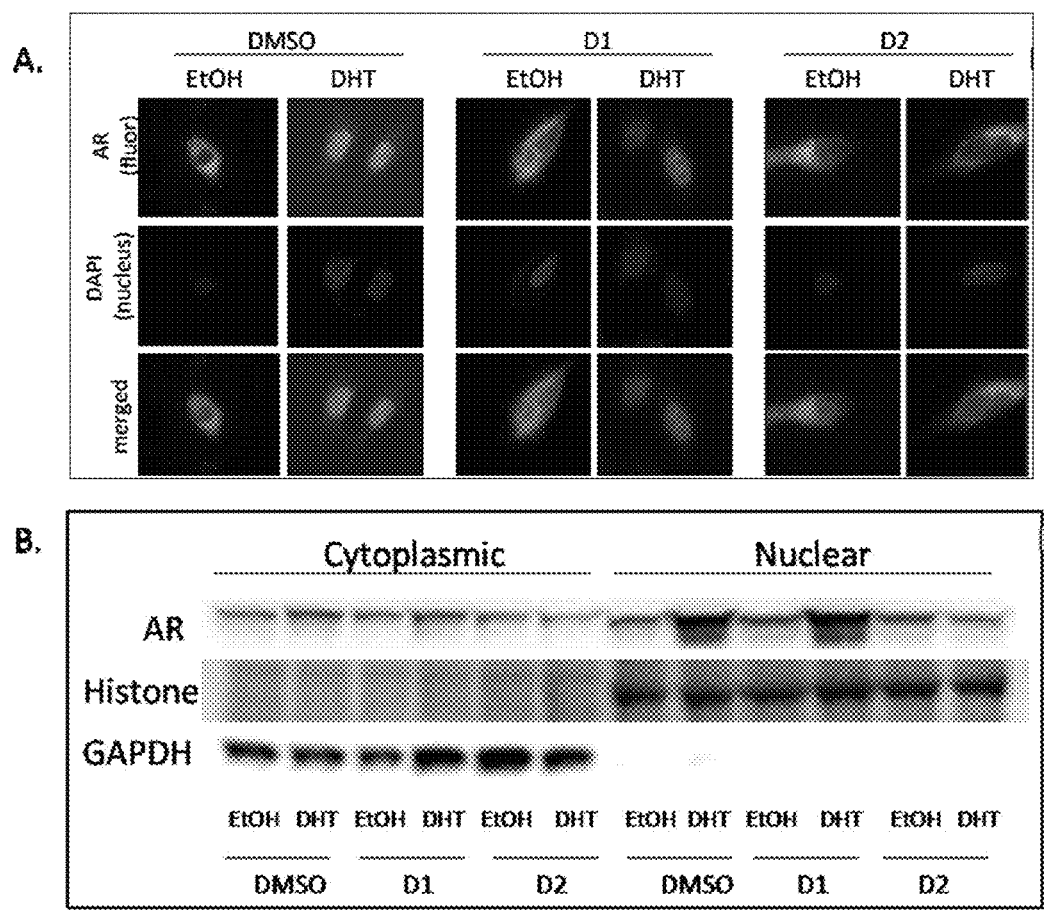
FIGS. 13A-B. Effect on DHT-induced nuclear translocation of exogenous AR-GFP in LNCaP cells transiently transfected with AR. (a) Blue stain is DAPI (for nucleus) and green is AR (GFP). Baseline untreated LNCaP cells are shown in top left panel. Cells were pretreated with DMSO (left panel), 100 nM D1 (middle panel) and 100 nM D2 (right panel) and then treated with InM DHT. AR nuclear translocation was visualized at 4 hours following DHT treatment. (b) Nuclear and cytoplasmic extracts were collected from similar cells and subject to western analyses.

FIG. 12 shows the effect of D2 on DHT-induced genomic activation was specific, as D2 had no effect on DHT-mediated non-genomic activation of erk. FIG. 13 shows that pretreatment with D2 blocked DHT-induced translocation of AR-GFP to the nucleus in LnCaP cells compared to the control D1 or DMSO. These findings were confirmed with biochemical analyses of the nuclear and cytoplasmic extracts from LnCaP cells, which revealed that pretreatment with D2, but not D1 or DMSO, prevents AR nuclear translocation upon addition of DHT. These data are further corroborated by evaluations of the endogenous AR in LAPC4 cells.

Figure 14:
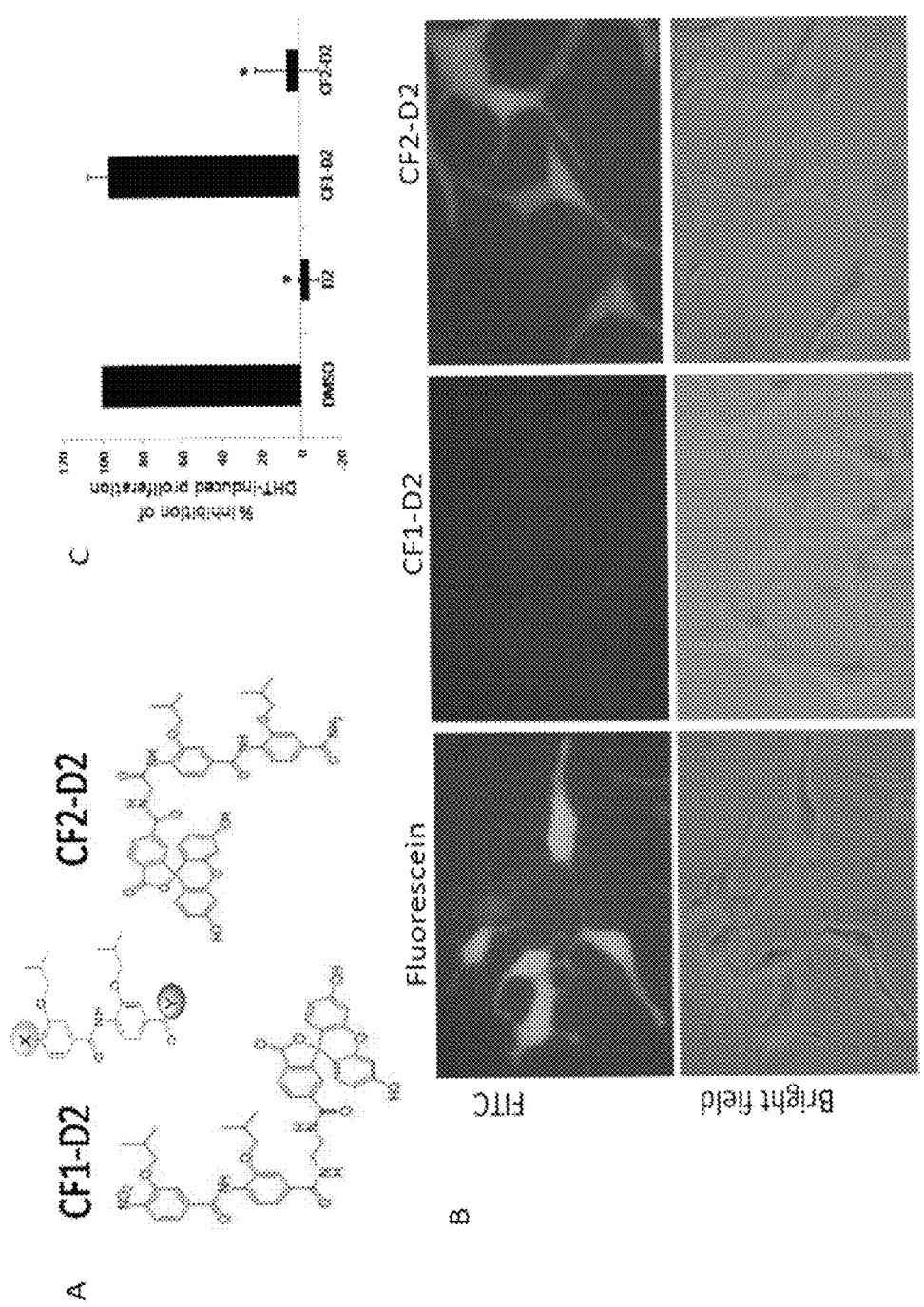
FIGS. 14A-C. Effect of chemical conjugation of Fluorescein to D2 at the amino and carboxy terminus (FIG. 14A) on uptake by LnCaP cells at 4 hours (FIG. 14B) and on DHT-induced proliferation of PCa cells (FIG. 14C).
Figure 15:
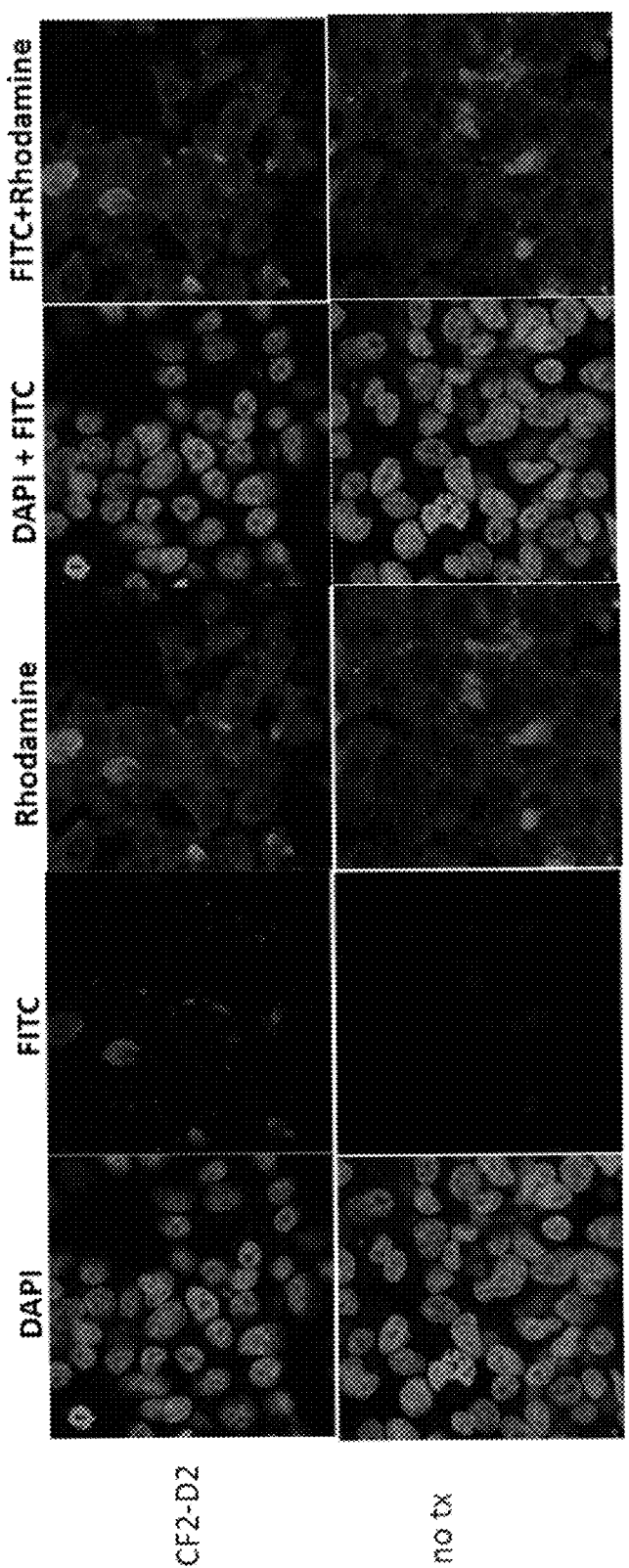
FIG. 15. CF2D2 can get into the cell. Evidence obtained by confocal microscopy reveals that CF2D2 can widely get into the cell upon treatment. Background autofluorescene in C4-2 cells is minimal as evidenced by the no treatment group.
Figure 16:
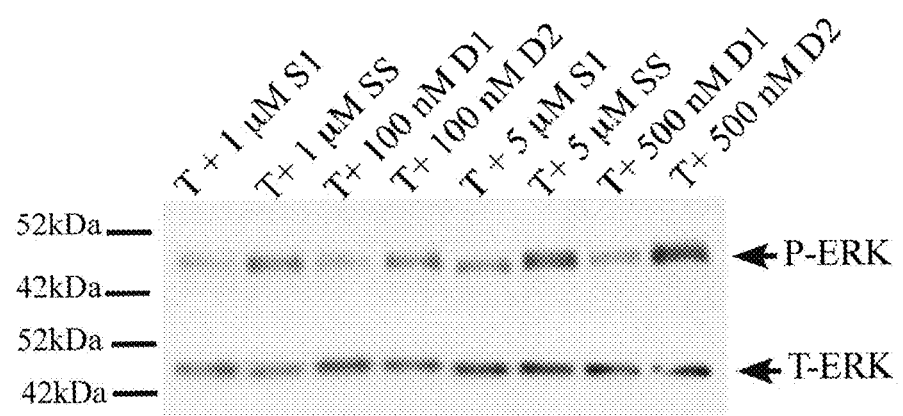
FIG. 16. Evidence for utility of higher concentrations of D1 in blocking erk phosphorylation: following serum starvation, cells were treated with either D1 or D2 and assessed for their ability to block erk phosphorylation. D1 blocks erk phosphorylation.

In FIG. 14, two fluorescent analogues of D2 were prepared, one by introducing a fluorescein moiety to the C-terminus of D2 (CF1-D2) and the other by placing it at the N-terminus (CF2-D2). Following incubation with these fluorescent analogues, CF2-D2, but not CF1-D2, was shown to enter LNCaP cells. As a result, CF2-D2, but not CF1-D2, was able to block DHT-induced proliferatin of PCa cells. These data confirm that the peptidomimetic D2 functions by entering the PCa cells and that when the peptidomimetic does not enter the cell, it has no ability to block AR signaling. FIG. 15 shows confocal studies confirming that the peptidomimetic CF2-D2 functions by entering the PCa cells and is widely localized within the cell In FIG. 16, at higher concentrations (500 nM) D1 blocks erk activation in western blot analyses, whereas D2 blocks at lower concentrations. D2, and to a less extent D1, targets a validated target in prostate cancer, has the potential to be an AR-selective modulator, provides a novel mechanism of action, and will likely provide a sustained effect in the context of therapy.

Figure 17:
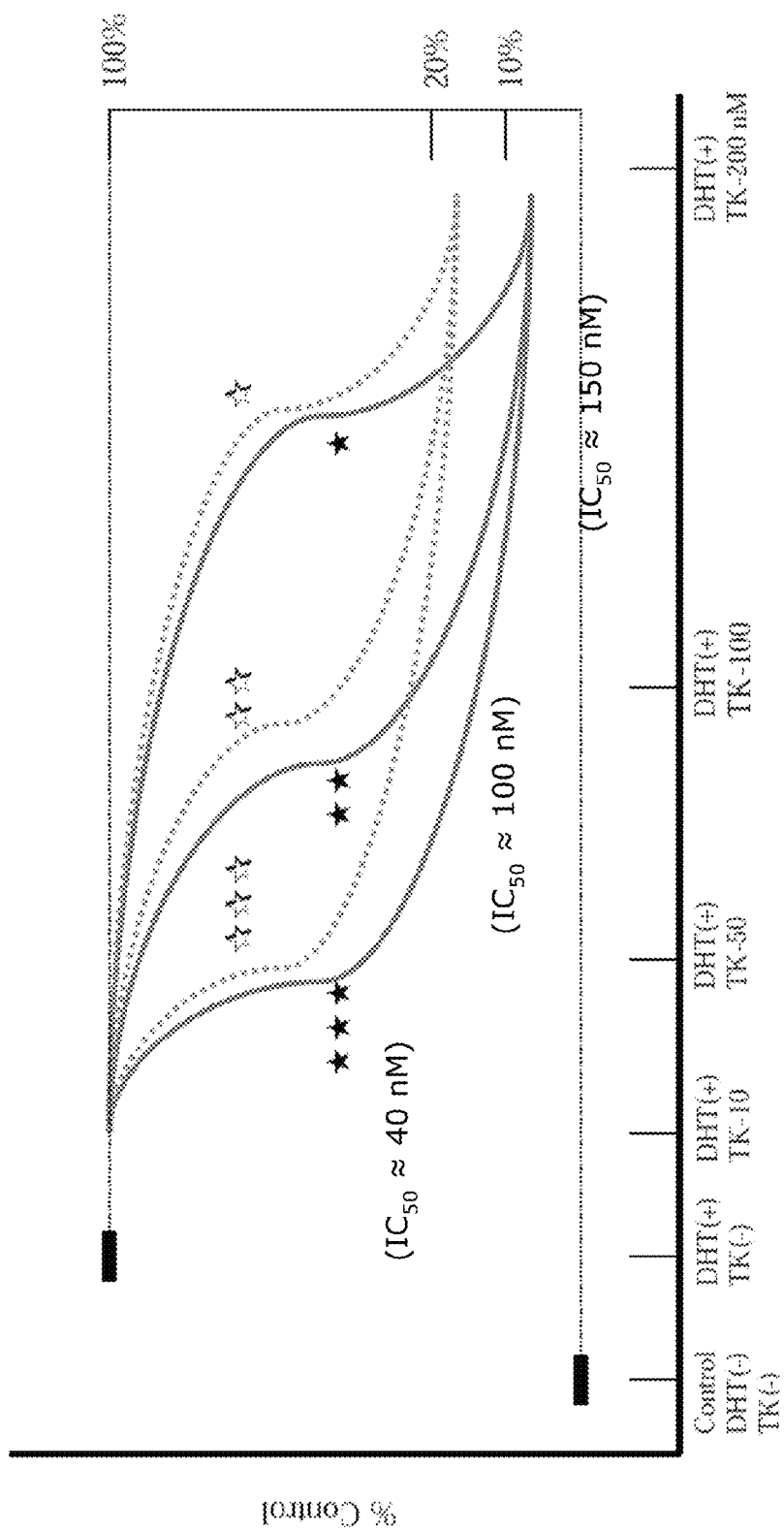
FIG. 17. evaluation of the utility of peptidomimetics on DHT induced proliferation of prostate cancer cells. The more effective the compound, the lower the concentration at which it affects the proliferation of prostate cancer cells. An ideal compound (***) is denoted with three black stars and has the highest efficacy at the lowest concentration and is shown for compounds below. For each of the derivatives in FIGS. 19A-N, this graph represents the effectiveness of each compound.
Figure 19A:
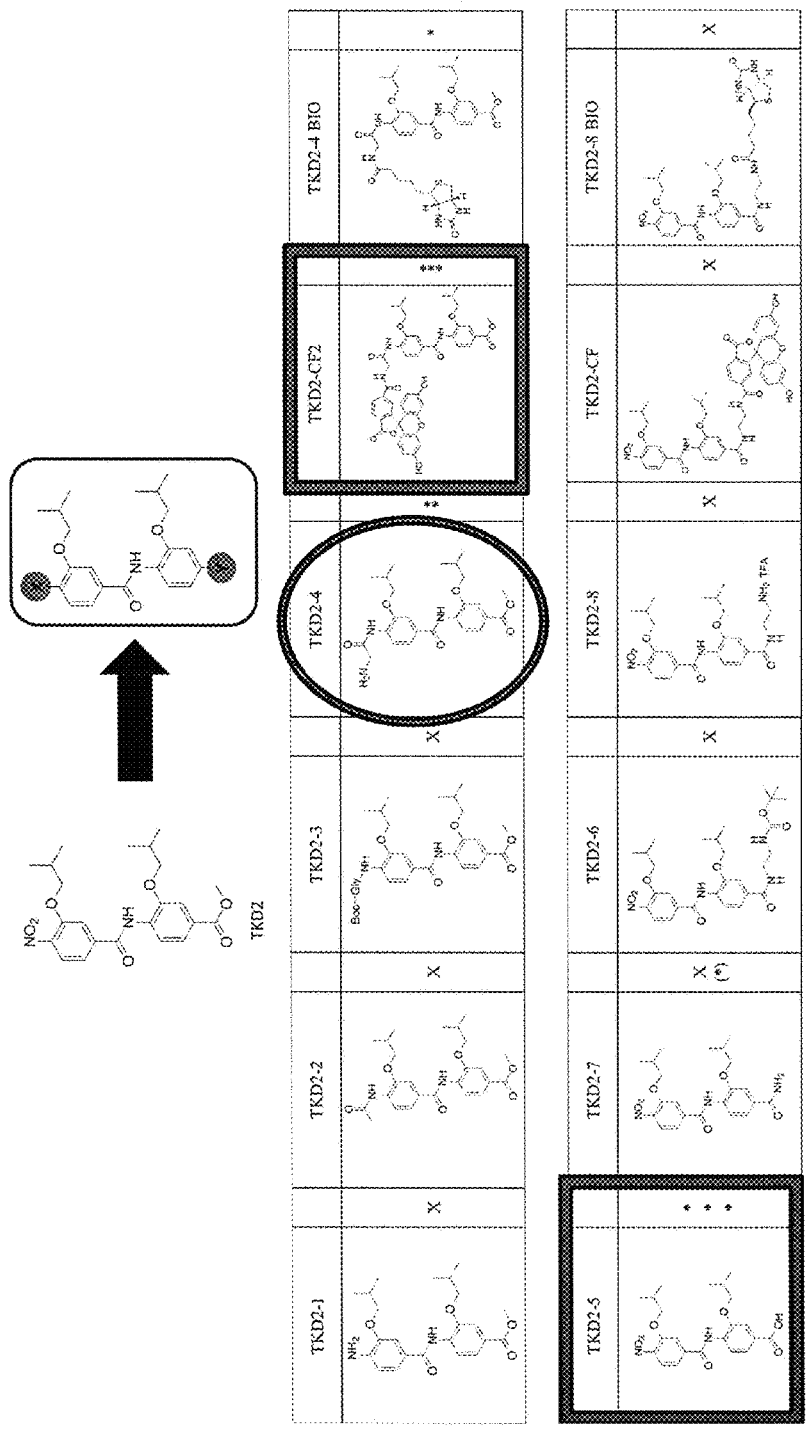
FIGS. 19A-N. Structure-function relationship of peptidomimetic analogues.
Figure 19B:
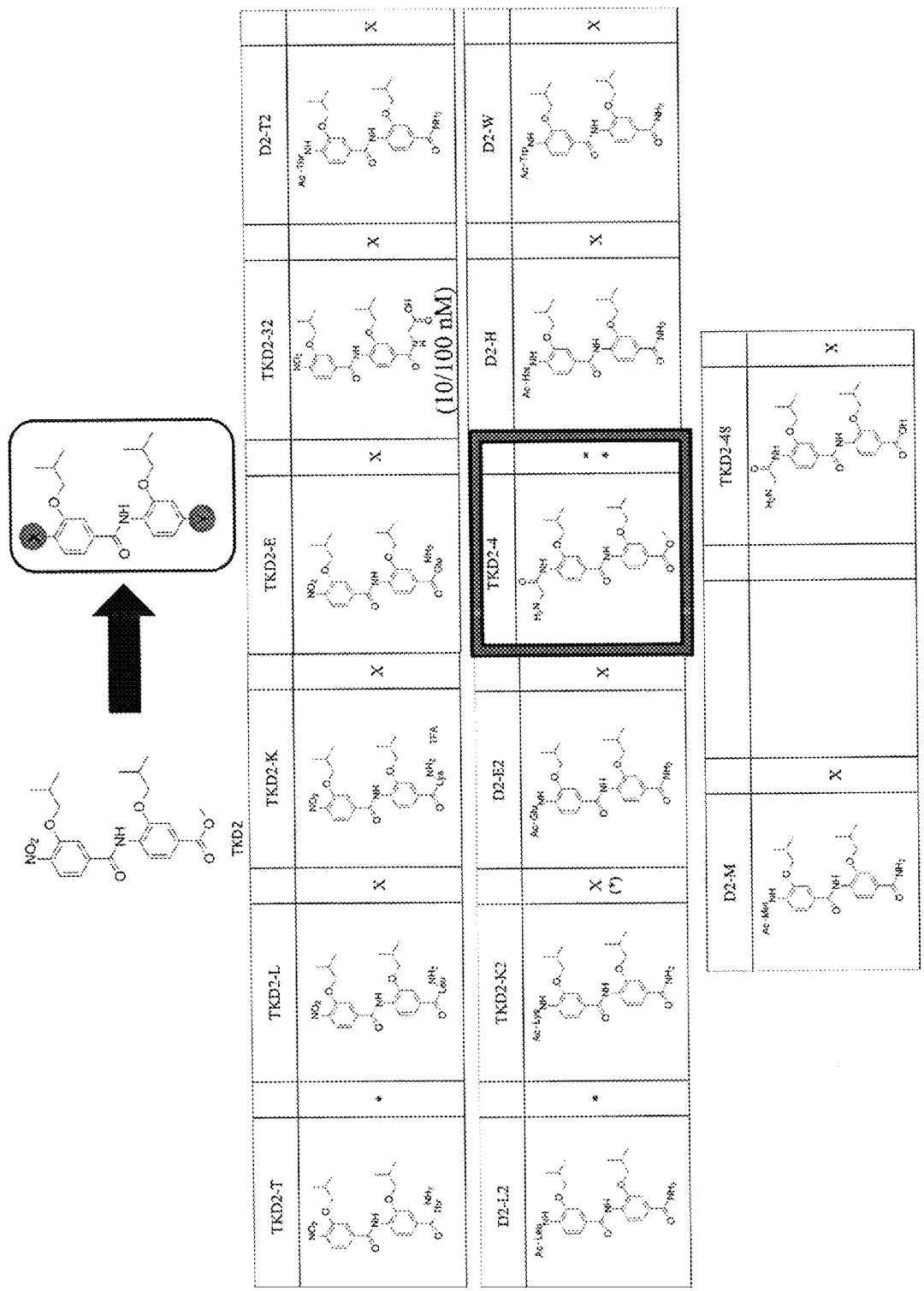
Figure 19C:
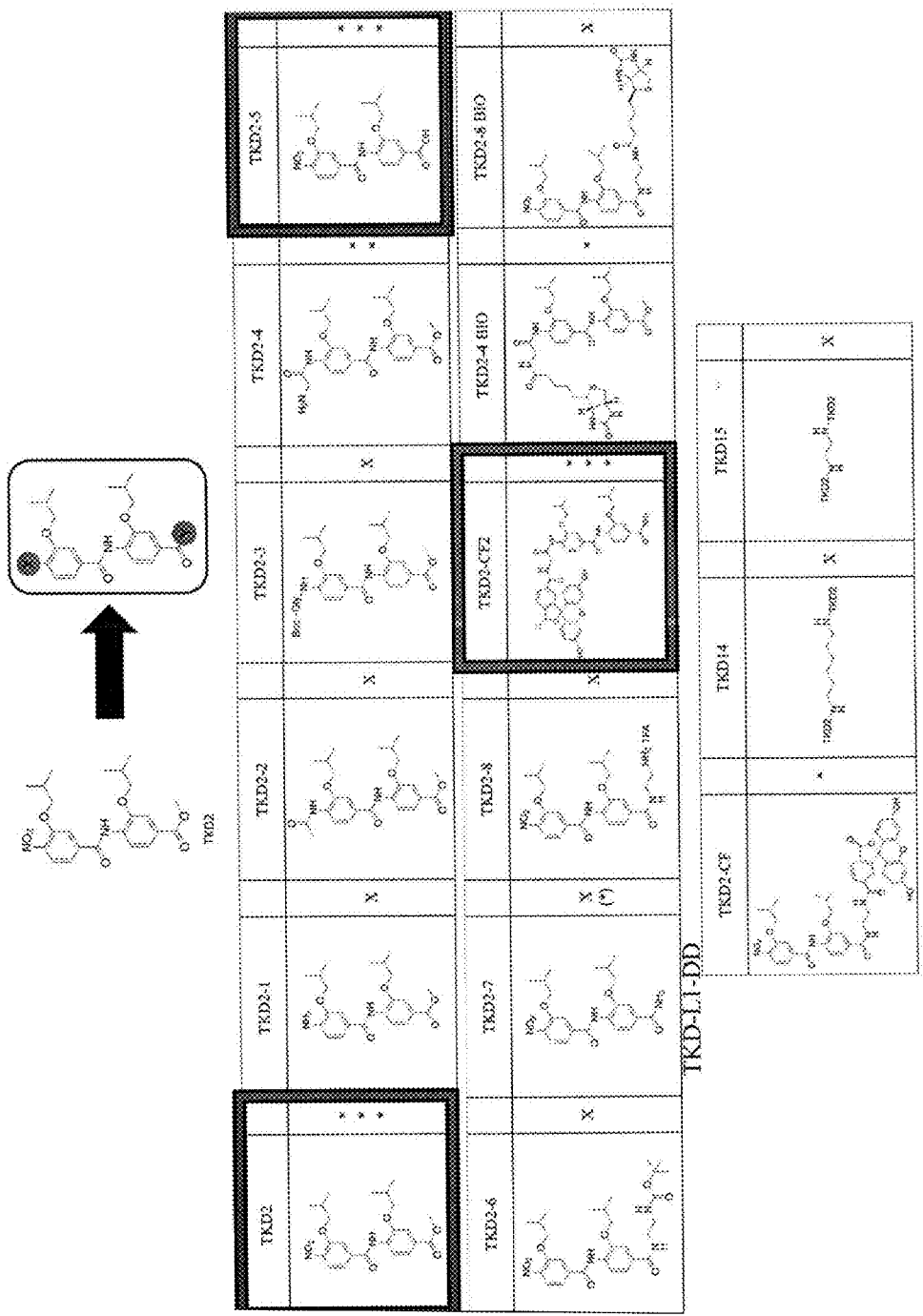
Figure 19D:
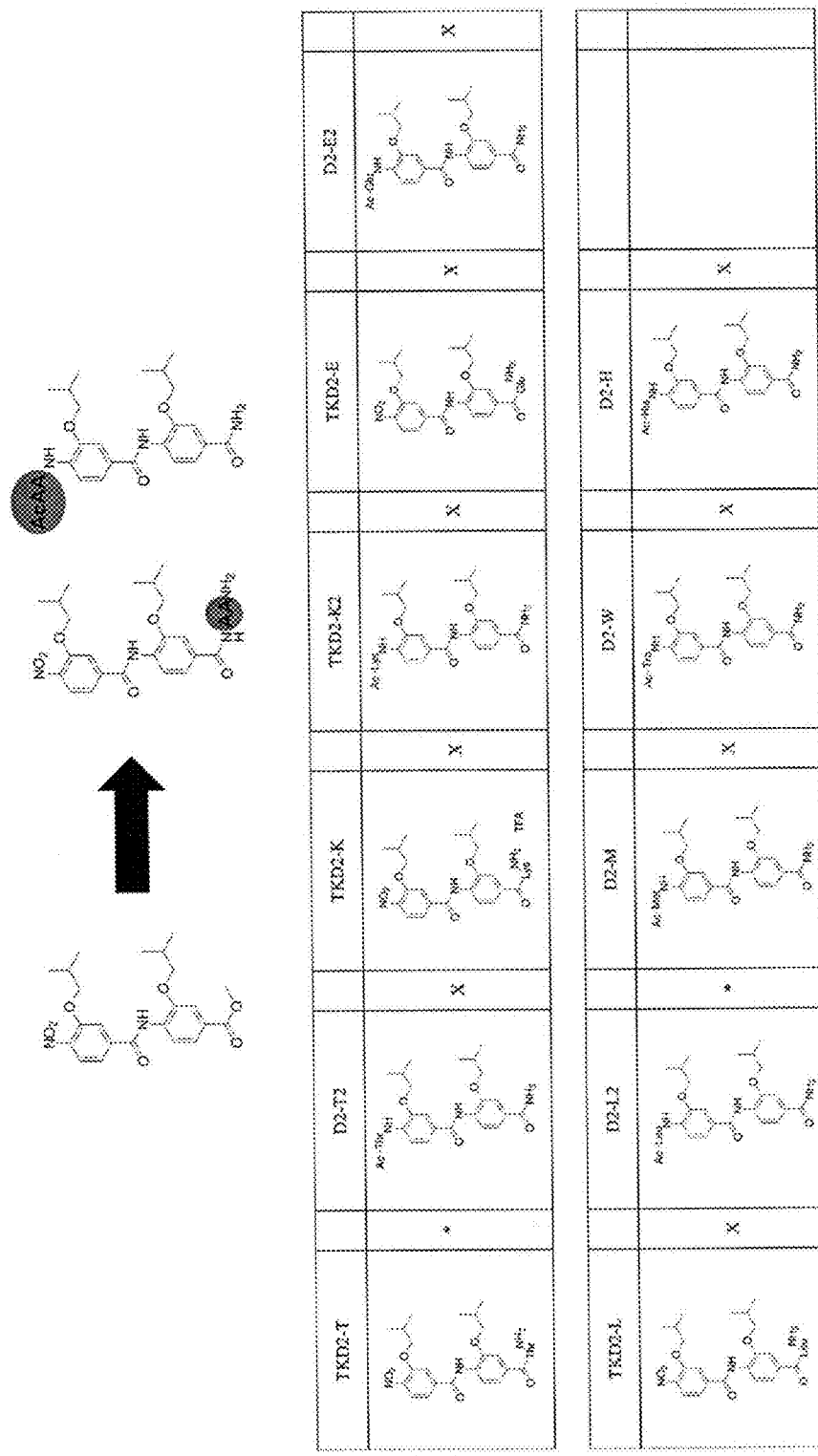
Figure 19D:
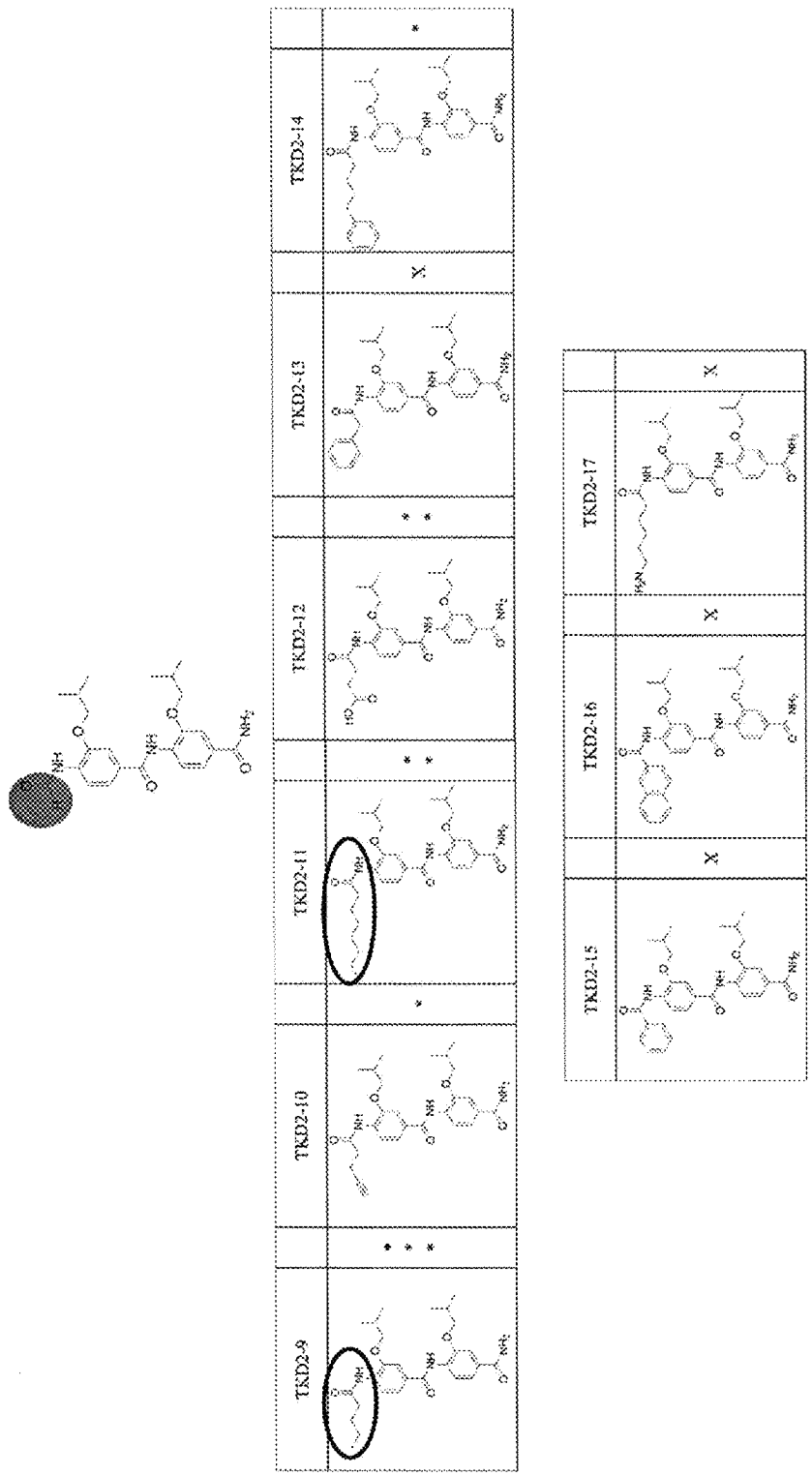
Figure 19D:
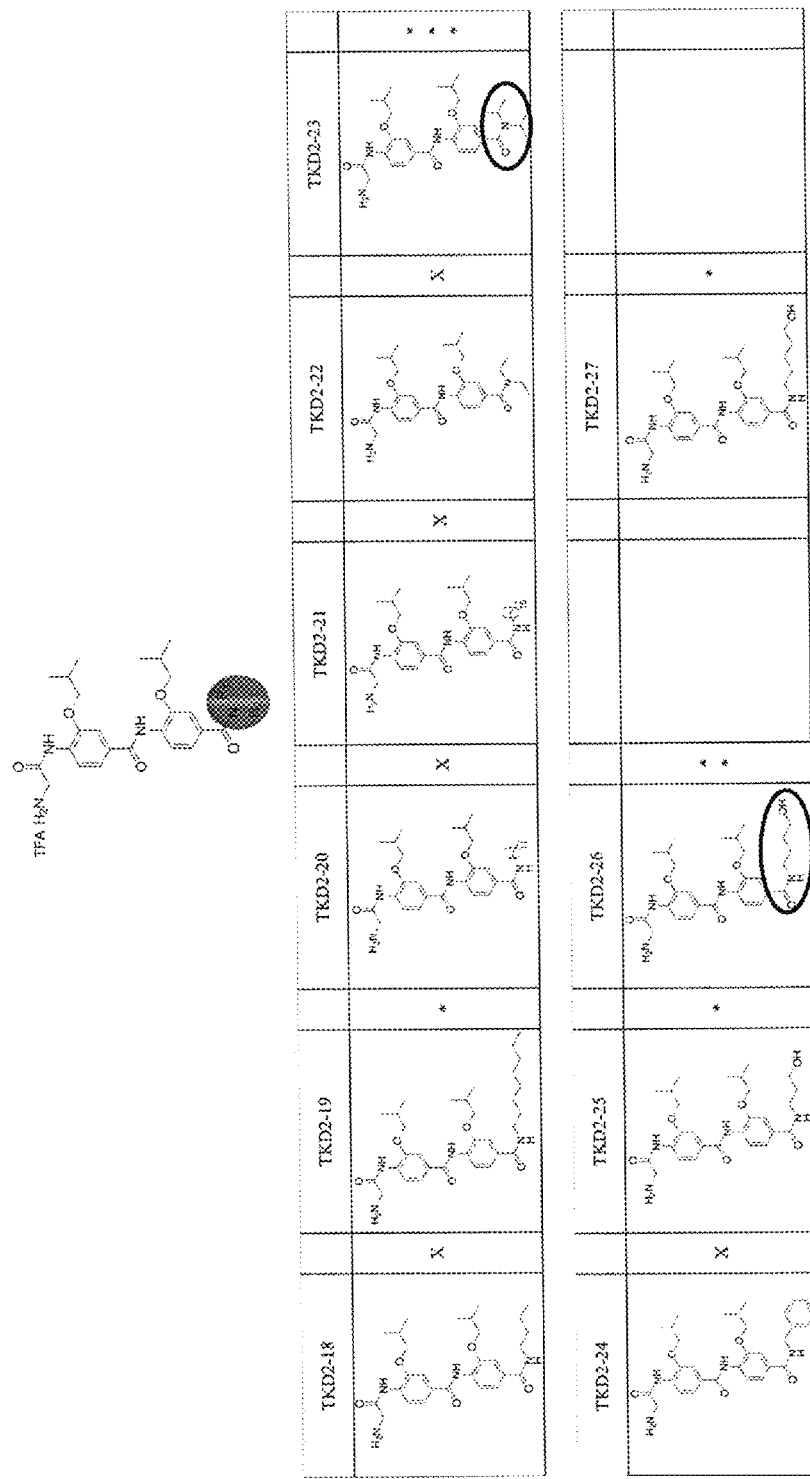
Figure 19E:
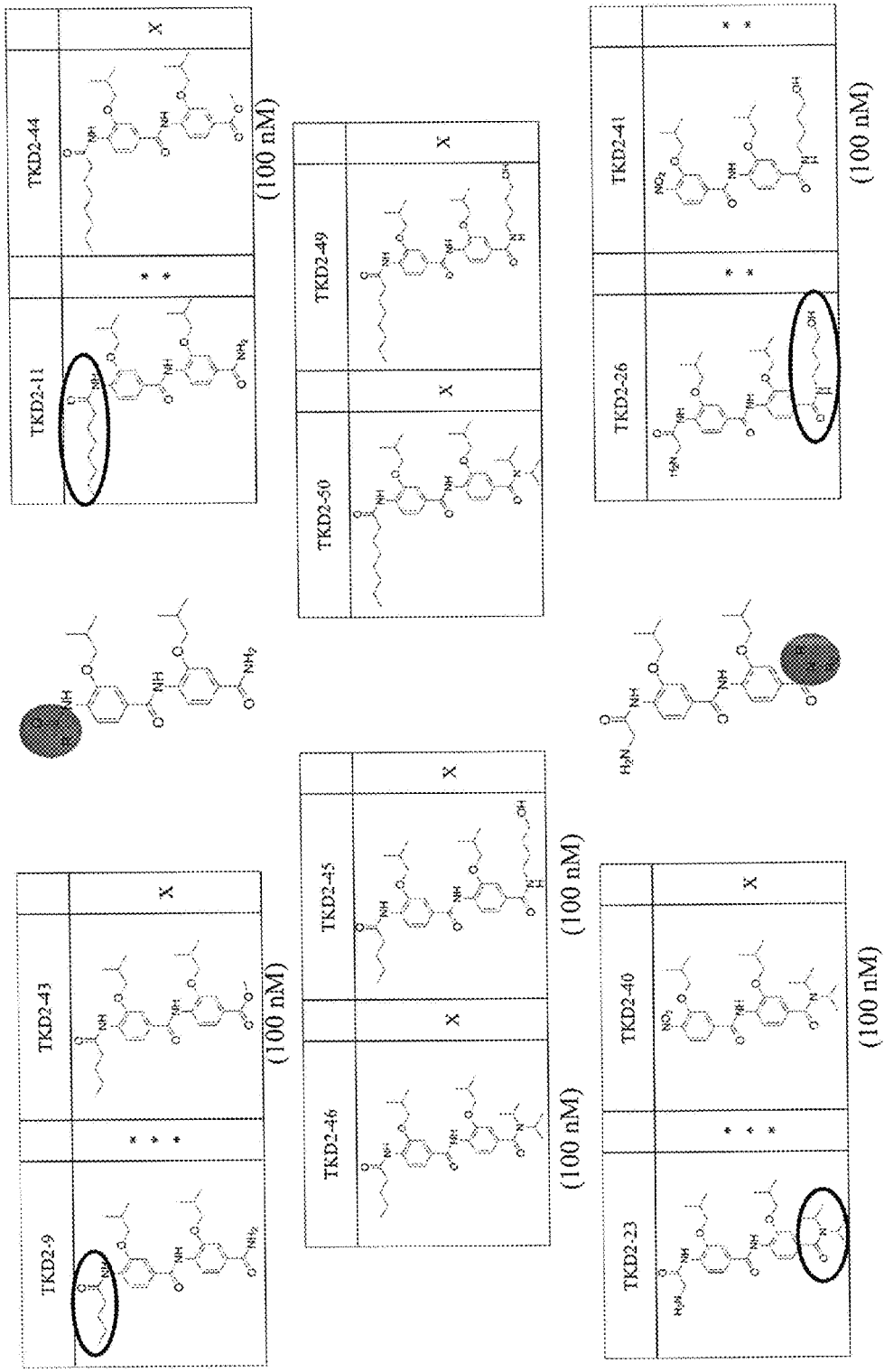
Figure 19F:
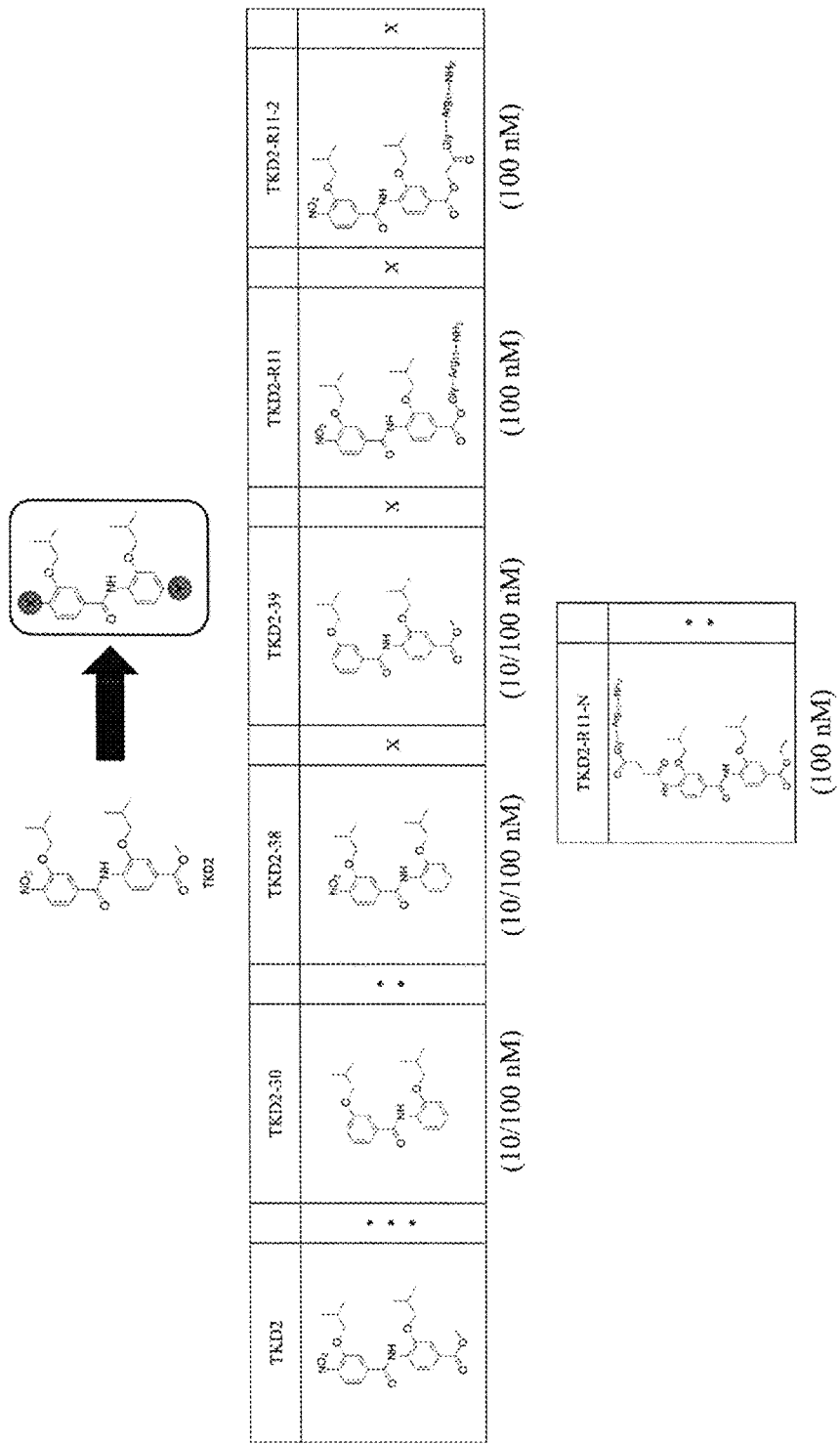
Figure 19G:
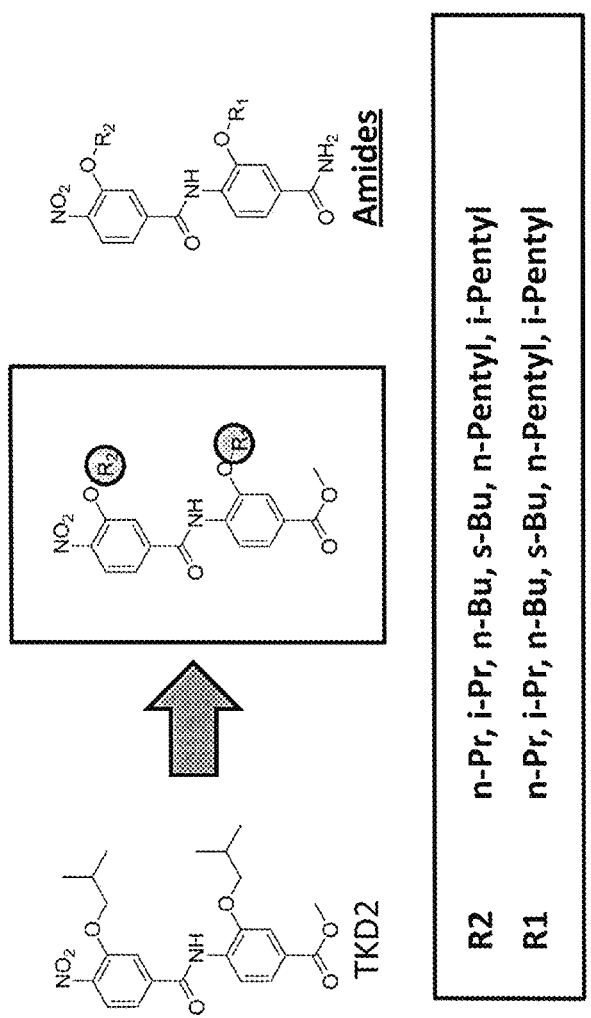
Figure 19H:
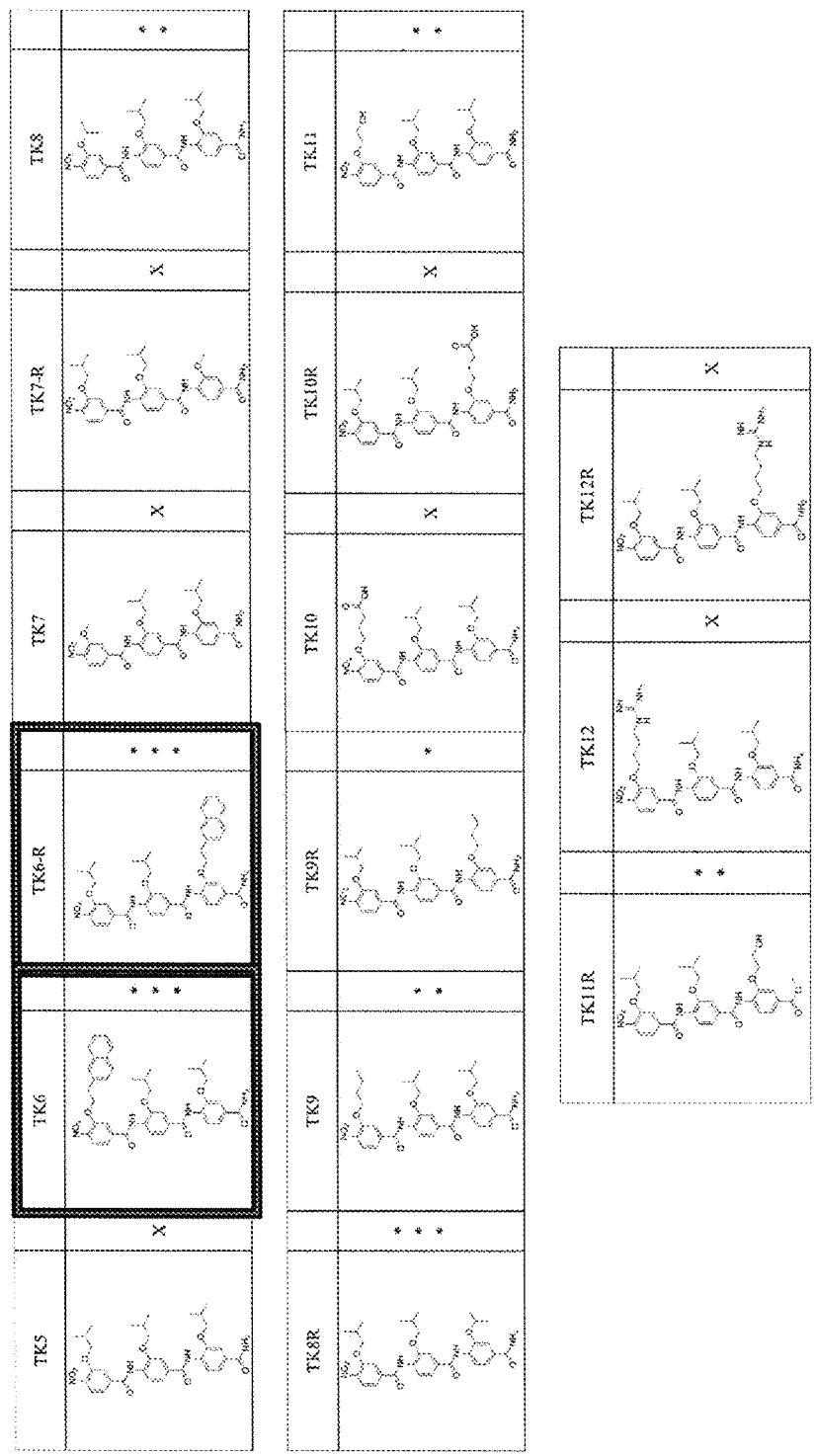
Figure 19I:
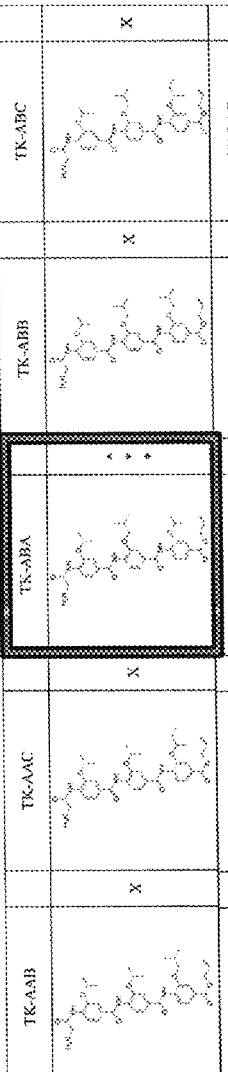
Figure 19J:
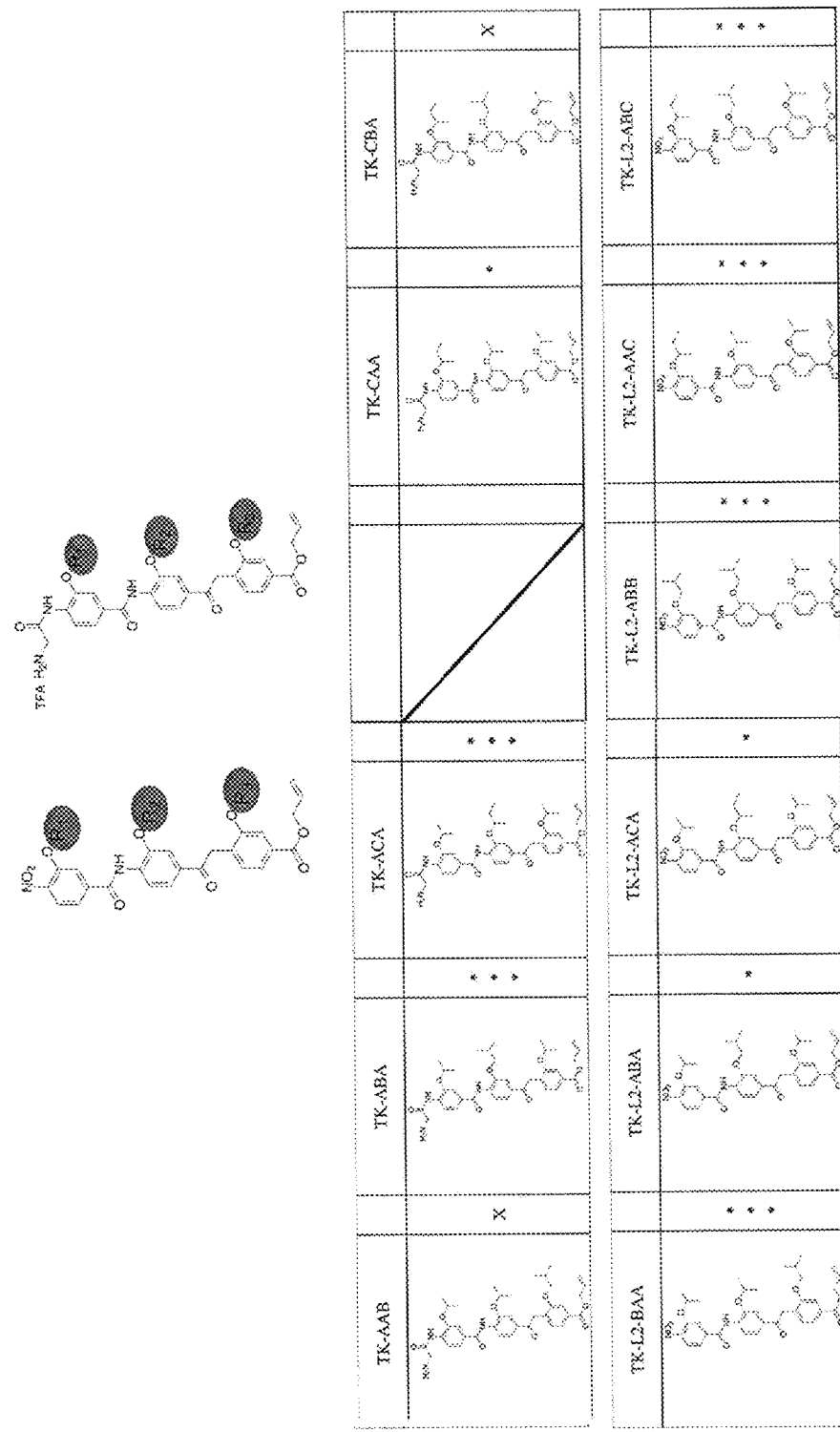
Figure 19K:
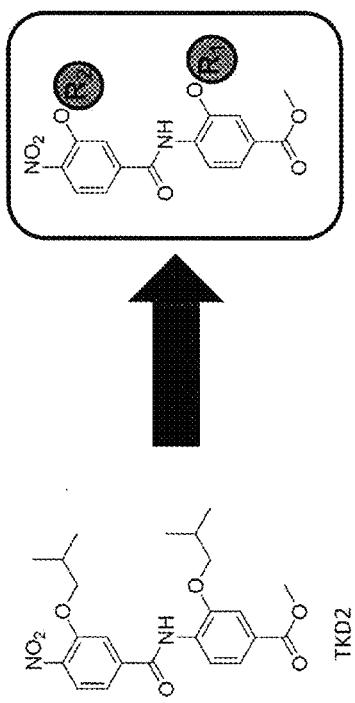
Figure 19L:
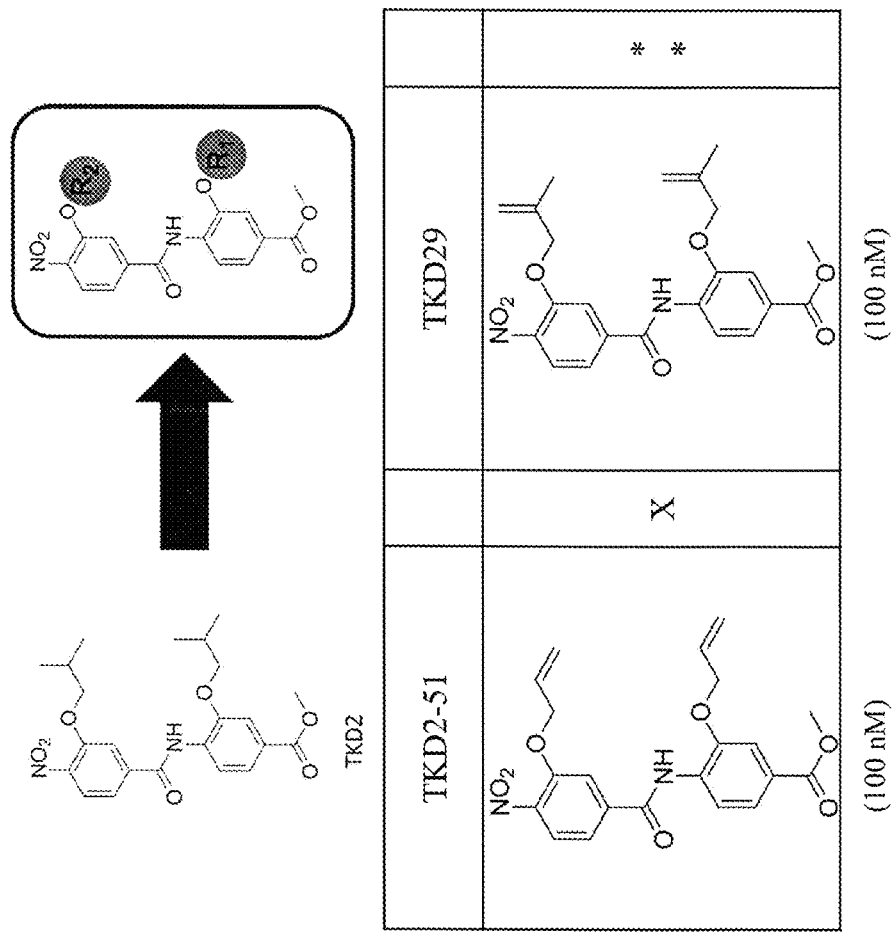
Figure 19M:
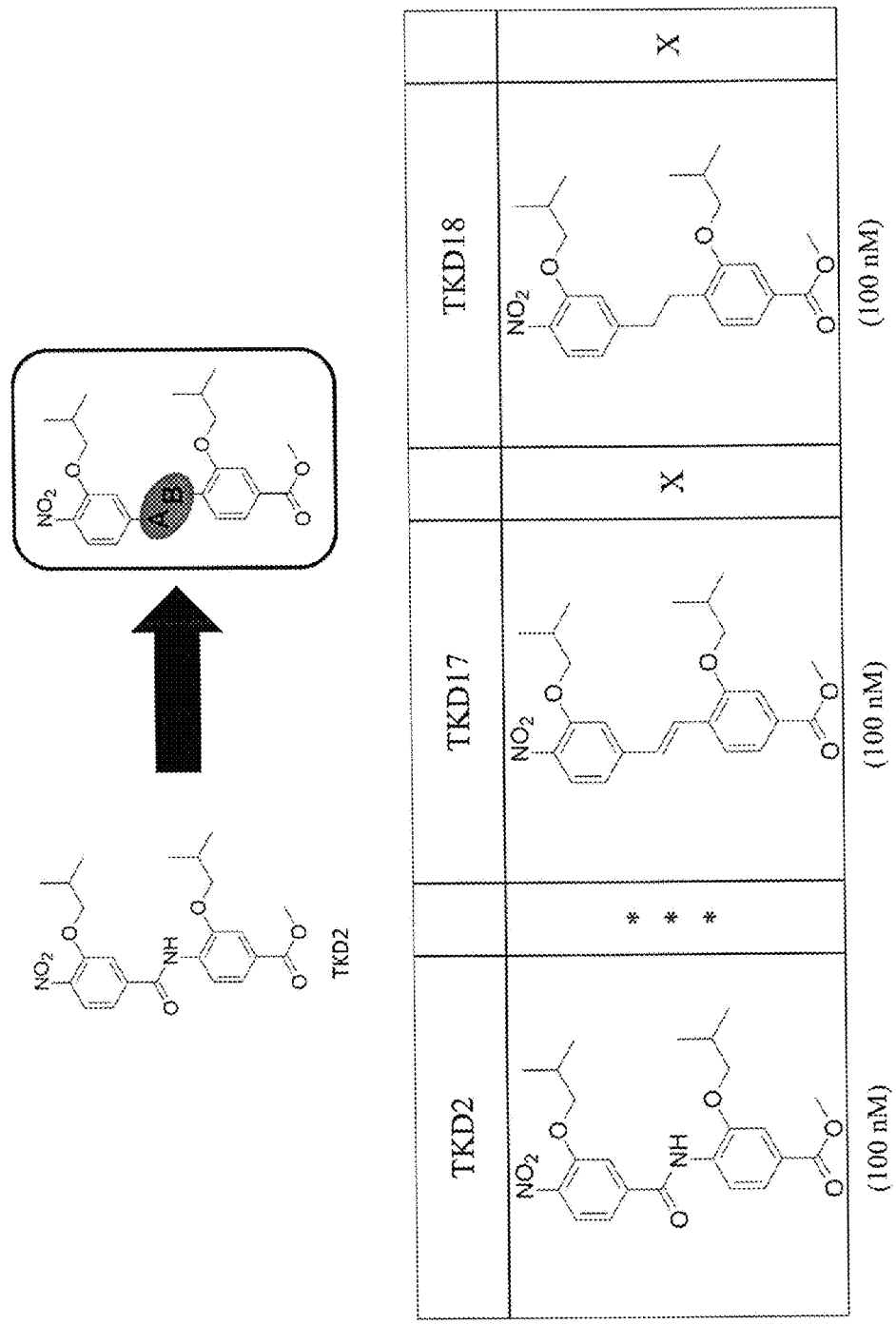
Figure 19N:
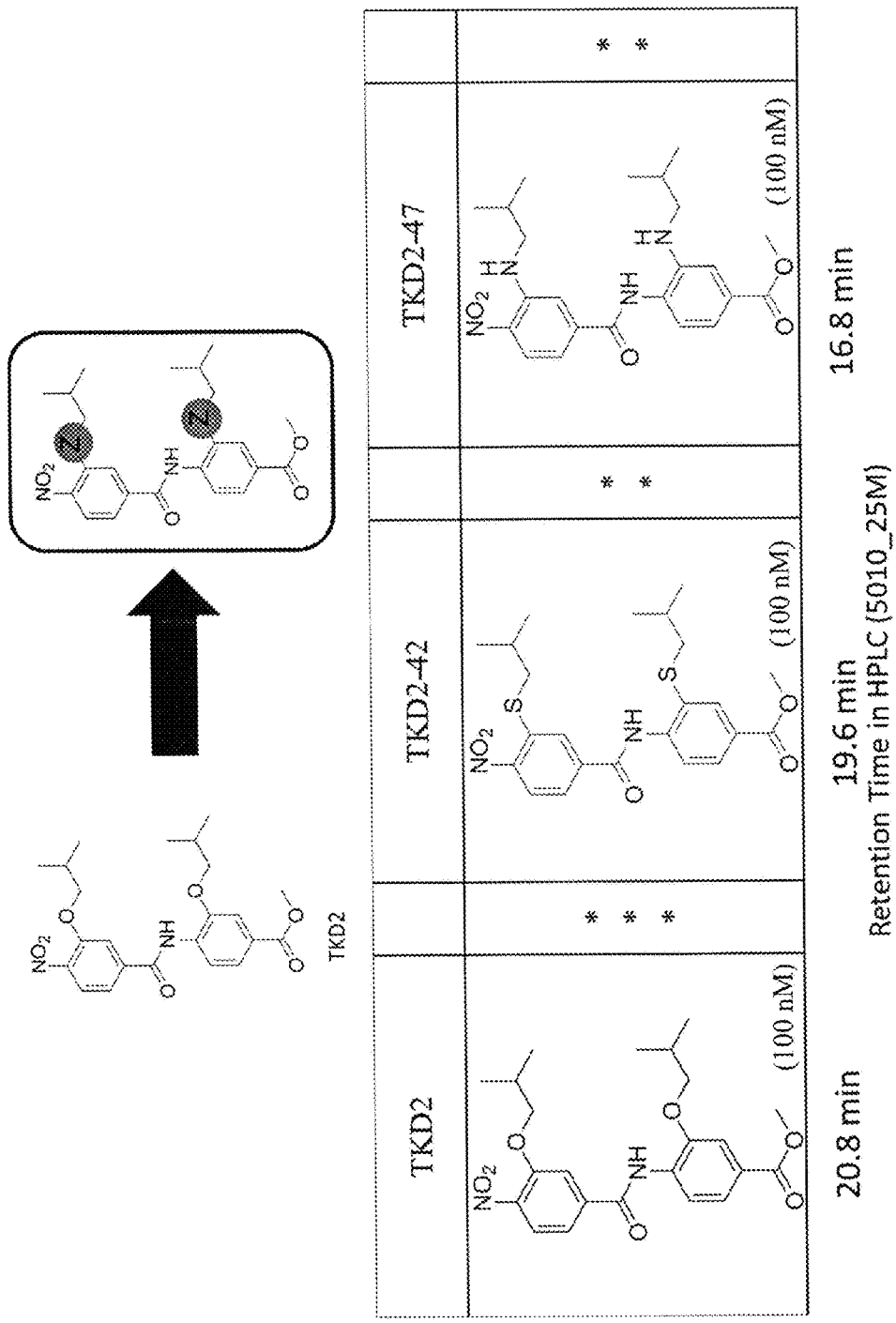

FIG. 17 shows proliferation assays for each of the derivatives in FIGS. 19A-N. This graph represents the effectiveness of each compound. Cells were plated (2-10×10³/well) in 96-well plates and subjected to androgen deprivation for 48 hours with phenol-red free RPMI and 1% charcoal stripped fetal bovine serum (CSF). Cells were then treated with either ethanol or DHT as a positive control for 48 hours Peptidomimetics were added 2 hours prior to treatment. Cell proliferation was measured using the MTT colorimetric assay. All experiments were performed in triplicate and the average of experiments displayed.

Figure 18:
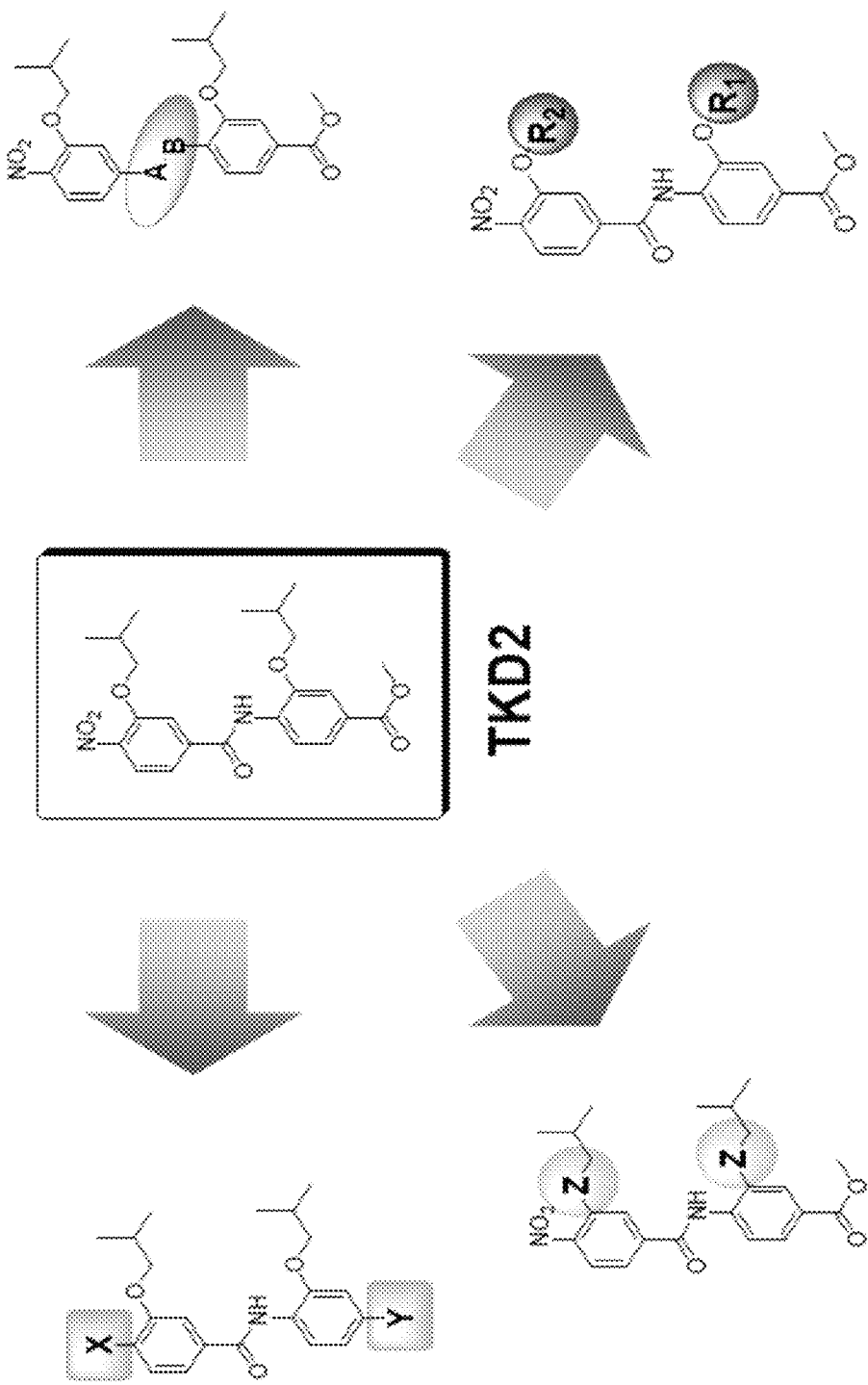
FIG. 18. Modifications of the D2 peptidomimetics.

FIG. 18 shows potential modifications of the D2 peptidomimetics. FIGS. 19A-N show a variety of tested compounds. FIG. 19A shows modifications of the x and y positions reveal that substituents such as D2-4 and D2-5 have maximal activity on the proliferation of prostate cancer cells in vivo. FIG. 19B shows modifications of the x and y positions reveal that substituents such as D2-4 has good activity on the proliferation of prostate cancer cells in vivo. FIG. 19C shows modifications of the x and y positions reveal that substituents such as D2-CF2 and D2-5 has excellent activity on the proliferation of prostate cancer cells in vivo. FIG. 19D shows that substituents such as D2-11, D2-12 and D2-26 have good activity on the proliferation of prostate cancer cells in vivo. FIG. 19E shows modifications that reveal that substituents such as D2-11, D2-23 and D2-26 have good activity on the proliferation of prostate cancer cells in vivo. FIG. 19F shows modifications revealing that substituents such as D2, D2-30 and D2R11N have good activity on the proliferation of prostate cancer cells in vivo (D2R11N is water soluble). FIG. 19G shows modifications revealing that substituents such as D2, D5-1, JHL05 and JHL04 have good activity on the proliferation of prostate cancer cells in vivo. FIG. 19H provides modifications revealing that substituents such as TK6, TK6-R, TK-8, TK8R. TK9, TK9R, TK11 and TK11R have good activity on the proliferation of prostate cancer cells in vivo. FIG. 19I illustrates modifications reveal that substituents such as TK-ABA, TK-L2-AAC, TK-L2-AAB, TK-L2-ABB, TK-L2-ABC, TK-L2-BAA, TK-L2-BAB, TK-L2-CBB and TK-L2-CCB have good activity on the proliferation of prostate cancer cells in vivo. FIG. 19J shows that substituents such as TK-ABA, TK-L2-ACA, TK-L2-ABB, TK-L2-ABC, TK-L2-BAA, TK-L2-AAC, and TK-L2-ABC have good activity on the proliferation of prostate cancer cells in vivo. FIG. 19K shows that substituents such as R1=nButyl, and R2=nButyl, and R1=iso Butyl and R2=secButyl and R1=nPropyl and R2=isobutyl have better activity than D2 on the proliferation of prostate cancer cells in vivo. These three work at lower concentrations than D2. FIG. 19L shown modifications revealing that substituents such as D29 has good activity on the proliferation of prostate cancer cells in vivo. FIG. 19M illustrates modifications such as D2 have good activity on the proliferation of prostate cancer cells in vivo. FIG. 19N shows that substituents such as D2 and D2-47 have good activity on the proliferation of prostate cancer cells in vivo. FIGS.

Figure 20:
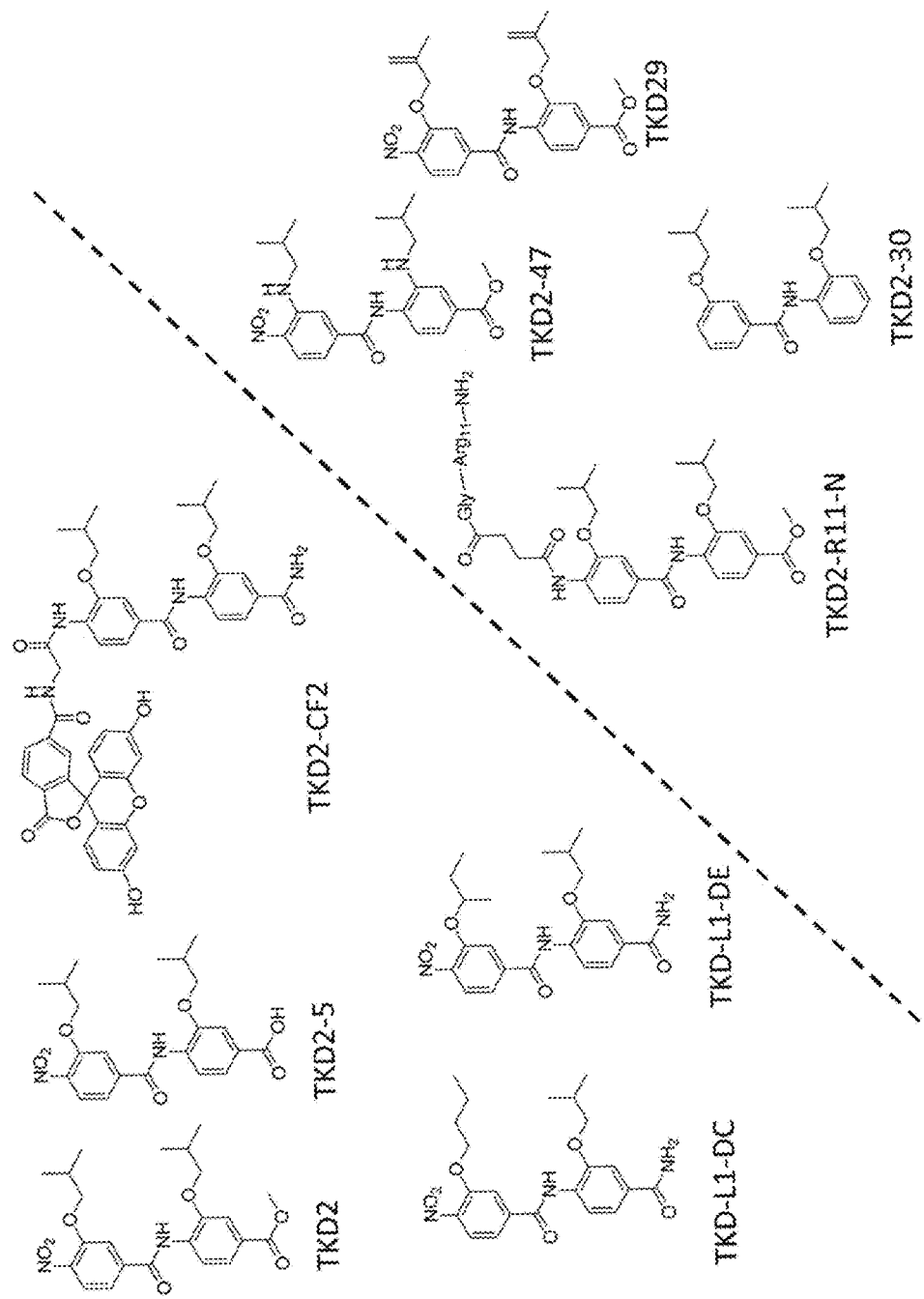
FIG. 20. Highest activity compounds.
Figure 21:
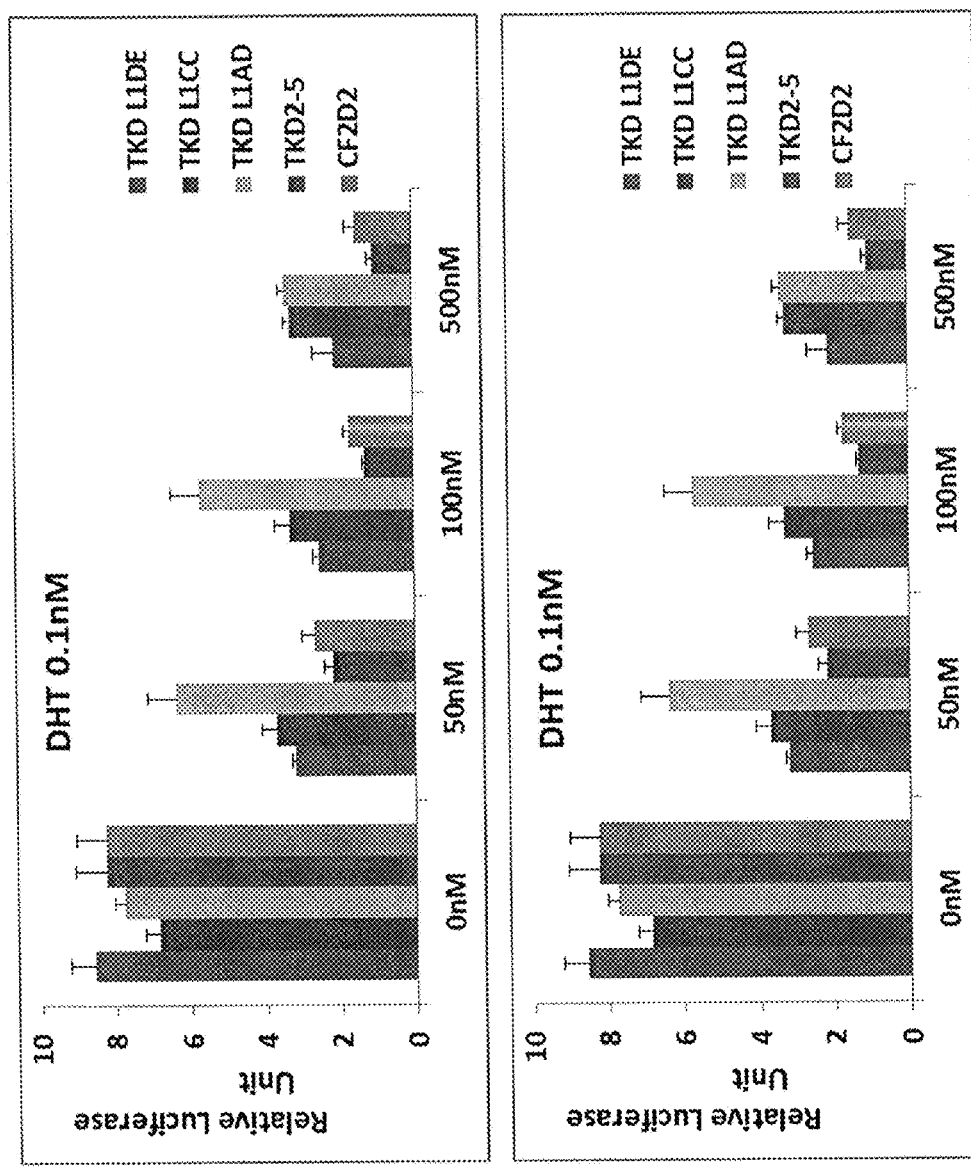
FIG. 21. Evaluation of the utility of peptidomimetics on DHT induced transcription from an ARE-luciferase in prostate cancer cells.
Figure 22:
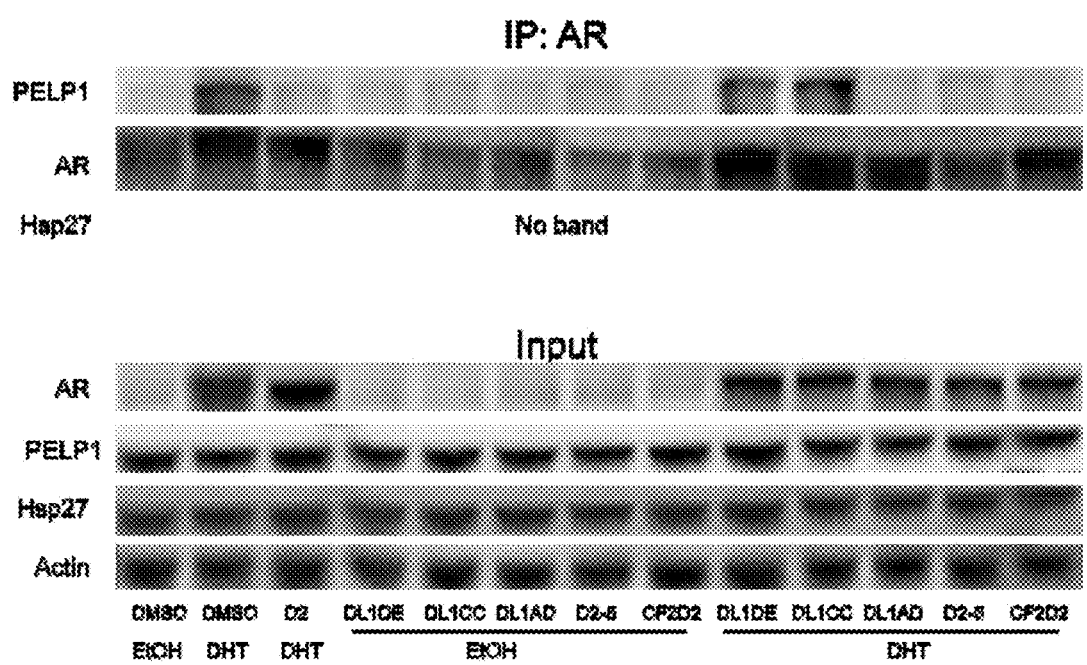
FIG. 22. Evaluation of the utility of peptidomimetics on DHT induced AR-PELP1 complex formation in a co-immunoprecipiration assay in prostate cancer cells.

FIG. 20 shows some of the highest activity compounds, and FIGS. 21-22 show various activities for the same.

Taken together, these results clearly indicate that the functional interaction of AR and PELP1 appears to be critical for AR signaling and that by blocking this interaction using rationally designed LXXLL peptidomimetics, AR nuclear translocation, AR-mediated genomic signaling and PCa cell proliferation can be affected. Peptidomimetics impacting this interaction are therefore useful in controlling AR signaling.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Publn. 2009/0012141
Ahn et al., *Mini-Rev. Med. Chem.*, 2:463-473, 2002.
Marshall, *Tetrahedron*, 49:3547-3558, 1993.

What is claimed:
1. A compound of formulas (A) or (B):

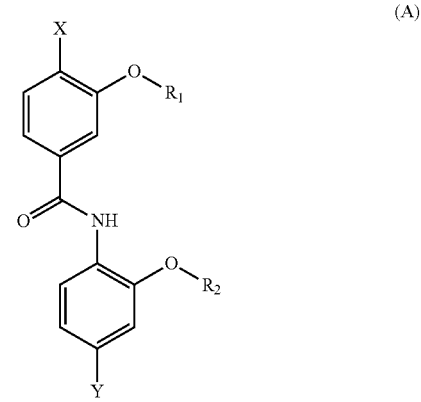

(A)

wherein:
R₁ and R₂ are each independently $C_1$-$C_{10}$ alkyl, $C_1$-$C_{10}$ alkenyl, $C_1$-$C_{10}$ alkynyl, $C_1$-$C_{15}$ optionally substituted arylalkyl, —(CH₂)ₙ—COOR, —(CH₂)ₙ—CONRR', —(CH₂)ₙ—NRR', —(CH₂)ₙ—NH(C=NH)NRR', —(CH₂)ₙ—NRCOR', —(CH₂)ₙ—NRCOOR', —(CH₂)ₙ—OR, —(CH₂)ₙ—SR, —(CH₂)ₙ—SO_mR, —(CH₂)ₙ—PO_mR, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl group;

X is —NO₂ or —NHC(O)CH₂R₃, wherein R₃ is —NO₂, —NH₂, —Z, $C_1$-$C_{10}$ alkyl, $C_1$-$C_{10}$ alkenyl, $C_1$-$C_{10}$ alkynyl, or $C_1$-$C_{15}$ arylalkyl, each of which is optionally substituted with —COOR, —CONRR', —NRR', —NH(C=NH)NRR', —NRCOR', —NRCOOR', —OR, —SR, —SO_nR, or —PO_nR, wherein n may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl group, and wherein Z is:

67

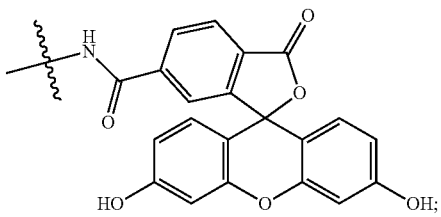

and

Y is —(CH$_2$)$_n$CONR$_4$R$_5$, —(CH$_2$)$_n$NR$_4$R$_5$, —(CH$_2$)$_n$—NR$_4$R$_5$, —(CH$_2$)$_n$—NH(C=NH)NR$_4$R$_5$, —(CH$_2$)$_n$—NR$_4$COR$_5$, —(CH$_2$)$_n$—NR$_4$COOR$_5$, —(CH$_2$)$_n$—OR$_4$, —(CH$_2$)$_n$—SR$_4$, —(CH$_2$)$_n$—SO$_m$R$_4$, —(CH$_2$)$_n$—PO$_m$R$_4$, wherein n and m may be any number between 0 and 6, R$_4$ and R$_5$ are independently selected from —H, C$_1$-C$_{10}$ alkyl, C$_1$-C$_{10}$ alkenyl, C$_1$-C$_{10}$ alkynyl, or C$_1$-C$_{15}$ optionally substituted arylalkyl group; or (B)

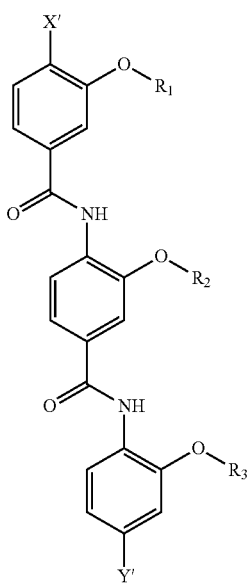

wherein:

R$_1$, R$_2$ and R$_3$ are each independently C$_1$-C$_{10}$ alkyl, C$_1$-C$_{10}$ alkenyl, C$_1$-C$_{10}$ alkynyl, C$_1$-C$_{15}$ optionally substituted arylalkyl, —(CH$_2$)$_n$—COOR, —(CH$_2$)$_n$—CONRR', —(CH$_2$)$_n$—NRR', —(CH$_2$)$_n$—NH(C=NH)NRR', —(CH$_2$)$_n$—NRCOR', —(CH$_2$)$_n$—NRCOOR', —(CH$_2$)$_n$—OR, —(CH$_2$)$_n$—SR, —(CH$_2$)$_n$—SO$_m$R, —(CH$_2$)$_n$—PO$_m$R, wherein n and m may be any number between 0 and 6 and R and R' may be a H, C$_1$-C$_{10}$ alkyl, C$_1$-C$_{10}$ alkenyl, C$_1$-C$_{10}$ alkynyl, or C$_1$-C$_{15}$ optionally substituted arylalkyl group or

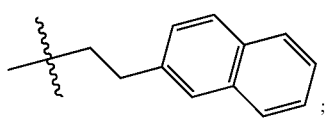

X' is —NO$_2$ or —NHC(O)CH$_2$R$_3$, wherein R$_3$ is —NO$_2$, —NH$_2$, —Z', C$_1$-C$_{10}$alkyl, C$_1$-C$_{10}$ alkenyl,

68

C$_1$-C$_{10}$ alkynyl, or C$_1$-C$_{15}$ arylalkyl, each of which is optionally substituted with —COOR, —CONRR', —NRR', —NH(C=NH)NRR', —NRCOR', —NRCOOR', —OR, —SR, —SO$_n$R, or —PO$_n$R, wherein n may be any number between 0 and 6 and R and R' may be a H, C$_1$-C$_{10}$ alkyl, C$_1$-C$_{10}$ alkenyl, C$_1$-C$_{10}$ alkynyl, or C$_1$-C$_{15}$ optionally substituted arylalkyl group, and wherein Z' is:

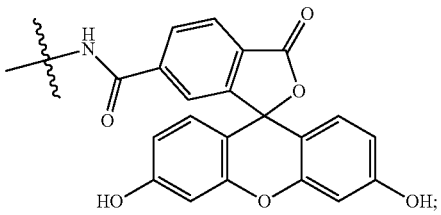

and

Y' is —(CH$_2$)$_n$CONR$_4$R$_5$, —(CH$_2$)$_n$NR$_4$R$_5$, —(CH$_2$)$_n$—NR$_4$R$_5$, —(CH$_2$)$_n$—NH(C=NH)NR$_4$R$_5$, —(CH$_2$)$_n$—NR$_4$COR$_5$, —(CH$_2$)$_n$—NR$_4$COOR$_5$, —(CH$_2$)$_n$—OR$_4$, —(CH$_2$)$_n$—SR$_4$, —(CH$_2$)$_n$—SO$_m$R$_4$, —(CH$_2$)$_n$—PO$_m$R$_4$, wherein n and m may be any number between 0 and 6, R$_4$ and R$_5$ are independently selected from —H, C$_1$-C$_{10}$ alkyl, C$_1$-C$_{10}$ alkenyl, C$_1$-C$_{10}$ alkynyl, or C$_1$-C$_{15}$ optionally substituted arylalkyl group.

2. The compound of claim 1, further defined as a compound of formula (A).

3. The compound of claim 1, further defined as a compound of formula (B).

4. The compound of claim 2, wherein X is —NO$_2$.

5. The compound of claim 3, wherein X' is —NO$_2$.

6. The compound of claim 4, wherein:

R$_1$ and R$_2$ are C$_1$-C$_{10}$ alkyl, C$_1$-C$_{10}$ alkenyl, or C$_1$-C$_{10}$ alkynyl, R$_1$ and R$_2$ are optionally substituted C$_1$-C$_{15}$ arylalkyl, R$_1$ and R$_2$ are —(CH$_2$)$_n$—NRR' or —(CH2)$_n$—NH(C=NH)NRR' groups, wherein n may be any number between 0 and 6 and R and R' may be a H, C$_1$-C$_{10}$ alkyl, C$_1$-C$_{10}$ alkenyl, C$_1$-C$_{10}$ alkynyl, or C$_1$-C$_{15}$ optionally substituted arylalkyl, R$_1$ and R$_2$ are —(CH$_2$)$_n$—COOR, —(CH$_2$)$_n$—CONRR', —(CH$_2$)$_n$—NRCOR', —(CH$_2$)$_n$—NRCOOR', —(CH$_2$)$_n$—SO$_m$R, —(CH$_2$)$_n$—PO$_m$R, wherein n and m may be any number between 0 and 6 and R and R' may be a H, C$_1$-C$_{10}$ alkyl, C$_1$-C$_{10}$ alkenyl, C$_1$-C$_{10}$ alkynyl, or C$_1$-C$_{15}$ optionally substituted arylalkyl, R$_1$ and R$_2$ are —(CH$_2$)$_n$—OR, —(CH$_2$)$_n$—SR, wherein R may be a H, C$_1$-C$_{10}$ alkyl, C$_1$-C$_{10}$ alkenyl, C$_1$-C$_{10}$ alkynyl, or C$_1$-C$_{15}$ optionally substituted arylalkyl, R$_1$ is C$_1$-C$_{15}$ optionally substituted arylalkyl, and R$_2$ is C$_1$-C$_{10}$ alkyl, C$_1$-C$_{10}$ alkenyl, or C$_1$-C$_{10}$ alkynyl, R$_1$ is C$_1$-C$_{10}$ alkyl, C$_1$-C$_{10}$ alkenyl, or C$_1$-C$_{10}$ alkynyl, and R$_2$ is C-C$_{15}$ optionally substituted arylalkyl, R$_1$ is —(CH$_2$)$_n$—NRR' or —(CH$_2$)$_n$—NH(C=NH)NRR', and R$_2$ is —(CH$_2$)$_n$—COOR, —(CH$_2$)$_n$—SO$_m$R, —(CH$_2$)$_n$—PO$_m$R, wherein n and m may be any number between 0 and 6 and R and R' may be a H, C$_1$-C$_{10}$ alkyl, C$_1$-C$_{10}$ alkenyl, C$_1$-C$_{10}$ alkynyl, or C$_1$-C$_{15}$ optionally substituted arylalkyl group, or R$_1$ is —(CH$_2$)$_n$—COOR, —(CH$_2$)$_n$—SO$_m$R, —(CH$_2$)$_n$—PO$_m$R, and R$_2$ is —(CH$_2$)$_n$—NRR' or —(CH$_2$)$_n$—NH(C=NH)NRR', wherein n and m may be any number between 0 and 6 and R and R' may be a H, C$_1$-C$_{10}$ alkyl, $C_1$-$C_{10}$ alkenyl, $C_1$-$C_{10}$ alkynyl, or $C_1$-$C_{15}$ optionally substituted arylalkyl group.

7. The compound of claim 5, wherein:

$R_1$, $R_2$, and $R_3$ are $C_1$-$C_{10}$ alkyl, $C_1$-$C_{10}$ alkenyl, or $C_1$-$C_{10}$ alkynyl, $R_1$, $R_2$, and $R_3$ are optionally substituted $C_1$-$C_{15}$ arylalkyl, $R_1$, $R_2$, and $R_3$ are —$(CH_2)_n$—NRR' or —$(CH_2)_n$—NH(C=NH)NRR' groups, wherein n may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl, $R_1$, $R_2$, and $R_3$ are —$(CH_2)_n$—COOR, —$(CH_2)_n$—CONRR', —$(CH_2)_n$—NRCOR', —$(CH_2)_n$—NRCOOR', —$(CH_2)_n$—SO$_m$R, —$(CH_2)_n$—PO$_m$R, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl, $R_1$, $R_2$, and $R_3$ are —$(CH_2)_n$—OR, —$(CH_2)_n$—SR, wherein R may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl, $R_1$ is $C_1$-$C_{15}$ optionally substituted arylalkyl, and $R_2$ and $R_3$ are $C_1$-$C_{10}$ alkyl, $C_1$-$C_{10}$ alkenyl, or $C_1$-$C_{10}$ alkynyl, $R_1$ and $R_2$ are $C_1$-$C_{10}$ alkyl, $C_1$-$C_{10}$ alkenyl, or $C_1$-$C_{10}$ alkynyl, and $R_3$ is $C_1$-$C_{15}$ optionally substituted arylalkyl, $R_1$ is $C_1$-$C_{10}$ alkyl, $C_1$-$C_{10}$ alkenyl, or $C_1$-$C_{10}$ alkynyl, and $R_2$ and $R_3$ are $C_1$-$C_{15}$ optionally substituted arylalkyl, $R_1$ and $R_2$ are $C_1$-$C_{15}$ optionally substituted arylalkyl, and $R_3$ is $C_1$-$C_{10}$ alkyl, $C_1$-$C_{10}$ alkenyl, or $C_1$-$C_{10}$ alkynyl, $R_1$ and $R_3$ are $C_1$-$C_{10}$ alkyl, $C_1$-$C_{10}$ alkenyl, or $C_1$-$C_{10}$ alkynyl, and $R_2$ is $C_1$-$C_{15}$ optionally substituted arylalkyl, $R_1$ and $R_3$ are $C_1$-$C_{15}$ optionally substituted arylalkyl, and $R_2$ is $C_1$-$C_{10}$ alkyl, $C_1$-$C_{10}$ alkenyl, or $C_1$-$C_{10}$ alkynyl, $R_1$ and $R_2$ are —$(CH_2)_n$—NRR' or —$(CH_2)_n$—NH(C=NH)NRR', and $R_3$ is $C_1$-$C_{10}$ alkyl, $C_1$-$C_{10}$ alkenyl, or $C_1$-$C_{10}$ alkynyl, wherein n may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl, $R_1$ is $C_1$-$C_{10}$ alkyl, $C_1$-$C_{10}$ alkenyl, or $C_1$-$C_{10}$ alkynyl, and $R_2$ and $R_3$ are —$(CH_2)_n$—NRR' or —$(CH_2)_n$—NH(C=NH)NRR', wherein n may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl, $R_1$ and $R_2$ are —$(CH_2)_n$—NRR' or —$(CH_2)_n$—NH(C=NH)NRR', and $R_3$ is $C_1$-$C_{15}$ optionally substituted arylalkyl, wherein n may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl, $R_1$ is $C_1$-$C_{15}$ optionally substituted arylalkyl, and $R_2$ and $R_3$ are —$(CH_2)_n$—NRR' or —$(CH_2)_n$—NH(C=NH)NRR', wherein n may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl, $R_1$ and $R_2$ are —$(CH_2)_n$—COOR, —$(CH_2)_n$—CONRR', —$(CH_2)_n$—NRCOR', —$(CH_2)_n$—NRCOOR', —$(CH_2)_n$—SO$_m$R, —$(CH_2)_n$—PO$_m$R, and $R_3$ is $C_1$-$C_{10}$ alkyl, $C_1$-$C_{10}$ alkenyl, or $C_1$-$C_{10}$ alkynyl, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl, $R_1$ is $C_1$-$C_{10}$ alkyl, $C_1$-$C_{10}$ alkenyl, or $C_1$-$C_{10}$ alkynyl, and $R_2$ and $R_3$ are —$(CH_2)_n$—COOR, —$(CH_2)_n$—CONRR', —$(CH_2)_n$—NRCOR', —$(CH_2)_n$—NRCOOR', —$(CH_2)_n$—SO$_m$R, —$(CH_2)_n$—PO$_m$R, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl, $R_1$ and $R_2$ are —$(CH_2)_n$—COOR, —$(CH_2)_n$—CONRR', —$(CH_2)_n$—NRCOR', —$(CH_2)_n$—NRCOOR', —$(CH_2)_n$—SO$_m$R, —$(CH_2)_n$—PO$_m$R, and $R_3$ is $C_1$-$C_{15}$ optionally substituted arylalkyl, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl, $R_1$ is $C_1$-$C_{15}$ optionally substituted arylalkyl, and $R_2$ and $R_3$ are —$(CH_2)_n$—COOR, —$(CH_2)_n$—CONRR', —$(CH_2)_n$—NRCOR', —$(CH_2)_n$—NRCOOR', —$(CH_2)_n$—SO$_m$R, —$(CH_2)_n$—PO$_m$R, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl, $R_1$ and $R_3$ are —$(CH_2)_n$—NRR' or —$(CH_2)_n$—NH(C=NH)NRR', and $R_2$ is —$(CH_2)_n$—COOR, —$(CH_2)_n$—CONRR', —$(CH_2)_n$—NRCOR', —$(CH_2)_n$—NRCOOR', —$(CH_2)_n$—SO$_m$R, —$(CH_2)_n$—PO$_m$R, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl, or $R_1$ and $R_3$ are —$(CH_2)_n$—COOR, —$(CH_2)_n$—CONRR', —$(CH_2)_n$—NRCOR', —$(CH_2)_n$—NRCOOR', —$(CH_2)_n$—SO$_m$R, —$(CH_2)_n$—PO$_m$R, and $R_2$ is —$(CH_2)_n$—NRR' or —$(CH2)_n$—NH(C=NH)NRR', wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl.

8. The compound of claim 2, wherein X is —NHC(O)CH$_2$R$_3$ and R$_3$ is —NH$_2$ or $C_1$-$C_{10}$ alkyl, optionally substituted with —COOH.

9. The compound of claim 3, wherein X' is —NHC(O)CH$_2$NH$_2$.

10. The compound of claim 2, wherein $R_1$ or $R_2$ is isopropyl, isobutyl, n-butyl, sec-butyl or n-pentyl.

11. The compound of claim 3, wherein $R_1$, $R_2$ or $R_3$ is isopropyl, isobutyl, n-butyl, sec-butyl or n-pentyl.

12. The compound of claim 3, wherein $R_1$, $R_2$ or $R_3$ is:

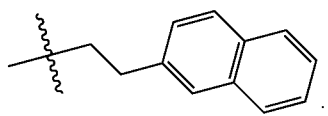 [SMILES: *CCc1ccc2ccccc2c1]

13. The compound of claim 1, wherein the compound is:
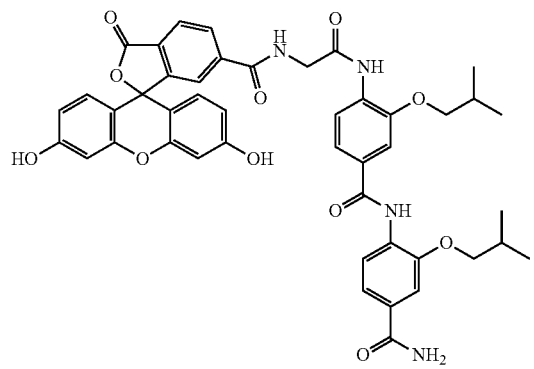
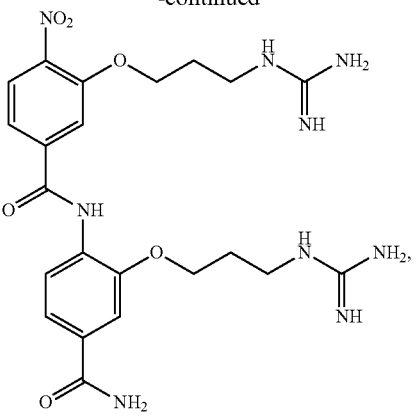
-continued
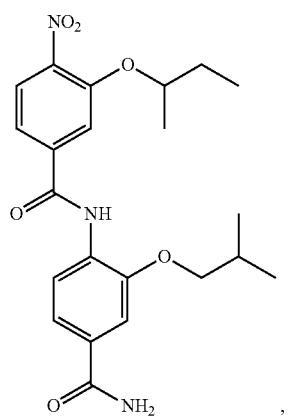
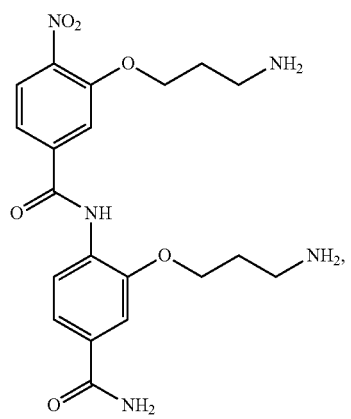
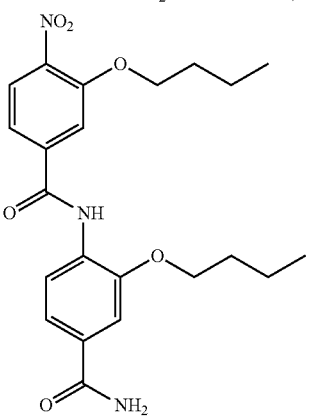
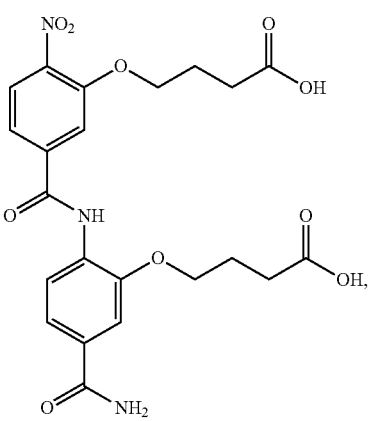
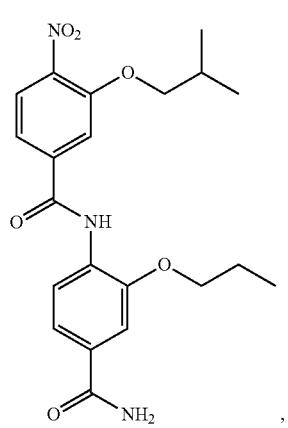
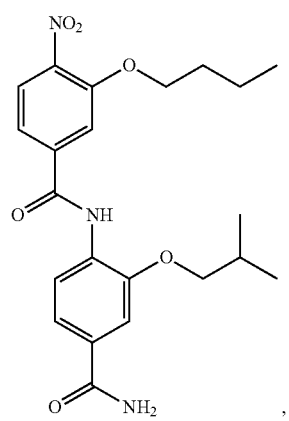

73
-continued
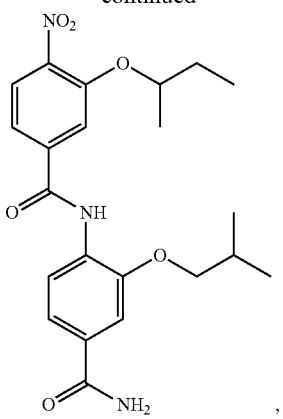
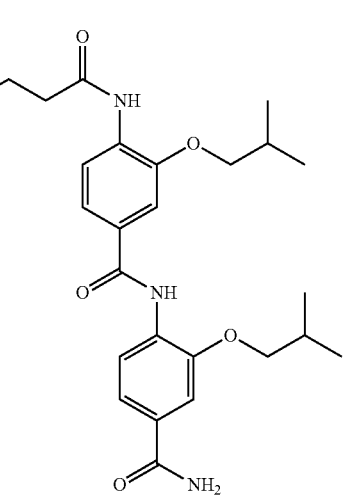
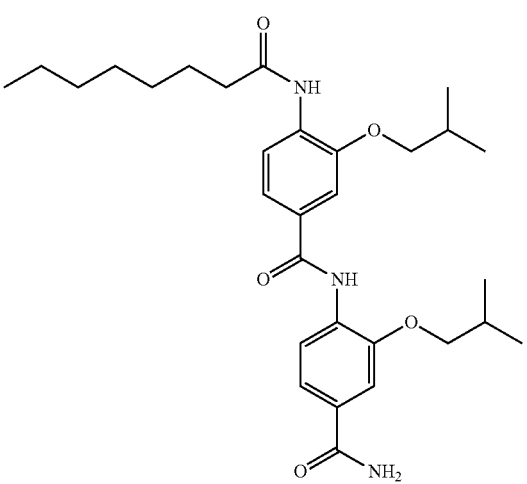
74
-continued
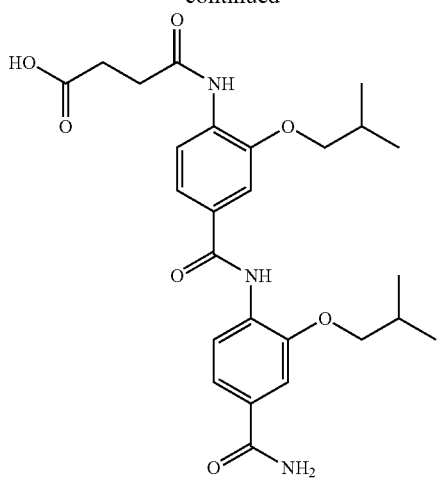
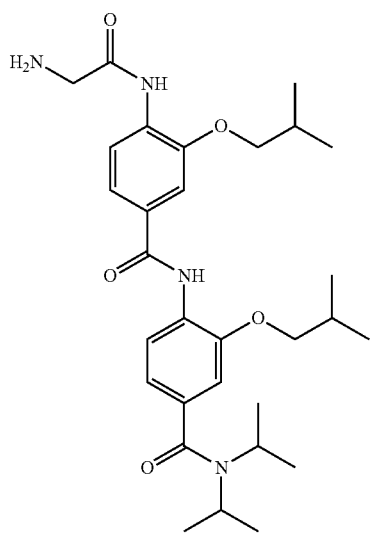
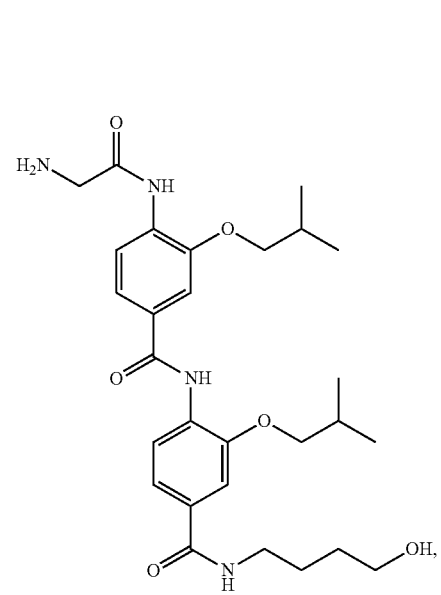

75
-continued
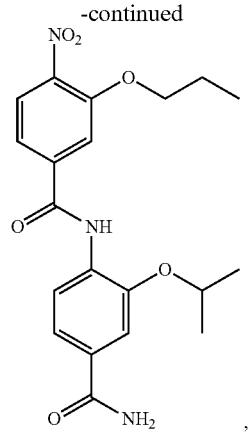
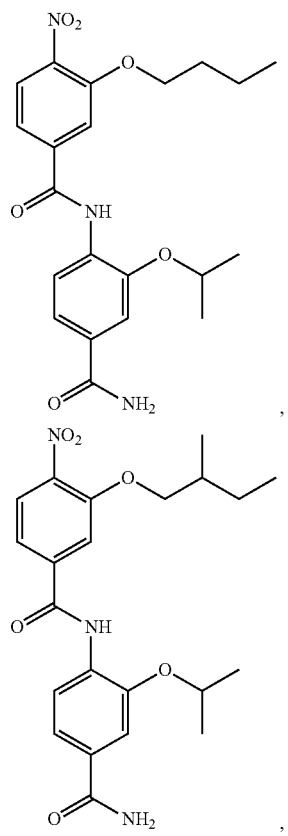
76
-continued
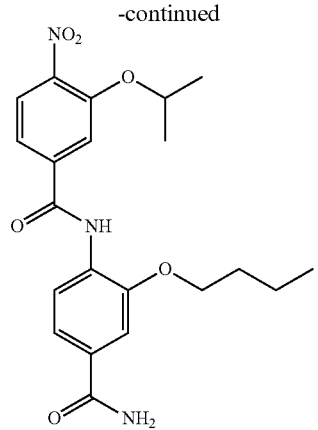
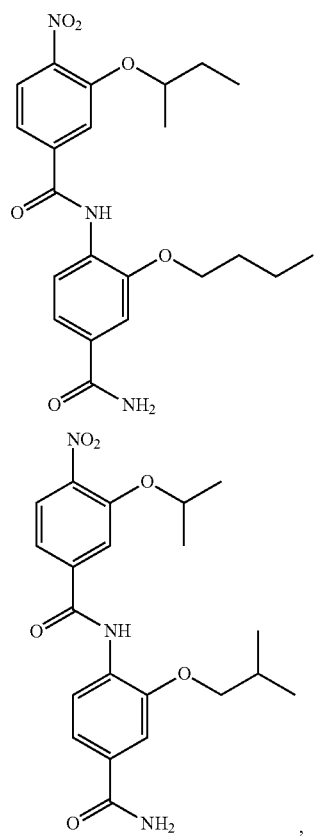
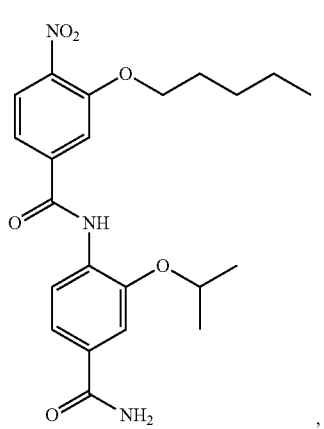

77
-continued
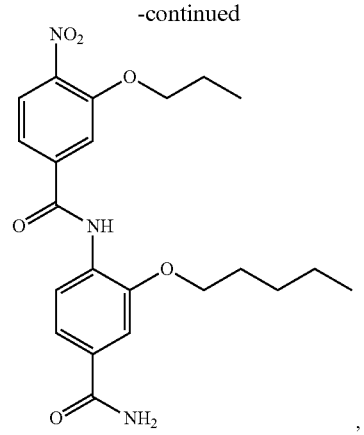
78
-continued
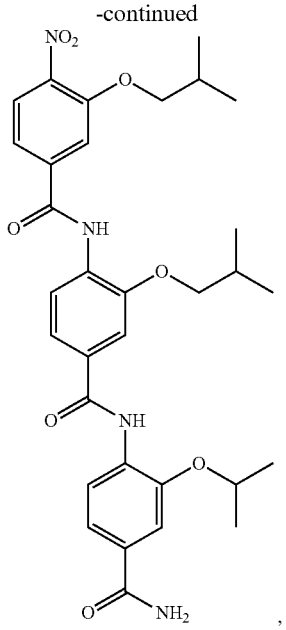
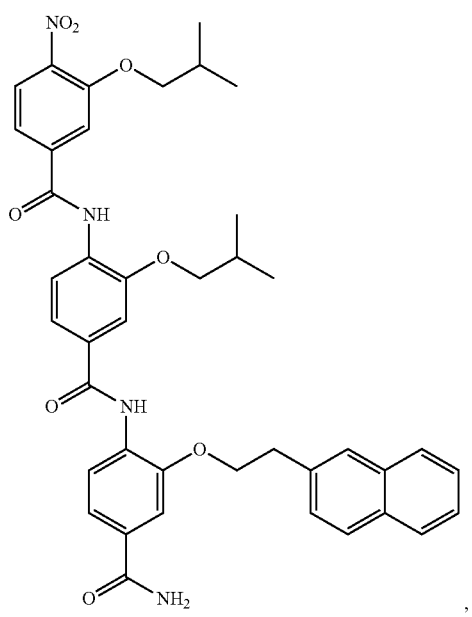

79
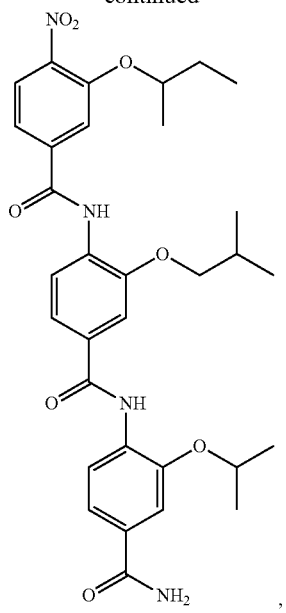
,
80
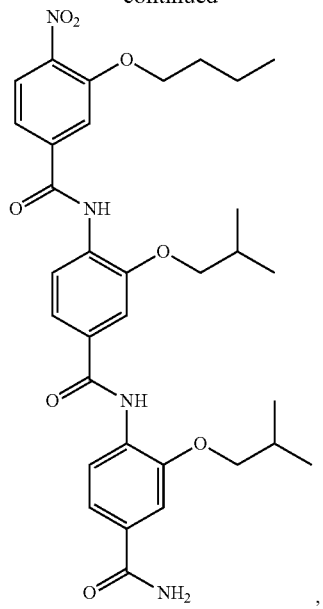
,
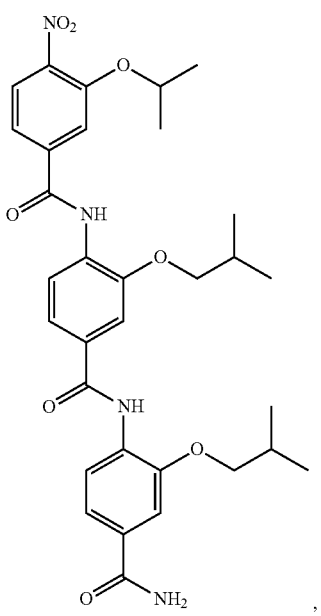
,
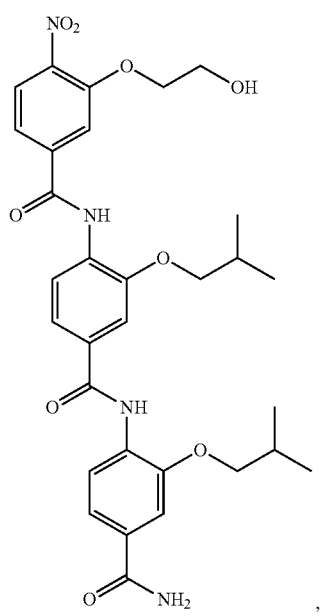
,

81
-continued
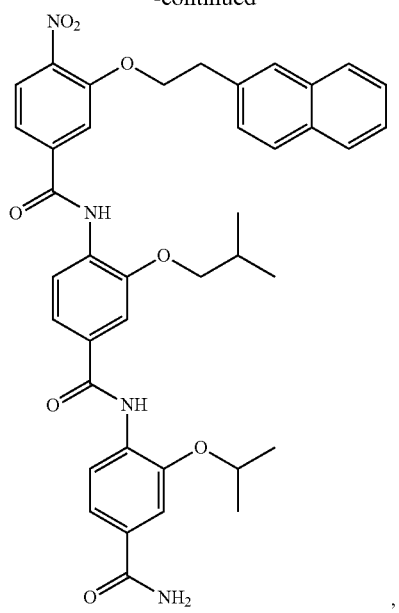
,
82
-continued
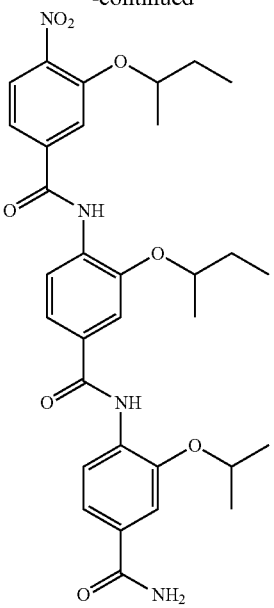
,
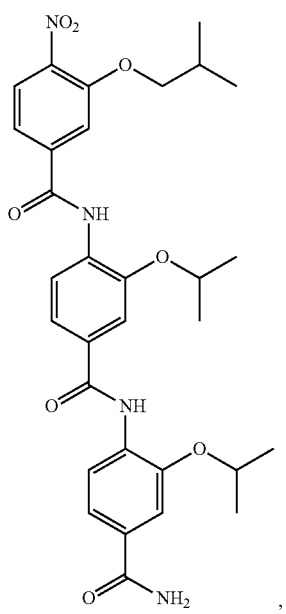
,
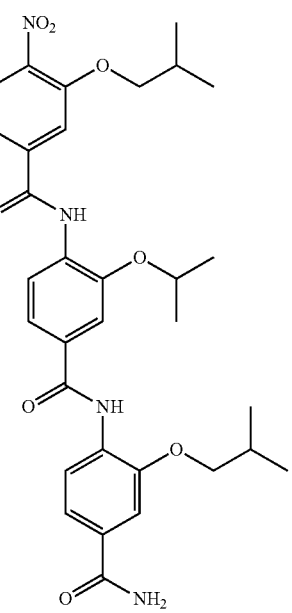
, 83
-continued
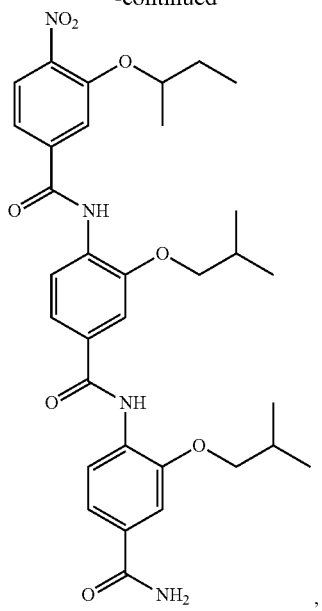
,
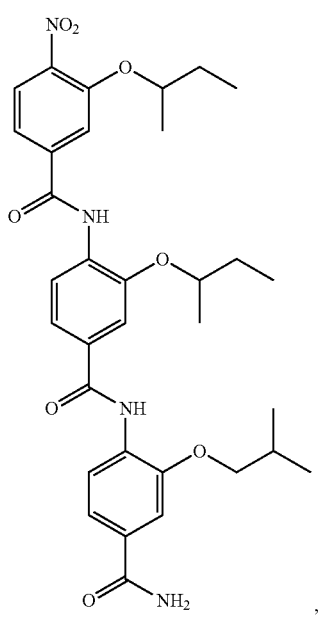
,
84
-continued
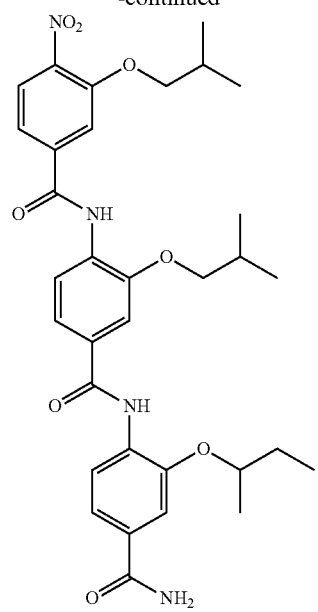
,
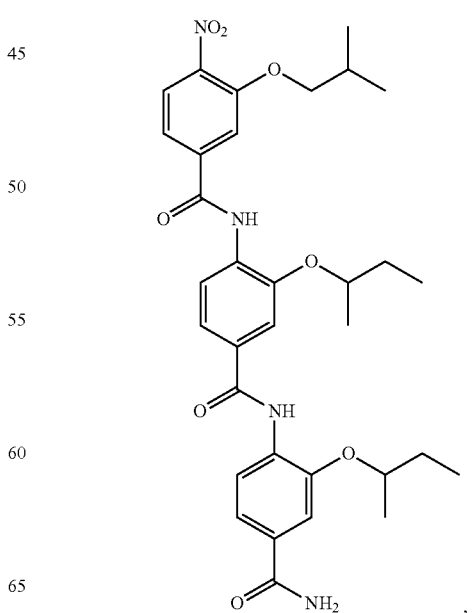
, or 85
-continued
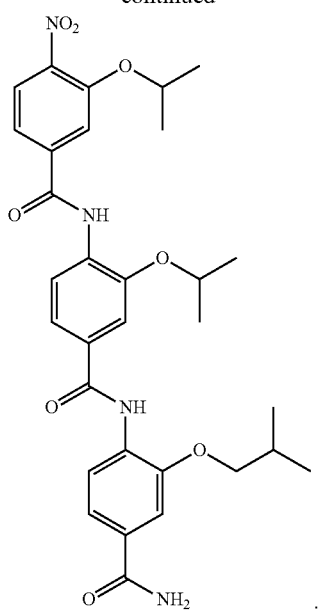
14. A compound of the formula:
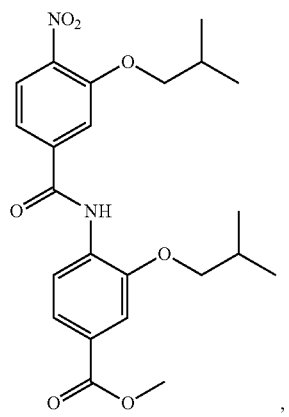
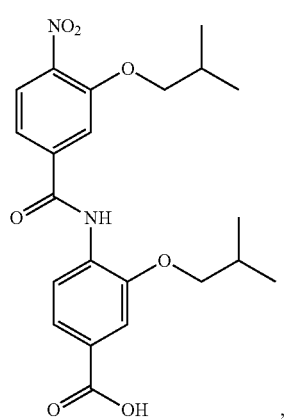
86
-continued
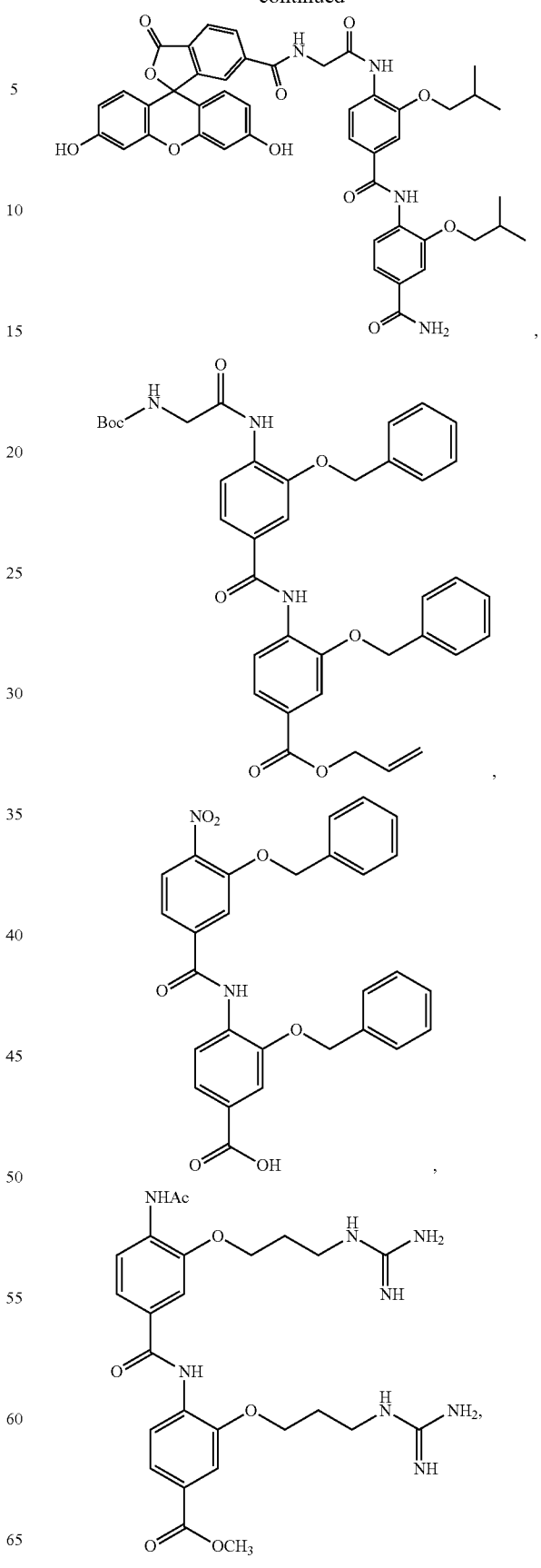

87
-continued
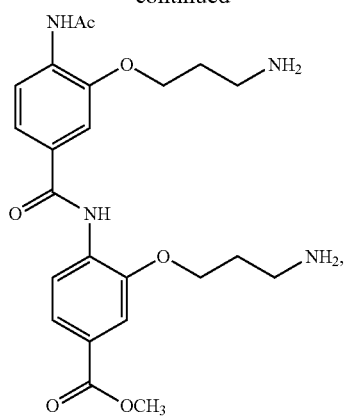
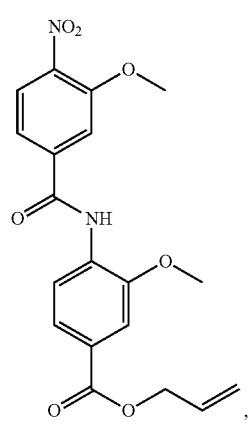
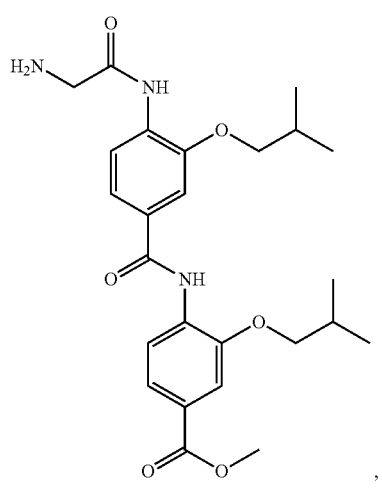
88
-continued
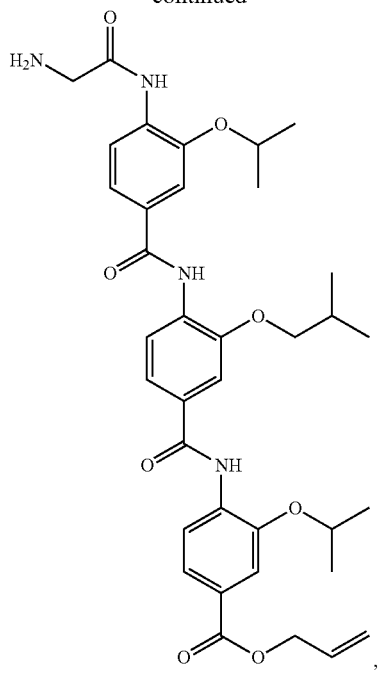
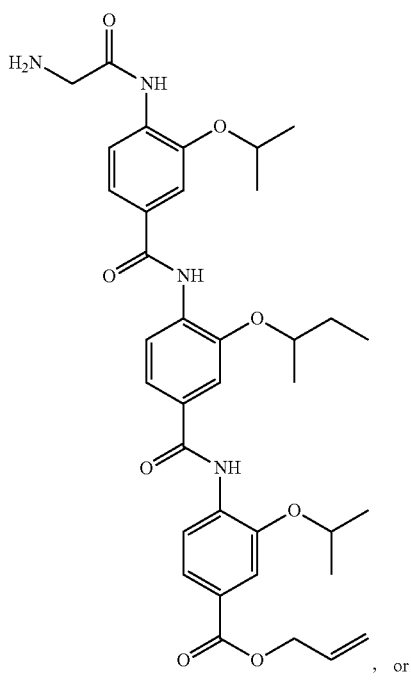, or -continued

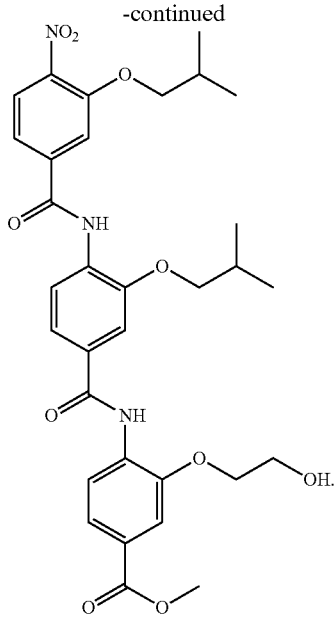

15. A method of inhibiting a androgen receptor (AR)-positive tumor cell in a subject comprising administering to said subject a therapeutically sufficient amount of an oligo-benzamide peptidomimetic compound of formulas (A) or (B):

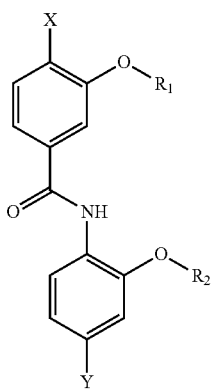
(A)

wherein:
R$_1$ and R$_2$ are each independently C$_1$-C$_{10}$ alkyl, C$_1$-C$_{10}$ alkenyl, C$_1$-C$_{10}$ alkynyl, C$_1$-C$_{15}$ optionally substituted arylalkyl, —(CH$_2$)$_n$—COOR, —(CH$_2$)$_n$—CONRR', —(CH$_2$)$_n$—NRR', —(CH$_2$)$_n$—NH(C=NH)NRR', —(CH$_2$)$_n$—NRCOR', —(CH$_2$)$_n$—NRCOOR', —(CH$_2$)$_n$—OR, —(CH$_2$)$_n$—SR, —(CH$_2$)$_n$—SO$_m$R, —(CH$_2$)$_n$—PO$_m$R, wherein n and m may be any number between 0 and 6 and R and R' may be a H, C$_1$-C$_{10}$ alkyl, C$_1$-C$_{10}$ alkenyl, C$_1$-C$_{10}$ alkynyl, or C$_1$-C$_{15}$ optionally substituted arylalkyl group;

X is —NO$_2$ or —NHC(O)CH$_2$R$_3$, wherein R$_3$ is —NO$_2$, —NH$_2$, —Z, C$_1$-C$_{10}$ alkyl, C$_1$-C$_{10}$ alkenyl, C$_1$-C$_{10}$ alkynyl, or C$_1$-C$_{15}$ arylalkyl, each of which is optionally substituted with —COOR, —CONRR', —NRR', —NH(C=NH)NRR', —NRCOR', —NRCOOR', —OR, —SR, —SO$_n$R, or —PO$_n$R, wherein n may be any number between 0 and 6 and R and R' may be a H, C$_1$-C$_{10}$ alkyl, C$_1$-C$_{10}$ alkenyl, C$_1$-C$_{10}$ alkynyl, or C$_1$-C$_{15}$ optionally substituted arylalkyl group, and wherein Z is:

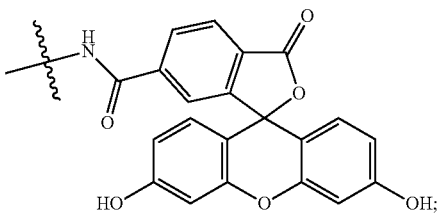

and

Y is —(CH$_2$)$_n$COOR$_4$, —(CH$_2$)$_n$CONR$_4$R$_5$, —(CH$_2$)$_n$NR$_4$R$_5$, —(CH$_2$)$_n$—NR$_4$R$_5$, —(CH$_2$)$_n$—NH(C=NH)NR$_4$R$_5$, —(CH$_2$)$_n$—NR$_4$COR$_5$, —(CH$_2$)$_n$—NR$_4$COOR$_5$, —(CH$_2$)$_n$—OR$_4$, —(CH$_2$)$_n$—SR$_4$, —(CH$_2$)$_n$—SO$_m$R$_4$, —(CH$_2$)$_n$—PO$_m$R$_4$, wherein n and m may be any number between 0 and 6, R$_4$ and R$_5$ are independently selected from —H, C$_1$-C$_{10}$ alkyl, C$_1$-C$_{10}$ alkenyl, C$_1$-C$_{10}$ alkynyl, or C$_1$-C$_{15}$ optionally substituted arylalkyl group; or

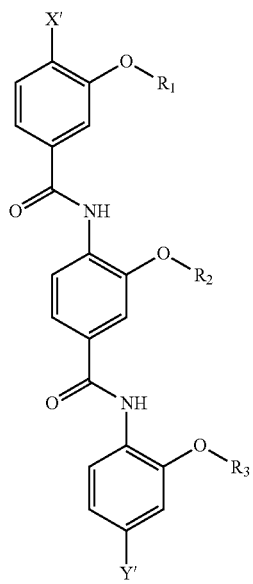
(B)

wherein:
R$_1$, R$_2$ and R$_3$ are each independently C$_1$-C$_{10}$ alkyl, C$_1$-C$_{10}$ alkenyl, C$_1$-C$_{10}$ alkynyl, C$_1$-C$_{15}$ optionally substituted arylalkyl, —(CH$_2$)$_n$—COOR, —(CH$_2$)$_n$—CONRR', —(CH$_2$)$_n$—NRR', —(CH$_2$)$_n$—NH(C=NH)NRR', —(CH$_2$)$_n$—NRCOR', —(CH$_2$)$_n$—NRCOOR', —(CH$_2$)$_n$—OR, —(CH$_2$)$_n$—SR, —(CH$_2$)$_n$—SO$_m$R, —(CH$_2$)$_n$—PO$_m$R, wherein n and m may be any number between 0 and 6 and R and R' may be a H, C$_1$-C$_{10}$ alkyl, C$_1$-C$_{10}$ alkenyl, C$_1$-C$_{10}$ alkynyl, or C$_1$-C$_{15}$ optionally substituted arylalkyl group or

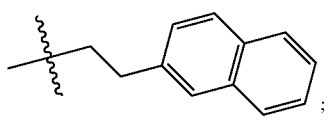 [SMILES: *CCc1ccc2ccccc2c1]

X' is —NO$_2$ or —NHC(O)CH$_2$R$_3$, wherein R$_3$ is —NO$_2$, —NH$_2$, —Z', C$_1$-C$_{10}$ alkyl, C$_1$-C$_{10}$ alkenyl, C$_1$-C$_{10}$ alkynyl, or C$_1$-C$_{15}$ arylalkyl, each of which is optionally substituted with —COOR, —CONRR', —NRR', —NH(C=NH)NRR', —NRCOR', —NRCOOR', —OR, —SR, —SO$_n$R, or —PO$_n$R, wherein n may be any number between 0 and 6 and R and R' may be a H, C$_1$-C$_{10}$ alkyl, C$_1$-C$_{10}$ alkenyl, C$_1$-C$_{10}$ alkynyl, or C$_1$-C$_{15}$ optionally substituted arylalkyl group, and wherein Z' is:

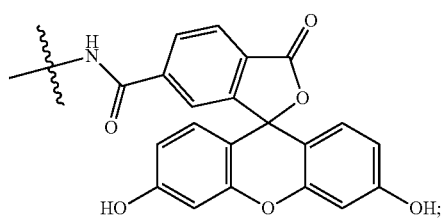 [SMILES: *NC(=O)c1ccc2c(c1)C1(OC2=O)c2ccc(O)cc2Oc2cc(O)ccc21]

and

Y' is —(CH$_2$)$_n$COOR$_4$, —(CH$_2$)$_n$CONR$_4$R$_5$, —(CH$_2$)$_n$NR$_4$R$_5$, —(CH$_2$)$_n$—NR$_4$R$_5$, —(CH$_2$)$_n$—NH(C=NH)NR$_4$R$_5$, —(CH$_2$)$_n$—NR$_4$COR$_5$, —(CH$_2$)$_n$—NR$_4$COOR$_5$, —(CH$_2$)$_n$—OR$_4$, —(CH$_2$)$_n$—SR$_4$, —(CH$_2$)$_n$—SO$_m$R$_4$, —(CH$_2$)$_n$—PO$_m$R$_4$, wherein n and m may be any number between 0 and 6, R$_4$ and R$_5$ are independently selected from —H, C$_1$-C$_{10}$ alkyl, C$_1$-C$_{10}$ alkenyl, C$_1$-C$_{10}$ alkynyl, or C$_1$-C$_{15}$ optionally substituted arylalkyl group.

16. The method of claim 15, wherein the compound is of formula (A).

17. The method of claim 15, wherein the compound is of formula (B).

18. The method of claim 15, wherein the compound is:

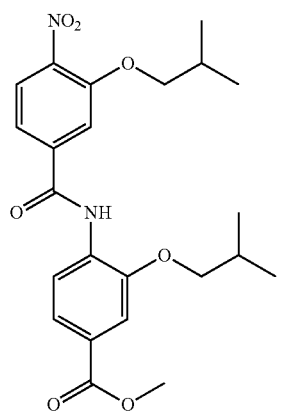

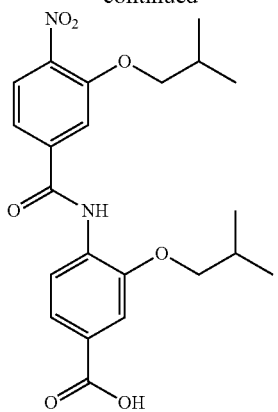

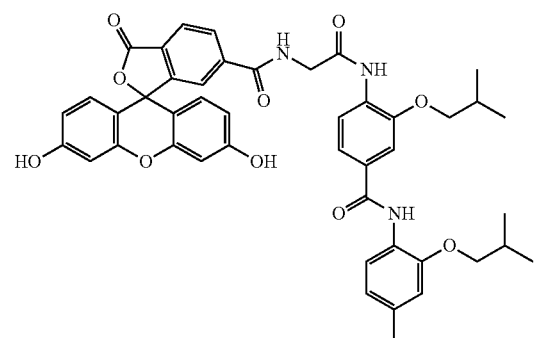

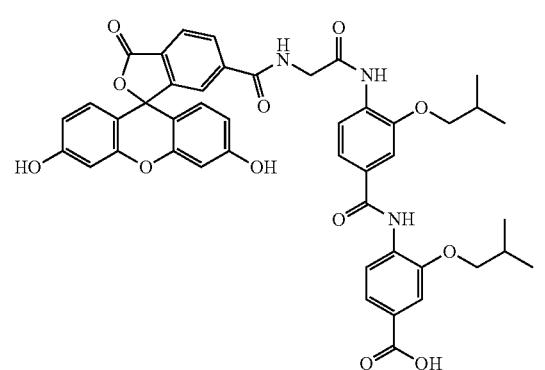

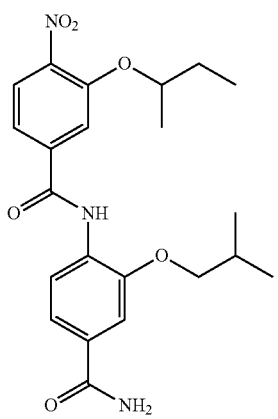

93
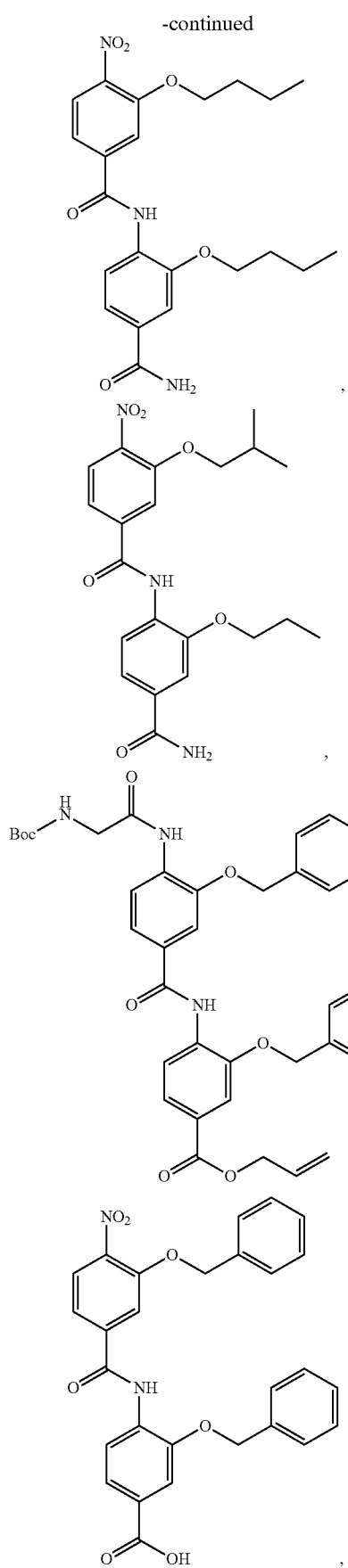
94
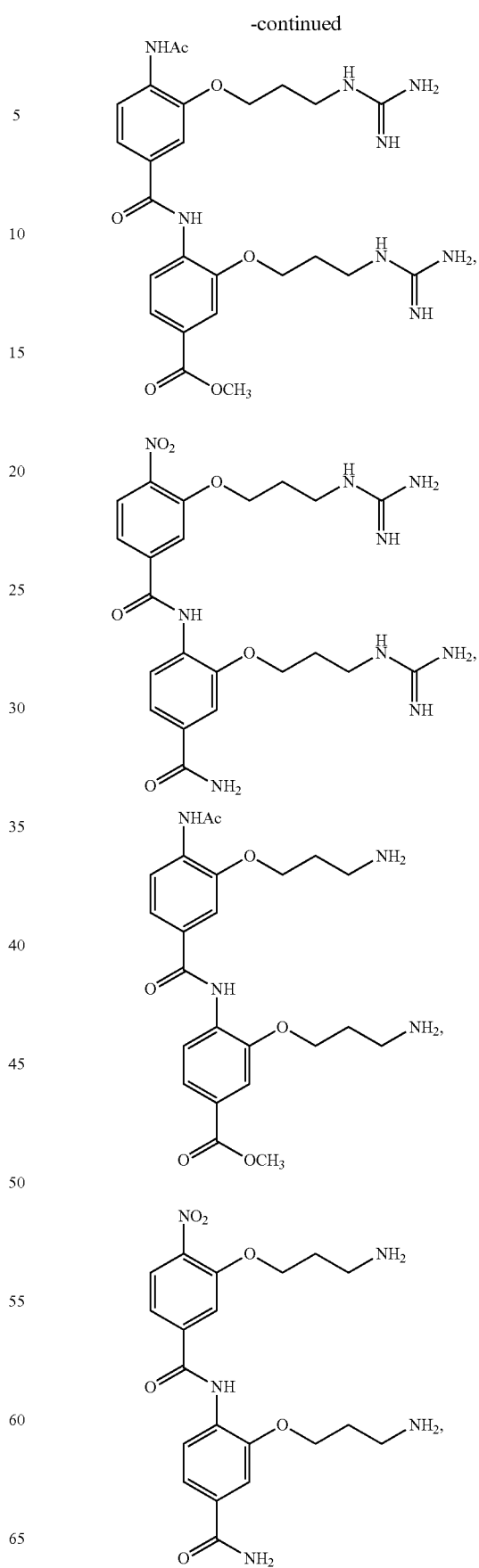

95
-continued
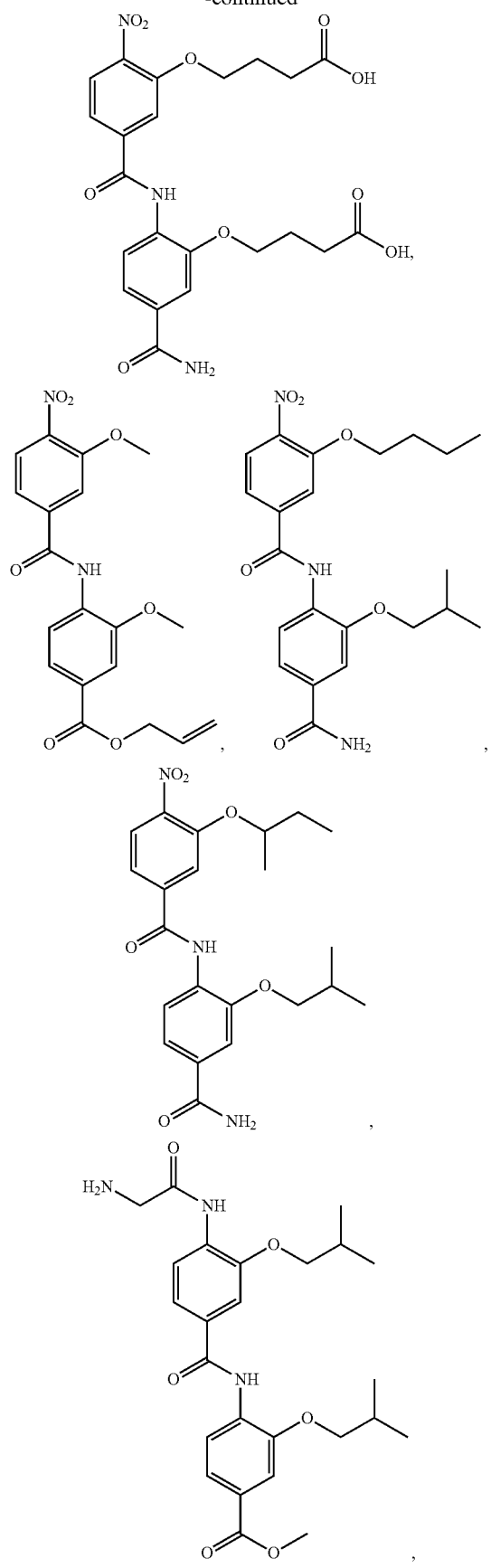
96
-continued
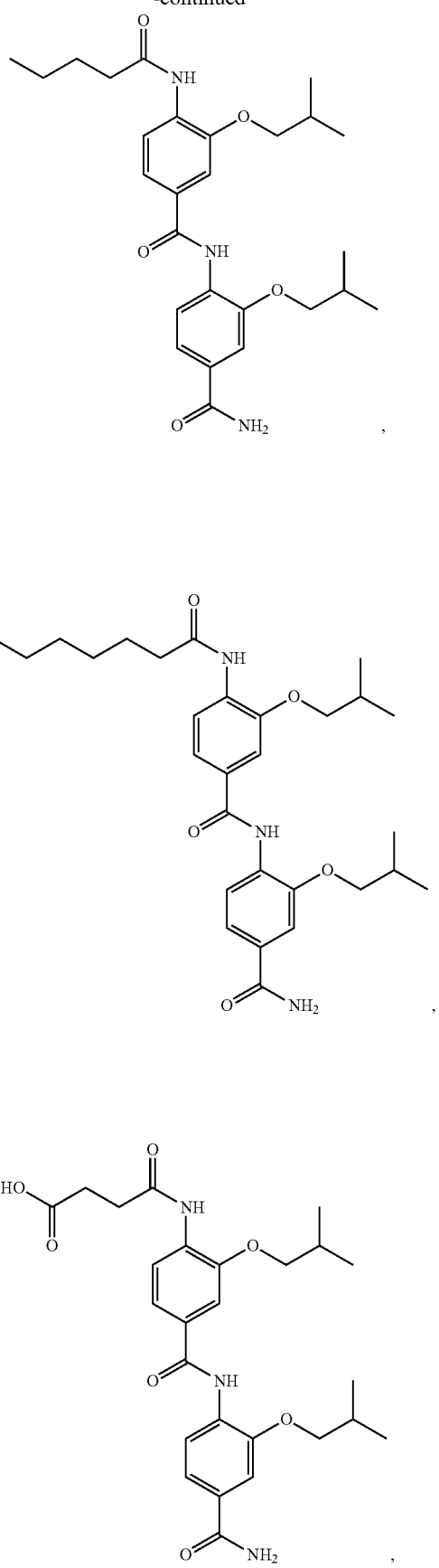

97
-continued
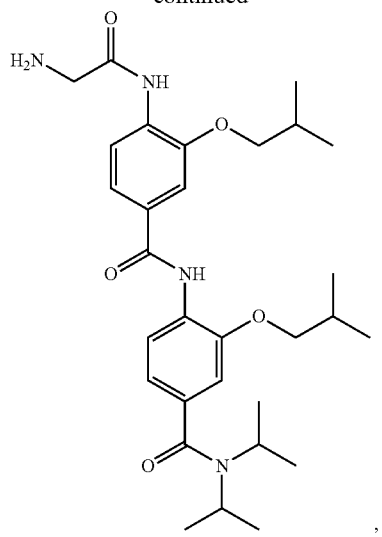
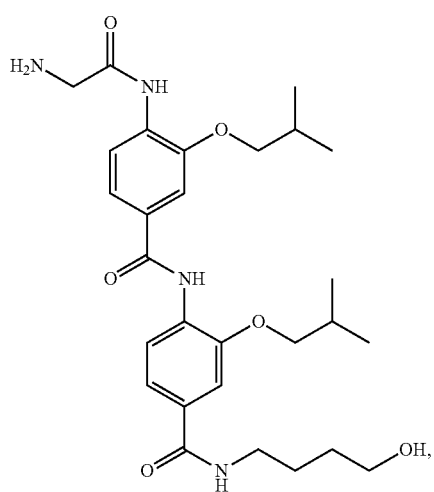
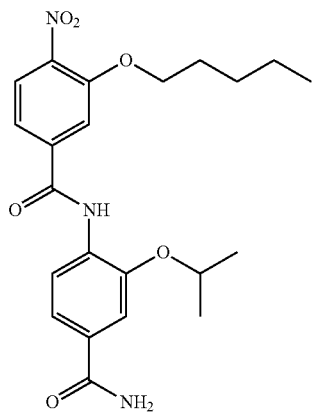
98
-continued
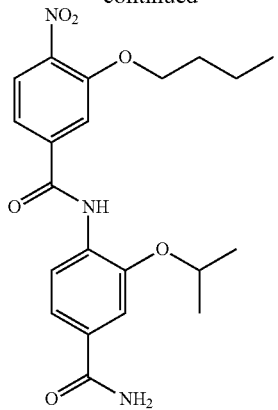
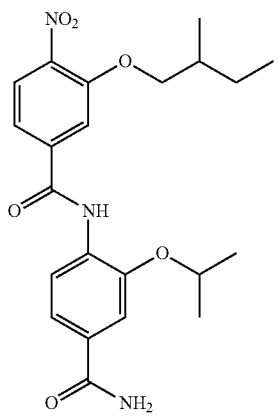
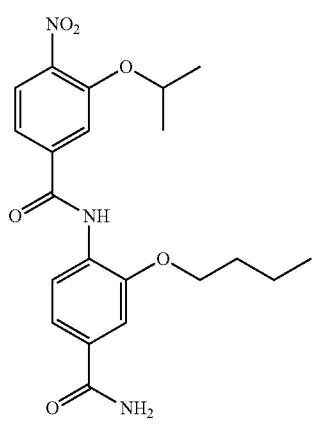

99
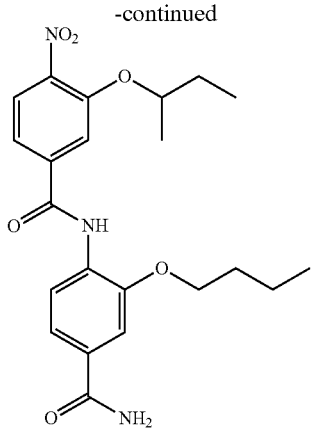
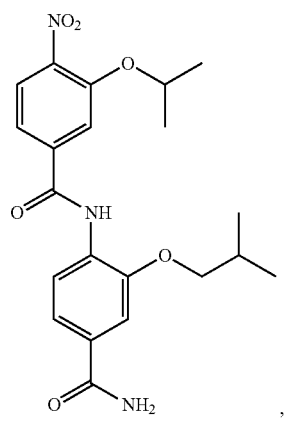
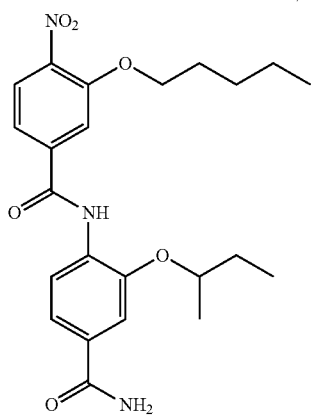
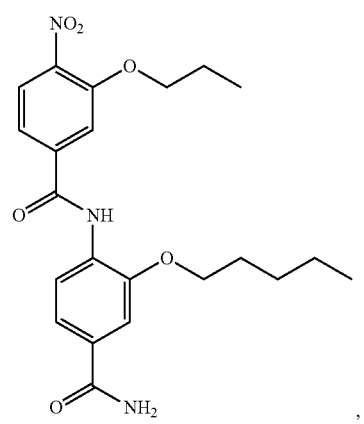
100
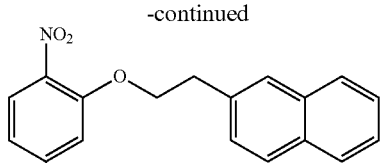
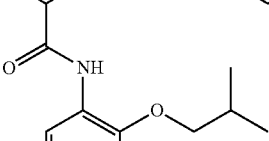
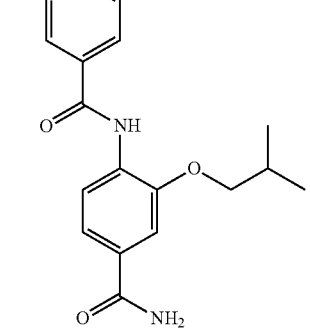
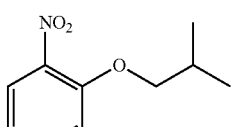
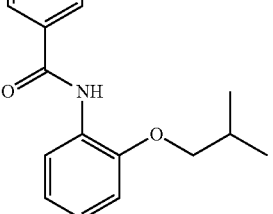
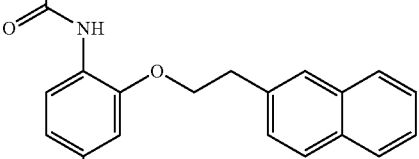
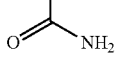

101
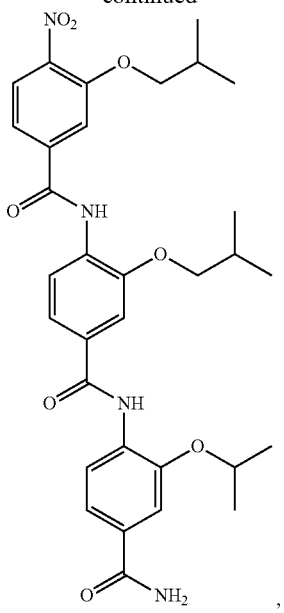
,
102
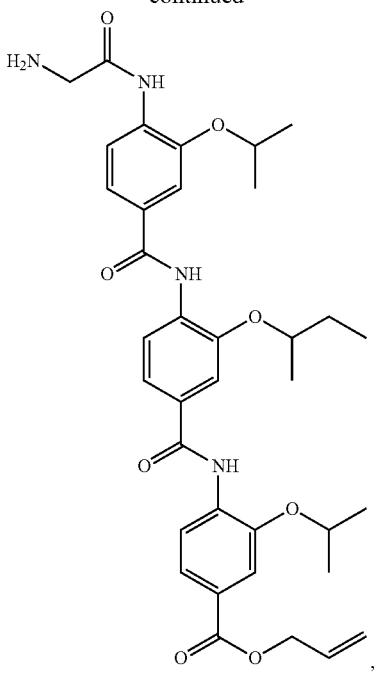
,
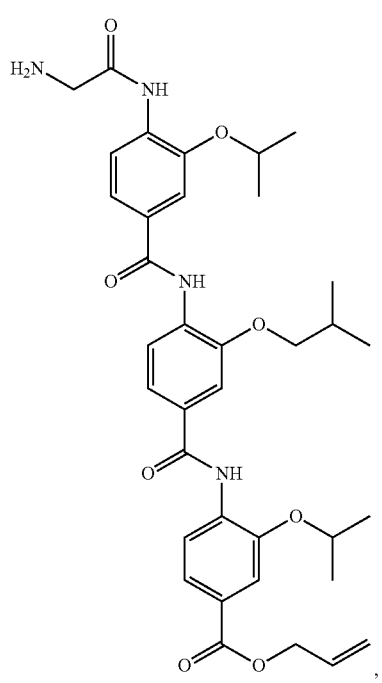
,
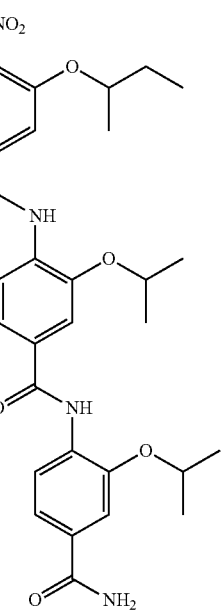
,

103
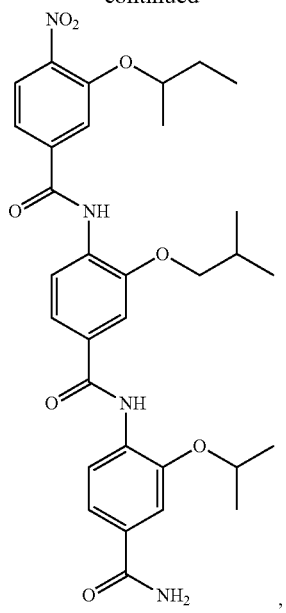
104
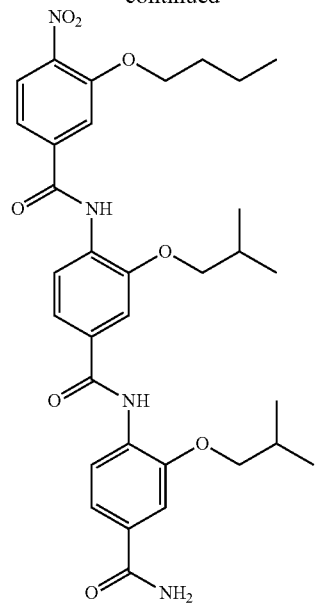
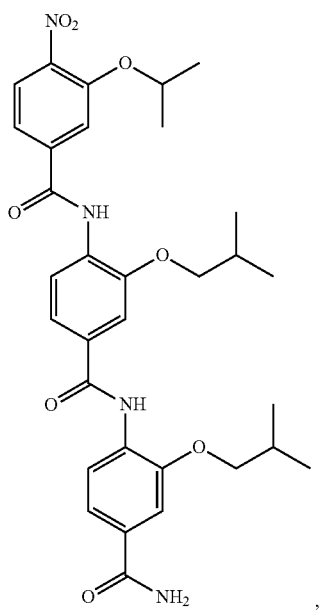
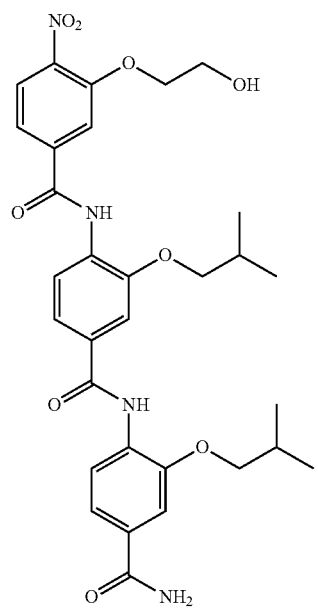

105
-continued
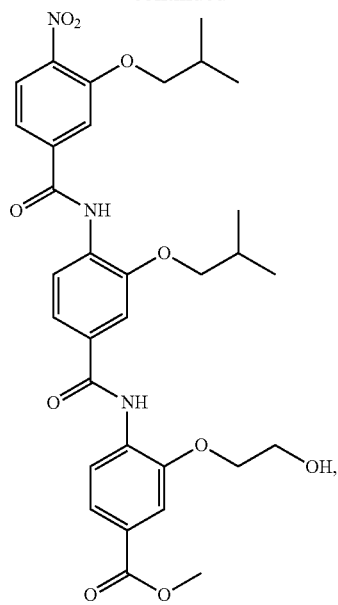 [SMILES: COC(=O)c1ccc(NC(=O)c2ccc(NC(=O)c3ccc([N+](=O)[O-])c(OCC(C)C)c3)c(OCC(C)C)c2)c(OCCO)c1]
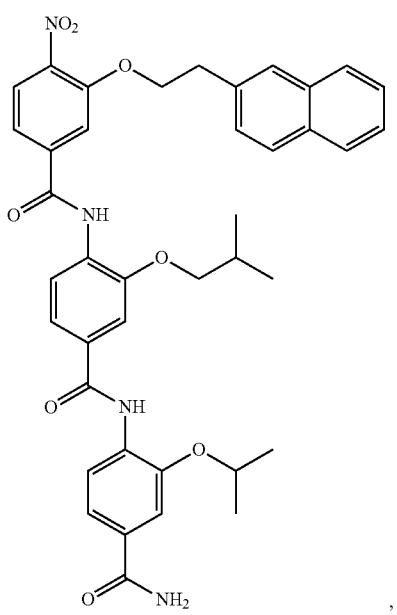
106
-continued
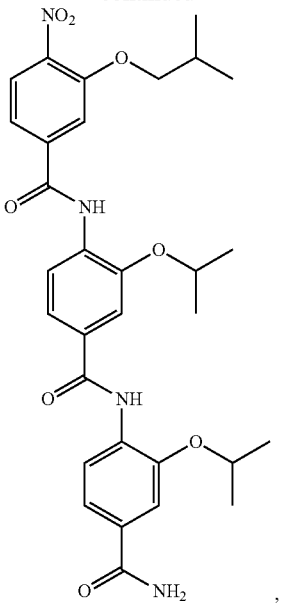
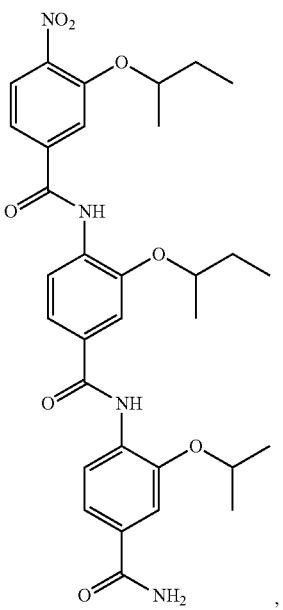

107
-continued
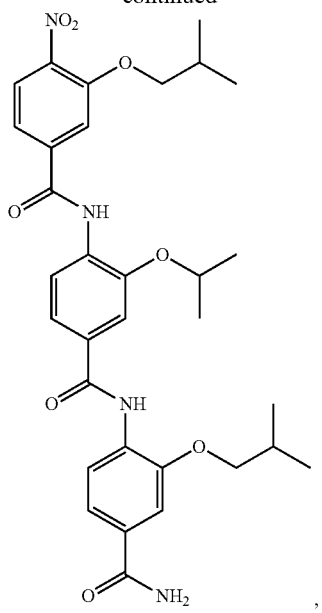
,
108
-continued
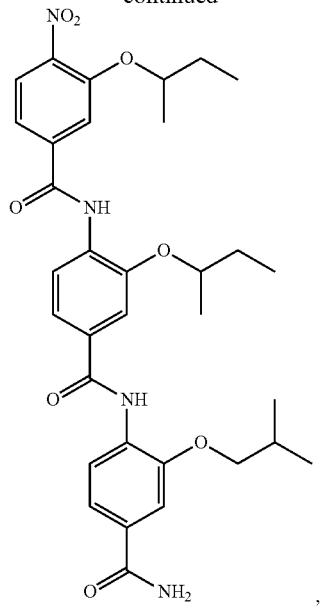
,
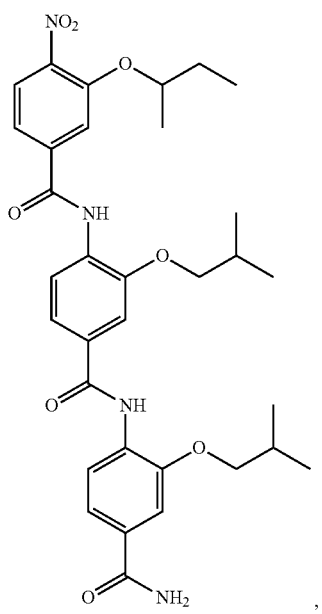
,
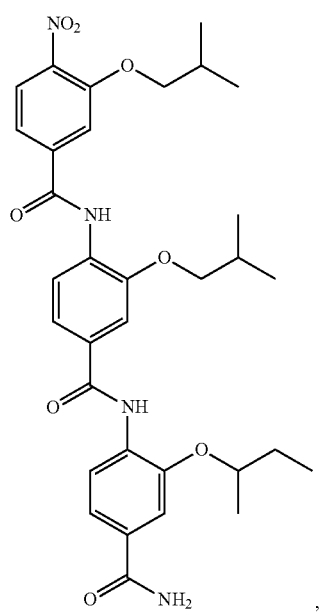
,

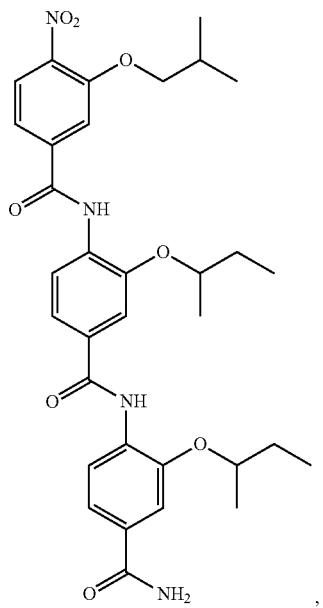
, or
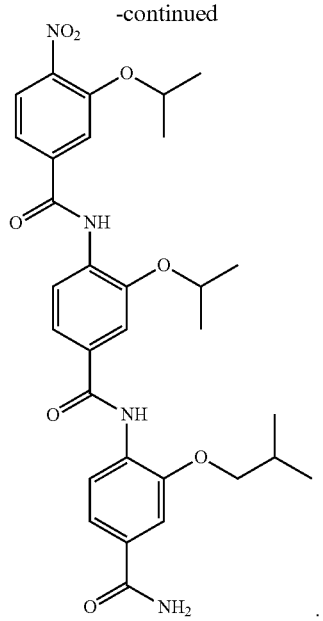
.
19. The method of claim 15, wherein the AR-positive tumor cell is a carcinoma cell, a leukemia cell or a myeloma cell.
20. The method of claim 19, wherein the carcinoma cell is a prostate or breast carcinoma cell.
* * * * *

UNITED STATES PATENT AND TRADEMARK OFFICE
CERTIFICATE OF CORRECTION

PATENT NO. : 9,856,206 B2
APPLICATION NO. : 14/932480
DATED : January 2, 2018
INVENTOR(S) : Jung-Mo Ahn and Ganesh Raj Page 1 of 2

It is certified that error appears in the above-identified patent and that said Letters Patent is hereby corrected as shown below:

On the Title Page

Item (74) Attorney, Agent, or Firm, delete "Paker" and insert --Parker-- therefor.

In the Claims

In Claim 13, Column 75, Lines 34-50, delete chemical drawing

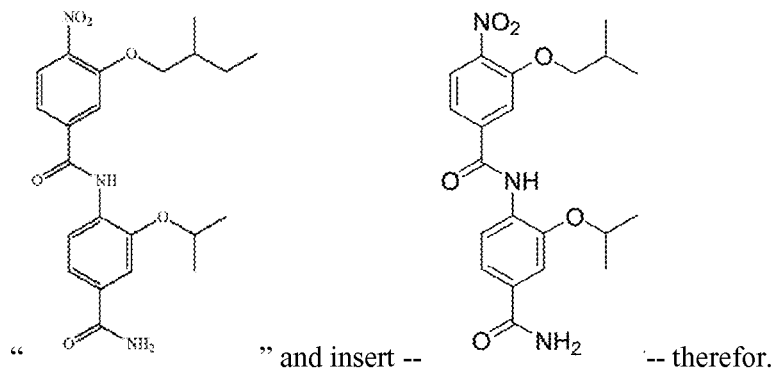

" and insert -- -- therefor.

In Claim 14, Column 86, Lines 2-15, delete chemical drawing

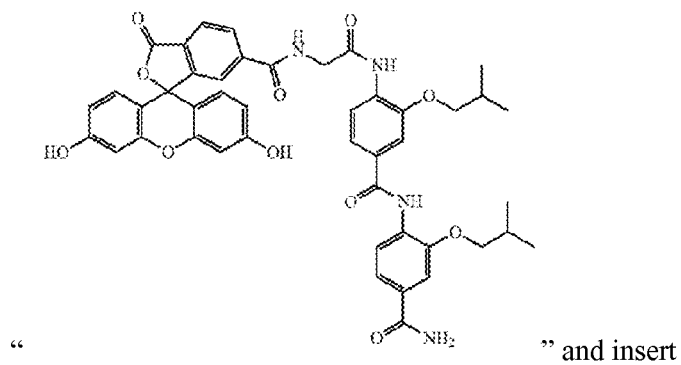

" and insert

Signed and Sealed this
Seventeenth Day of April, 2018

Andrei Iancu
*Director of the United States Patent and Trademark Office*

CERTIFICATE OF CORRECTION (continued)
U.S. Pat. No. 9,856,206 B2

Page 2 of 2

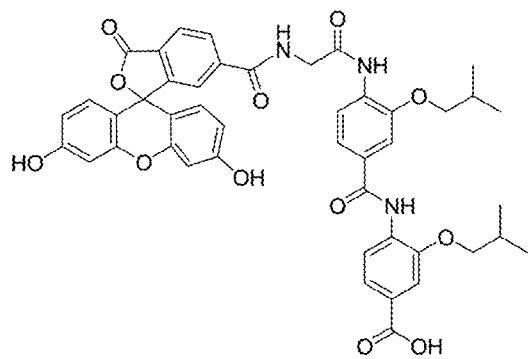

-- -- therefor.

In Claim 18, Column 98, Lines 19-34, delete chemical drawing

" 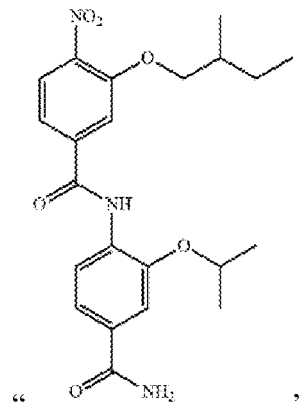 " and insert -- 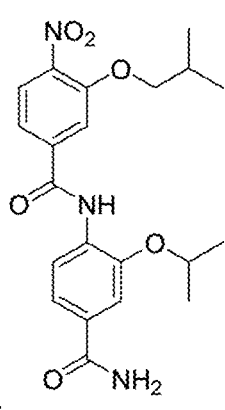 -- therefor.